(12) United States Patent
Kokoris et al.

(10) Patent No.: US 9,771,614 B2
(45) Date of Patent: Sep. 26, 2017

(54) HIGH THROUGHPUT NUCLEIC ACID SEQUENCING BY EXPANSION AND RELATED METHODS

(71) Applicant: Stratos Genomics Inc., Seattle, WA (US)

(72) Inventors: Mark Stamatios Kokoris, Bothell, WA (US); Robert N. McRuer, Mercer Island, WA (US)

(73) Assignee: Stratos Genomics Inc., Seattle, WA (US)

( * ) Notice: Subject to any disclaimer, the term of this patent is extended or adjusted under 35 U.S.C. 154(b) by 230 days.

(21) Appl. No.: 14/590,894

(22) Filed: Jan. 6, 2015

(65) Prior Publication Data

US 2015/0284787 A1 Oct. 8, 2015

Related U.S. Application Data

(63) Continuation of application No. 14/449,912, filed on Aug. 1, 2014, now abandoned, which is a continuation of application No. 13/146,800, filed as application No. PCT/US2010/022654 on Jan. 29, 2010, now abandoned.

(60) Provisional application No. 61/148,332, filed on Jan. 29, 2009, provisional application No. 61/148,334, filed on Jan. 29, 2009, provisional application No. 61/148,327, filed on Jan. 29, 2009.

(51) Int. Cl.
*B82Y 15/00* (2011.01)
*C12Q 1/68* (2006.01)
*C12P 19/34* (2006.01)

(52) U.S. Cl.
CPC ............ *C12Q 1/6869* (2013.01); *C12P 19/34* (2013.01)

(58) Field of Classification Search
None
See application file for complete search history.

(56) References Cited

U.S. PATENT DOCUMENTS

| 7,060,440 B1 | 6/2006 | Kless |
| 2004/0248103 A1 | 12/2004 | Feaver et al. |
| 2007/0048748 A1 | 3/2007 | Williams et al. |
| 2007/0190542 A1 | 8/2007 | Ling et al. |

FOREIGN PATENT DOCUMENTS

| CN | 1136330 A | 11/1996 |
| EP | 1 645 628 A1 | 4/2006 |
| WO | WO 2008/157696 A2 | 12/2008 |
| WO | WO 2009/055617 A1 | 4/2009 |

OTHER PUBLICATIONS

Lee et al., "UV nano embossing for polymer nano structures with non-transparent mold insert," *Microsystem Technologies* 13(5): 593-599, Jan. 2007.

(Continued)

*Primary Examiner* — Robert T Crow
(74) *Attorney, Agent, or Firm* — Seed IP Law Group LLP

(57) ABSTRACT

A method for detecting an analyte employing a nanopore substrate positioned between first and second reservoirs by providing an indicator molecule not associated with the analyte and detecting a change in an optical signal emitted from the indicator moiety as the analyte translocates through a nanopore channel of the nanopore substrate.

20 Claims, 30 Drawing Sheets

(56) References Cited

OTHER PUBLICATIONS

Sauer et al., "A novel procedure for efficient genotyping of single nucleotide polymorphisms," *Nucleic Acids Research* 28(5): E13i-viii, 2000.

Vallone et al., "Genotyping SNPs Using a UV-Photocleavable Oligonucleotide in MALDI-TOF MS," Chapter 12 in *Methods in Molecular Biology, vol. 297: Forensic DNA Typing Protocols*, Carracedo, ed., Humana Press Inc., Totowa, NY, 2005, pp. 169-178.

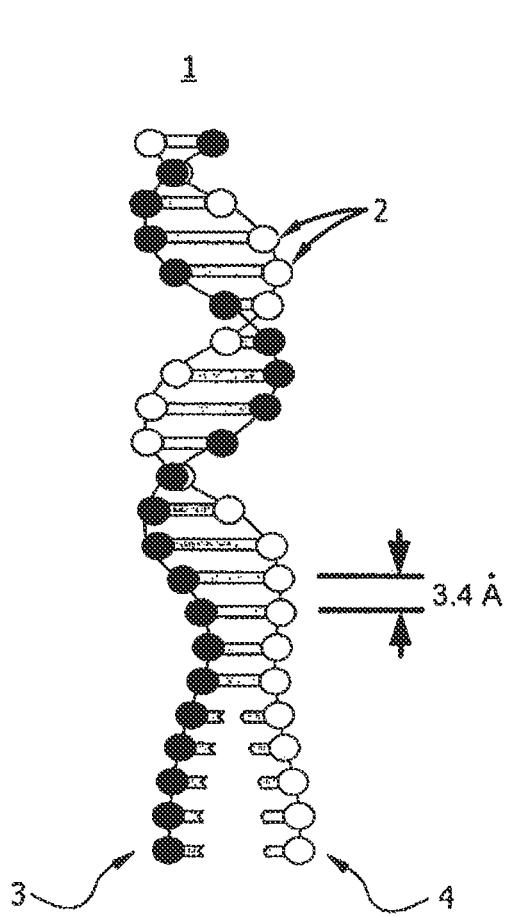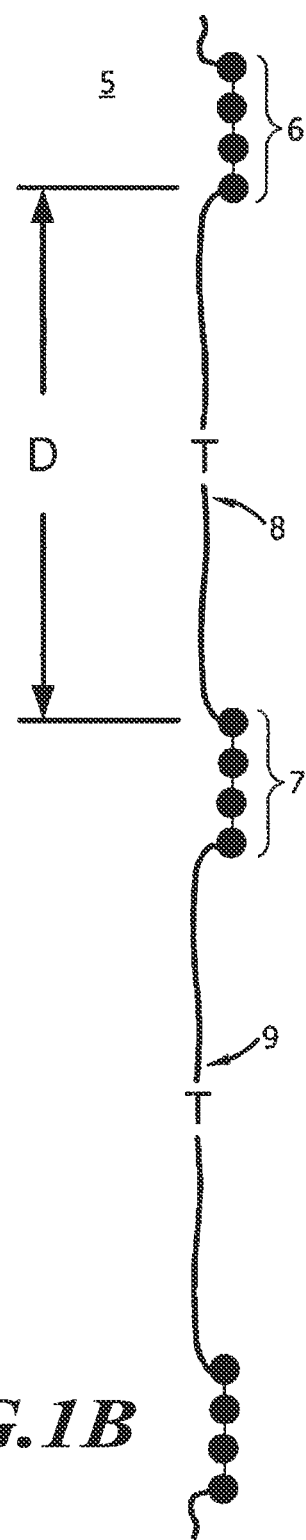
FIG.1A
FIG.1B

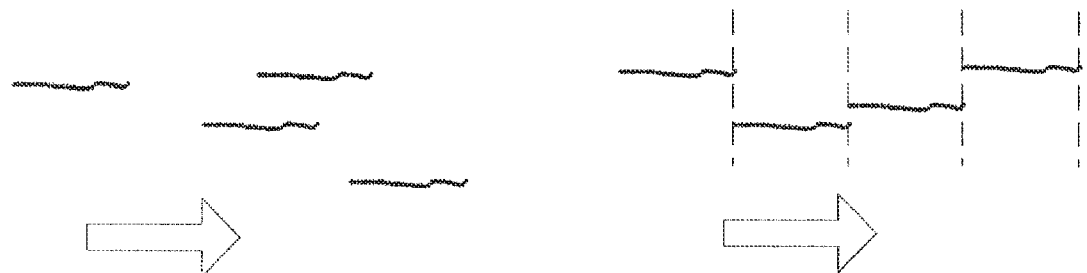
FIG.15A
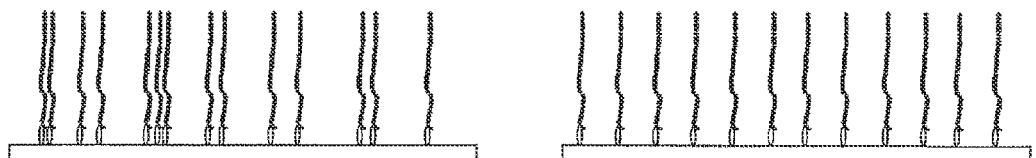
FIG.15B
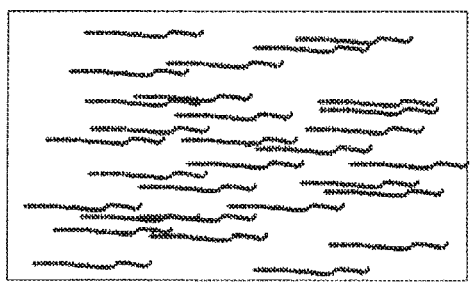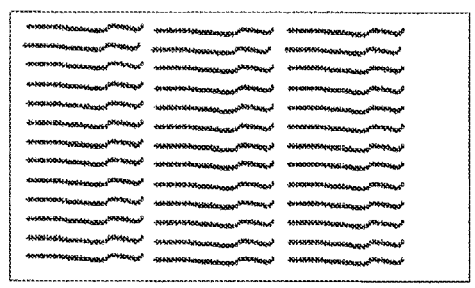
FIG.15C

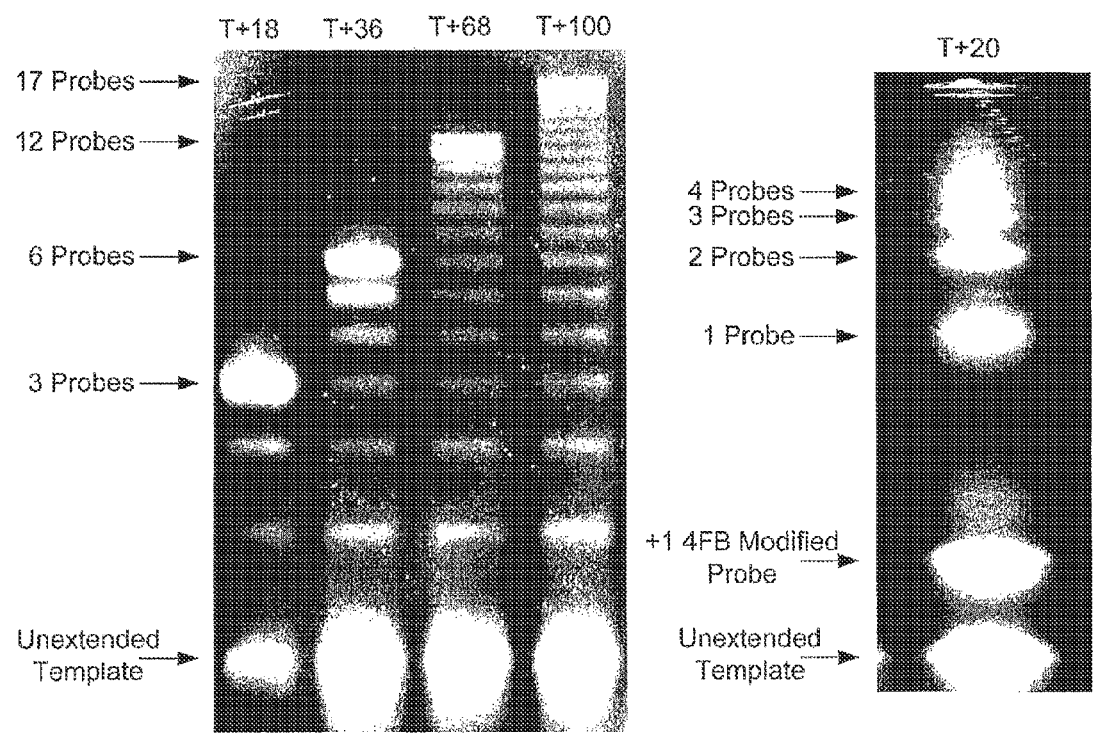
*FIG.24A*  *FIG.24B*

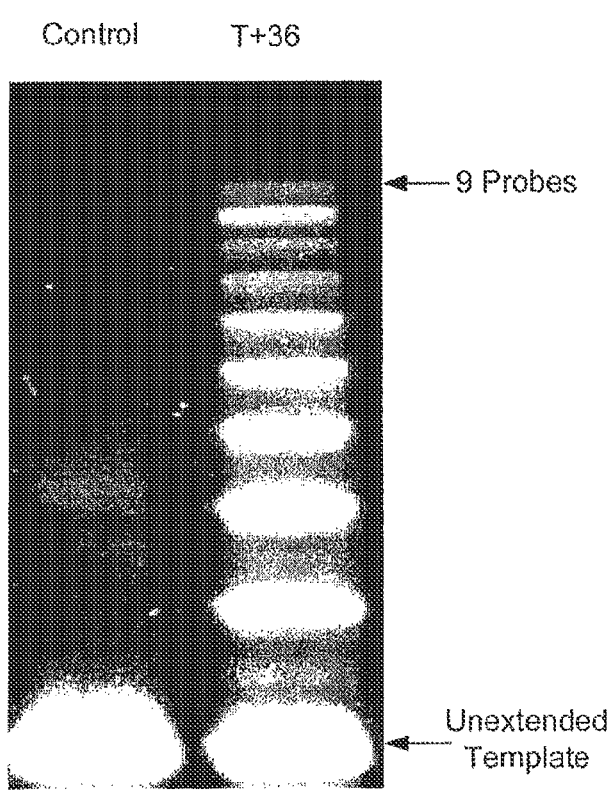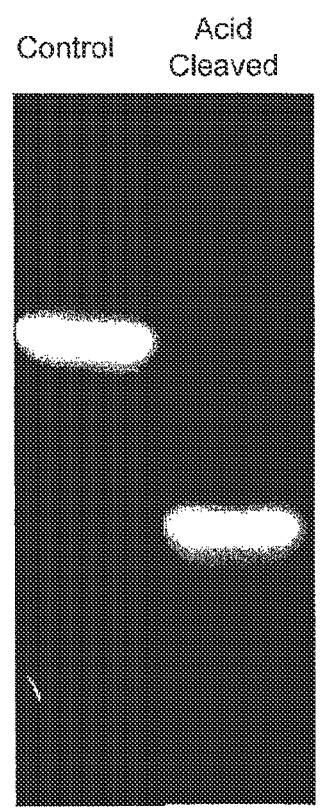
*FIG.24C*  *FIG.24D*

HIGH THROUGHPUT NUCLEIC ACID SEQUENCING BY EXPANSION AND RELATED METHODS

CROSS-REFERENCES TO RELATED APPLICATIONS

This application is a continuation of U.S. application Ser. No. 13/146,800, a U.S. national stage entry of PCT/US2010/022654 filed Jan. 29, 1010, which claims the benefit under 35 U.S.C. §119(e) of U.S. Provisional Patent Application No. 61/148,332 filed on Jan. 29, 2009; U.S. Provisional Patent Application No. 61/148,334 filed on Jan. 29, 2009; and U.S. Provisional Patent Application No. 61/148,327 filed on Jan. 29, 2009; all of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 870225_403C2_SEQUENCE_LISTING.txt. The text file is 1 KB, was created on Jun. 22, 2015, and is being submitted electronically via EFS-Web.

BACKGROUND

Technical Field

This invention is generally related to nucleic acid sequencing, as well as methods and products relating to the same.

Description of the Related Art

Nucleic acid sequences encode the necessary information for living things to function and reproduce, and are essentially a blueprint for life. Determining such sequences is therefore a tool useful in pure research into how and where organisms live, as well as in applied sciences such as drug development. In medicine, sequencing tools can be used for diagnosis and to develop treatments for a variety of pathologies, including cancer, heart disease, autoimmune disorders, multiple sclerosis, or obesity. In industry, sequencing can be used to design improved enzymatic processes or synthetic organisms. In biology, such tools can be used to study the health of ecosystems, for example, and thus have a broad range of utility.

An individual's unique DNA sequence provides valuable information concerning their susceptibility to certain diseases. The sequence will provide patients with the opportunity to screen for early detection and to receive preventative treatment. Furthermore, given a patient's individual blueprint, clinicians will be capable of administering personalized therapy to maximize drug efficacy and to minimize the risk of an adverse drug response. Similarly, determining the blueprint of pathogenic organisms can lead to new treatments for infectious diseases and more robust pathogen surveillance. Whole genome DNA sequencing will provide the foundation for modern medicine.

DNA sequencing is the process of determining the order of the chemical constituents of a given DNA polymer. These chemical constituents, which are called nucleotides, exist in DNA in four common forms: deoxyadenosine (A), deoxyguanosine (G), deoxycytidine (C), and deoxythymidine (T). Sequencing of a diploid human genome requires determining the sequential order of approximately 6 billion nucleotides.

Currently, most DNA sequencing is performed using the chain termination method developed by Frederick Sanger. This technique, termed Sanger Sequencing, uses sequence specific termination of DNA synthesis and fluorescently modified nucleotide reporter substrates to derive sequence information. This method sequences a target nucleic acid strand, or read length, of up to 1000 bases long by using a modified Polymerase Chain Reaction (PCR). In this modified reaction the sequencing is randomly interrupted at select base types (A, C, G or T) and the lengths of the interrupted sequences are determined by capillary gel electrophoresis. The length then determines what base type is located at that length. Many overlapping read lengths are produced and their sequences are overlaid using data processing to determine the most reliable fit of the data. This process of producing read lengths of sequence is very laborious and expensive and is now being superseded by new methods that have higher efficiency.

The Sanger method was used to provide most of the sequence data in the Human Genome Project which generated the first complete sequence of the human genome. This project took over 10 years and nearly $3B to complete. Given these significant throughput and cost limitations, it is clear that DNA sequencing technologies will need to improve drastically in order to achieve the stated goals put forth by the scientific community. To that end, a number of second generation technologies, which far exceed the throughput and cost per base limitations of Sanger sequencing, are gaining an increasing share of the sequencing market. Still, these "sequencing by synthesis" methods fall short of achieving the throughput, cost, and quality targets required by markets such as whole genome sequencing for personalized medicine.

For example, 454 Life Sciences is producing instruments (e.g., the Genome Sequencer) that can process 100 million bases in 7.5 hours with an average read length of 200 nucleotides. Their approach uses a variation of PCR to produce a homogeneous colony of target nucleic acid, hundreds of bases in length, on the surface of a bead. This process is termed emulsion PCR. Hundreds of thousands of such beads are then arranged on a "picotiter plate". The plate is then prepared for an additional sequencing whereby each nucleic acid base type is sequentially washed over the plate. Beads with target that incorporate the base produce a pyrophosphate byproduct that can be used to catalyze a light producing reaction that is then detected with a camera.

Illumina Inc. has a similar process that uses reversibly terminating nucleotides and fluorescent labels to perform nucleic acid sequencing. The average read length for Illumina's 1G Analyzer is less than 40 nucleotides. Instead of using emulsion PCR to amplify sequence targets, Illumina has an approach for amplifying PCR colonies on an array surface. Both the 454 and Illumina approaches use a complicated polymerase amplification to increase signal strength, perform base measurements during the rate limiting sequence extension cycle, and have limited read lengths because of incorporation errors that degrade the measurement signal to noise proportionally to the read length.

Applied Biosystems uses reversible terminating ligation rather than sequencing-by-synthesis to read the DNA. Like 454's Genome Sequencer, the technology uses bead-based emulsion PCR to amplify the sample. Since the majority of the beads do not carry PCR products, the researchers next use an enrichment step to select beads coated with DNA.

The biotin-coated beads are spread and immobilized on a glass slide array covered with streptavidin. The immobilized beads are then run through a process of 8-mer probe hybridization (each labeled with four different fluorescent dyes), ligation, and cleavage (between the 5th and 6th bases to create a site for the next round of ligation). Each probe interrogates two bases, at positions 4 and 5 using a 2-base encoding system, which is recorded by a camera. Similar to Illumina's approach, the average read length for Applied Biosystems' SOLiD® platform is less than 40 nucleotides.

Other approaches are being developed to avoid the time and expense of the polymerase amplification step by measuring single molecules of DNA directly. Visigen Biotechnologies, Inc. is measuring fluorescently labeled bases as they are sequenced by incorporating a second fluorophore into an engineered DNA polymerase and using Forster Resonance Energy Transfer (FRET) for nucleotide identification. This technique is faced with the challenges of separating the signals of bases that are separated by less than a nanometer and by a polymerase incorporation action that will have very large statistical variation.

A process being developed by LingVitae sequences cDNA inserted into immobilized plasmid vectors. The process uses a Class IIS restriction enzyme to cleave the target nucleic acid and ligate an oligomer into the target. Typically, one or two nucleotides in the terminal 5' or 3' overhang generated by the restriction enzyme determine which of a library of oligomers in the ligation mix will be added to the sticky, cut end of the target. Each oligomer contains "signal" sequences that uniquely identify the nucleotide(s) it replaces. The process of cleavage and ligation is then repeated. The new molecule is then sequenced using tags specific for the various oligomers. The product of this process is termed a "Design Polymer" and always consists of a nucleic acid longer than the one it replaces (e.g., a dinucleotide target sequence is replaced by a "magnified" polynucleotide sequence of as many as 100 base pairs). An advantage of this process is that the duplex product strand can be amplified if desired. A disadvantage is that the process is necessarily cyclical and the continuity of the template would be lost if simultaneous multiple restriction cuts were made.

U.S. Pat. No. 7,060,440 to Kless describes a sequencing process that involves incorporating oligomers by polymerization with a polymerase. A modification of the Sanger method, with end-terminated oligomers as substrates, is used to build sequencing ladders by gel electrophoresis or capillary chromatography. While coupling of oligomers by end ligation is well known, the use of a polymerase to couple oligomers in a template-directed process was utilized to new advantage.

Polymerization techniques are expected to grow in power as modified polymerases (and ligases) become available through genetic engineering and bioprospecting, and methods for elimination of exonuclease activity by polymerase modification are already known. For example, Published U.S. Patent Application 2007/0048748 to Williams describes the use of mutant polymerases for incorporating dye-labeled and other modified nucleotides. Substrates for these polymerases also include γ-phosphate labeled nucleotides. Both increased speed of incorporation and reduction in error rate were found with chimeric and mutant polymerases.

In addition, a large effort has been made by both academic and industrial teams to sequence native DNA using non-synthetic methods. For example, Agilent Technologies, Inc. along with university collaborators are developing a single molecule detection method that threads the DNA through a nanopore to make measurements as it passes through. As with Visigen and LingVitae, this method must overcome the problem of efficiently and accurately obtaining distinct signals from individual nucleobases separated by sub-nanometer dimensions, as well as the problem of developing reproducible pore sizes of similar size. As such, direct sequencing of DNA by detection of its constituent parts has yet to be achieved in a high-throughput process due to the small size of the nucleotides in the chain (about 4 Angstroms center-to-center) and the corresponding signal to noise and signal resolution limitations therein. Direct detection is further complicated by the inherent secondary structure of DNA, which does not easily elongate into a perfectly linear polymer.

Methods which overcome the spatial resolution challenges of high-throughput DNA sequencing have been disclosed in Published PCT Applications WO 2008/157696 and WO 2009/055617. WO 2008/157696 describes a method of sequencing by expansion. A daughter strand comprising internucleotide tethers, reporter groups, and cleavable internucleotide bonds is produced by template directed synthesis. The internucleotide bonds are then cleaved producing an oligomer having a length longer than the length of the target nucleic acid. The longer length of oligomer results in better detection resolution than s possible with the shorter target nucleic acid.

In a related method, WO 2009/055617 discloses a method wherein a daughter strand comprising reporter groups which encode less than the entire genomic sequence of the target nucleic acid is produced by template directed synthesis. The reduced reporter content results in better resolution than that obtained with higher reporter content methods.

While significant advances have been made in the field of DNA sequencing, there continues to be a need in the art for new and improved methods of sequencing DNA and for related methods of detection and presentation of DNA oligomers. The present invention fulfills these needs and provides further related advantages.

BRIEF SUMMARY

In general terms, methods and corresponding devices, products and kits are disclosed that overcome the spatial resolution, presentation, detection, and other challenges presented by existing high throughput nucleic acid sequencing techniques. In one embodiment, this is achieved by either encoding all the base sequence information of a target nucleic acid on a first surrogate polymer (referred to herein as an "Xpandomer") or encoding only a subset of the base sequence information of the target nucleic acid on a second surrogate polymer (referred to herein as an "S-Xpandomer"). The surrogate polymers (Xdaughter strands and S-Xdaughter strands, respectively) are of extended length making them easier to detect. The Xpandomers and S-Xpandomers are formed by template dependent replication of a DNA target in which a plurality of subunits (referred to herein as Xmers and S-Xmers, respectively) are serially connected. Such synthesis preserves the original genetic information of the target nucleic acid, while also increasing linear separation of the individual elements of the sequence data.

In one embodiment, a method is disclosed for sequencing a target nucleic acid, comprising: a) providing a Xdaughter strand produced by a template-directed synthesis, the daughter strand comprising a plurality of subunits coupled in a sequence corresponding to a contiguous nucleotide sequence of all or a portion of the target nucleic acid, wherein the individual subunits comprise a tether, at least one probe or nucleobase residue, and at least one selectively cleavable bond; b) cleaving the at least one selectively cleavable bond to yield an Xpandomer of a length longer than the plurality of the subunits of the daughter strand, the Xpandomer comprising the tethers and reporter elements for parsing genetic information in a sequence corresponding to the contiguous nucleotide sequence of all or a portion of the target nucleic acid; and c) detecting the reporter elements of the Xpandomer.

Examples of specific embodiments as well as methods of making and using Xpandomers are disclosed in more in detail in Published PCT WO2008/157696.

In another embodiment, a method is provided for sequencing a target nucleic acid, comprising:

a) providing an S-Xdaughter strand produced by a template-directed synthesis, the daughter strand comprising a plurality of subunits coupled in a sequence corresponding to a contiguous nucleotide sequence of all or a portion of the target nucleic acid, wherein the individual subunits comprise a tether, at least one probe, and at least one selectively cleavable bond, the at least one probe comprising X nucleobase residues (with X being a positive integer greater than one) and at least one reporter construct that encodes the genetic information of Y nucleobase residue(s) of the probe (with Y being a positive integer less than X);

b) cleaving the at least one selectively cleavable bond to yield an S-Xpandomer of a length longer than the plurality of the subunits of the S-Xdaughter stand, the S-Xpandomer comprising the tethers and reporter elements for determining Y nucleobase(s) every X nucleobases; and c) detecting the at least one reporter construct to decode the genetic information of Y nucleobase(s) every X nucleobases of the daughter strand.

Since Y is less than X, only a fraction of the nucleotide bases of the target nucleic acid are detected. For example, and for illustration only, when X is 4 and Y is 1, the reporter constructs are detected to determine 1 nucleobase every 4 nucleobases of the daughter strand. Since the daughter strand comprises a plurality of subunits coupled in a sequence corresponding to a contiguous nucleotide sequence of all or a portion of the target nucleic acid, 1 of every 4 nucleobases of the target nucleic acid is sequenced. In many instance, detection of "Y of every X" nucleobases (e.g., 1 of every 4, or every $4^{th}$, nucleobase) in the target nucleic acid is sufficient for sequencing purposes. Alternatively, and if desired, template-dependent replication of the target nucleic acid using a plurality (e.g., library) of probe constructs may be employed to produce additional S-Xpandomers for detection, thus identifying the remaining interlaced target nucleobases in a similar manner.

In a further embodiment of the above method, the target nucleic acid is produced by a template-directed rolling circle polymerization process.

In other further embodiments, the template directed synthesis comprises a ligation reaction. For example, the ligation reaction may comprise an enzymatic ligation reaction.

In yet other further embodiments, the at least one reporter construct is associated with:
the tethers of the S-Xpandomer;
the S-Xdaughter strand prior to cleavage of the at least one selectively cleavable bond; or
the S-Xpandomer after cleavage of the at least one selectively cleavable bond.

In further embodiments, the at least one reporter construct is attached to the S-Xdaughter strand after template-directed synthesis thereof.

In other further embodiments, the tether is attached to the S-Xdaughter strand after template-directed synthesis thereof.

In other further embodiments, the S-Xpandomer further comprises all or a portion of the at least one probe. For example, in one embodiment, the at least one reporter construct is or is associated with the at least one probe.

The S-Xpandomer comprises a plurality of subunits coupled in a sequence corresponding to a contiguous nucleotide sequence of all or a portion of the target nucleic acid. Thus, in a further embodiment, the S-Xpandomer comprises the following structure:

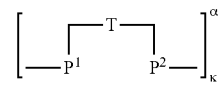

wherein
T represents the tether;
$P^1$ represents a first probe moiety;
$P^2$ represents a second probe moiety;
κ represents the $κ^{th}$ subunit in a chain of m subunits, where m is an integer greater than three; and
α represents a species of a subunit motif selected from a library of subunit motifs, wherein each of the species comprises sequence information of the contiguous nucleotide sequence of a portion of the target nucleic acid;

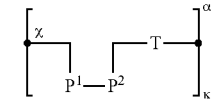

wherein
T represents the tether;
$P^1$ represents a first probe moiety;
$P^2$ represents a second probe moiety;
κ represents the $κ^{th}$ subunit in a chain of m subunits, where m is an integer greater than three;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit;

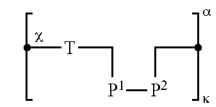

wherein
T represents the tether;
$P^1$ represents a first probe moiety;
$P^2$ represents a second probe moiety;
κ represents the $κ^{th}$ subunit in a chain of m subunits, where m is an integer greater than three;

α represents a species of a subunit motif selected from a library of subunit motifs, wherein each of the species comprises sequence information of the contiguous nucleotide sequence of a portion of the target nucleic acid; and χ represents a bond with the tether of an adjacent subunit;

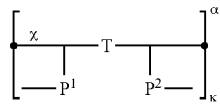

wherein

T represents the tether;
P$^1$ represents a first probe moiety;
P$^1$ represents a second probe moiety;
κ represents the κ$^{th}$ subunit in a chain of m subunits, where m is an integer greater than three;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit;

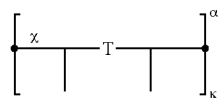

wherein

T represents the tether;
κ represents the κ$^{th}$ subunit in a chain of m subunits, where m is an integer greater than three;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit;

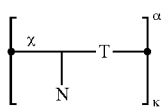

wherein

T represents the tether;
N represents a nucleobase residue;
κ represents the κ$^{th}$ subunit in a chain of m subunits, where m is an integer greater than ten;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit;

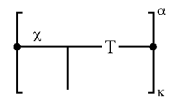

wherein

T represents the tether;
κ represents the κ$^{th}$ subunit in a chain of m subunits, where m is an integer greater than ten;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit;

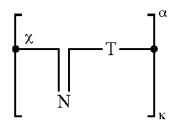

wherein

T represents the tether;
N represents a nucleobase residue;
κ represents the κ$^{th}$ subunit in a chain of m subunits, where m is an integer greater than ten;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit;

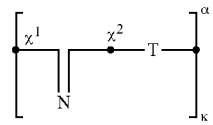

wherein

T represents the tether;
N represents a nucleobase residue;
κ represents the κ$^{th}$ subunit in a chain of m subunits, where m is an integer greater than ten;
α represents a species of a subunit motif selected from a library of subunit motifs, wherein each of the species comprises sequence information of the contiguous nucleotide sequence of a portion of the target nucleic acid;
χ$^1$ represents a bond with the tether of an adjacent subunit; and
χ$^2$ represents an inter-tether bond; or

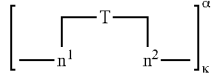

wherein

T represents the tether;

$n^1$ and $n^2$ represents a first portion and a second portion, respectively, of a nucleobase residue;

κ represents the $κ^{th}$ subunit in a chain of m subunits, where m is an integer greater than ten; and α represents a species of a subunit motif selected from a library of subunit motifs, wherein each of the species comprises sequence information of the contiguous nucleotide sequence of a portion of the target nucleic acid.

In a further embodiment, the S-Xdaughter strand is formed from a plurality of oligomer substrate constructs having the following structure:

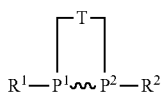

wherein

T represents the tether;

$P^1$ represents a first probe moiety;

$P^2$ represents a second probe moiety;

~ represents the at least one selectively cleavable bond; and $R^1$ and $R^2$ represent the same or different end groups for the template directed synthesis of the daughter strand;

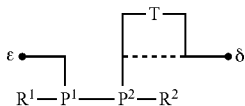

wherein

T represents the tether;

$P^1$ represents a first probe moiety;

$P^2$ represents a second probe moiety;

$R^1$ and $R^2$ represent the same or different end groups for the template directed synthesis of the daughter strand;

ε represents a first linker group;

δ represents a second linker group; and

"- - - -" represents a cleavable intra-tether crosslink;

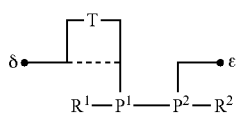

wherein

T represents the tether;

$P^1$ represents a first probe moiety;

$P^2$ represents a second probe moiety;

$R^1$ and $R^2$ represent the same or different end groups for the template directed synthesis of the daughter strand;

ε represents a first linker group;

δ represents a second linker group; and

"- - - -" represents a cleavable intra-tether crosslink;

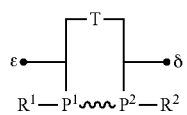

wherein

T represents the tether;

$P^1$ represents a first probe moiety;

$P^2$ represents a second probe moiety;

~ represents the at least one selectively cleavable bond;

$R^1$ and $R^2$ represent the same or different end groups for the template directed synthesis of the daughter strand;

ε represents a first linker group; and

δ represents a second linker group;

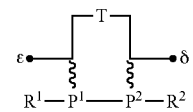

wherein

T represents the tether;

$P^1$ represents a first probe moiety;

$P^2$ represents a second probe moiety;

~ represents the at least one selectively cleavable bond;

$R^1$ and $R^2$ represent the same or different end groups for the template directed synthesis of the daughter strand;

ε represents a first linker group; and

δ represents a second linker group;

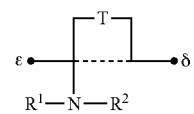

wherein

T represents the tether;

N represents a nucleobase residue;

$R^1$ and $R^2$ represent the same or different end groups for the template directed synthesis of the daughter strand;

ε represents a first linker group;

δ represents a second linker group; and

"- - - -" represents a cleavable intra-tether crosslink;

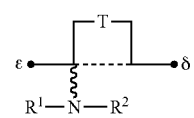

wherein

T represents the tether;

N represents a nucleobase residue;

$R^1$ and $R^2$ represent the same or different end groups for the template directed synthesis of the daughter strand;

~ represents the at least one selectively cleavable bond;

ε represents a first linker group;

δ represents a second linker group; and

"- - - -" represents a cleavable intra-tether crosslink;

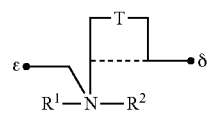

wherein
T represents the tether;
N represents a nucleobase residue;
$R^1$ and $R^2$ represent the same or different end groups for the template directed synthesis of the daughter strand;
$\epsilon$ represents a first linker group;
$\delta$ represents a second linker group; and
"- - - -" represents a cleavable intra-tether crosslink;

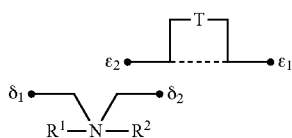

wherein
T represents the tether;
N represents a nucleobase residue;
$R^1$ and $R^2$ represent the same or different end groups for the template directed synthesis of the daughter strand;
$\epsilon_1$ and $\epsilon_2$ represent the same or different first linker groups;
$\delta_1$ and $\delta_2$ represent the same or different second linker groups; and
"- - - -" represents a cleavable intra-tether crosslink; or

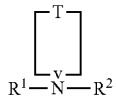

wherein
T represents the tether;
N represents a nucleobase residue;
V represents an internal cleavage site of the nucleobase residue; and
$R^1$ and $R^2$ represent the same or different end groups for the template directed synthesis of the daughter strand.

In some further embodiments, $R^1$ and $R^2$ are selected from hydroxyl, phosphate, and triphosphate.

In other further embodiments, the target nucleic acid is produced by a rolling circle polymerization process.

In another embodiment, the present disclosure provides a method for sequencing a target nucleic acid, the method comprising:
a) providing a paired-end daughter strand produced by a bidirectional template-directed synthesis, the paired-end daughter strand comprising a first and second sequence region joined to a first and second end of a primer region, respectively, each sequence region independently comprising at least 10 nucleobase residues coupled in a sequence corresponding to a contiguous nucleotide sequence of all or a portion of the target nucleic acid;
b) using the paired-end daughter strand as the analyte input to sequence at least 10 nucleobase residues of each of the first and second probe regions to decode the genetic information of the target nucleic acid.

In further embodiments of the foregoing, the bidirectional template-directed synthesis comprises a ligation reaction. For example, in some embodiments, the ligation reaction is an enzymatic ligation reaction. In other embodiments, the bidirectional template-directed synthesis comprises a polymerase reaction from the 3' end of the primer region.

In other embodiments, the present disclosure provides a method for sequencing a target nucleic acid, the method comprising:
a) providing a surrogate polymer paired-end daughter strand produced by a bidirectional template-directed synthesis, the surrogate polymer paired-end daughter strand having a first and second probe region joined to a first and second end of a primer region, respectively, the first and second probe regions comprising a plurality of surrogate polymer substrates coupled in a sequence corresponding to a contiguous nucleotide sequence of all or a portion of the target nucleic acid, wherein the individual surrogate polymer substrates comprise a tether, at least one probe, and at least one selectively cleavable bond, the individual probe comprising X nucleobase residues (with X being a positive integer greater than one) and at least one reporter element that encodes Y nucleobase residue(s) (with Y being a positive integer of at least one and up to a maximum of X);
b) cleaving the at least one selectively cleavable bond to yield a paired-end surrogate polymer of a length longer than the plurality of the surrogate polymer substrates of the daughter stand, the paired-end surrogate polymer comprising the tethers and reporter elements for determining Y nucleobase(s) every X nucleobases; and
c) detecting the reporter elements to determine Y nucleobase(s) every X nucleobases of the paired-end daughter strand.

In further embodiments of the foregoing, the bidirectional template-directed synthesis comprises a ligation reaction. For example, in some embodiments, the ligation reaction is an enzymatic ligation reaction. In other embodiments, the bidirectional template-directed synthesis comprises a polymerase reaction from the 3' end of the primer region.

In other embodiments, the present disclosure provides a method for producing a paired-end nucleic acid comprising a first and second region joined to a first and second end of a primer region, respectively, wherein the first and second regions independently comprise at least 4 oligonucleotides, the method comprising:
a) providing a primer adapter, wherein the primer adapter comprises a region complementary, or near complementary, to a primer;
b) providing the primer, wherein the primer comprises a 5' phosphate end and a 3' hydroxyl end;
c) duplexing the primer to the primer adapter; and
d) extending the primer from both the 5' end and the 3' end, wherein extending comprises ligating at least 4 oligonucleotides to the 5' end of the primer.

In other embodiments of the foregoing, the paired-end nucleic acid is a paired-end surrogate polymer daughter strand, and the nucleotides or oligonucleotides comprise Xprobes or S-Xprobes. In other embodiments, the primer adapter circularizes a target nucleic acid. In yet other embodiments, the primer adapter further comprises a tether, wherein the tether is optionally attached to a solid substrate. In yet other embodiments, ligating comprises an enzymatic ligation reaction. In other embodiments, extending the primer further comprises ligating from the 3' end of the primer. In yet other embodiments, extending the primer further comprises a polymerase reaction extending from the 3' end of the primer.

In other embodiments, the present disclosure provides a paired-end surrogate polymer comprising a first probe region and a second probe region, the first and second probe regions joined to a first and second end of a primer region, respectively, the first and second probe regions comprising a plurality of subunits coupled in a sequence corresponding to a contiguous nucleotide sequence of all or a portion of a target nucleic acid. In some embodiments, the paried-end surrogate polymer is produced by the method described above. In other embodiments, the first and second probe regions independently comprise 4 or more probes.

The present disclosure also provides a kit comprising a plurality of constructs (i.e., either Xmers or S-Xmers with the appropriate R1/R2 end groups) for forming a surrogate polymer daughter strand by a template-directed synthesis, wherein the kit optionally comprises appropriate instructions for use of the same in forming a surrogate polymer daughter strand. In some embodiments, the kit comprises from 10 to 65000 unique members.

In other embodiments, the present disclosure provides a method of reading individual reporter elements of a surrogate polymer, comprising:

a) providing a surrogate polymer, wherein the surrogate polymer comprises one or more individual reporter elements;

b) providing a detector construct;

b) presenting the surrogate polymer to the detector construct;

c) reading the individual reporter elements sequentially to determine the reporter element sequence; and d) using the reporter sequence thus determined to decode the genetic information of the surrogate polymer.

In some embodiments of the foregoing, the detector construct comprises a first and a second reservoir comprising first and second electrodes, respectively, wherein the first and second reservoirs are separated by a nanopore substrate positioned between the first and second reservoirs, the nanopore substrate comprising at least one nanopore channel, and reading the individual reporter elements comprises translocating the surrogate polymer from the first reservoir to the second reservoir through the at least one nanopore channel. In other embodiments, reading the individual reporter elements further comprises measuring the impedance change in the nanopore channel as the surrogate polymer translocates through the nanopore channel.

In further embodiments, the individual reporter elements comprise at least one FRET (Fluorescence Resonance Energy Transfer) donor or acceptor fluorophore and the nanopore channel comprises at least one FRET donor or acceptor fluorophore, provided that when the individual reporter elements comprise a FRET donor, the nanopore channel comprises a FRET acceptor, and when the individual reporter elements comprise a FRET acceptor, the nanopore channel comprises a FRET donor, and reading the individual reporter elements further comprises:

a) exciting the donor fluorophores with a light source as the surrogate polymer translocates the nanopore channel; and b) detecting a fluorescent signal emitted from the acceptor fluorophores.

In other embodiments of the foregoing, the donor fluorophores comprise 1 to 4 excitation wavelengths.

In further embodiments, the detector construct comprises a nanocomb detector array having at least one detector element in, or at the end of, the nanocomb slot, and reading the individual reporter elements comprises passing the surrogate polymer through the end of the nanocomb slot. In some other embodiments, the nanocomb detector array further comprises a first and a second electrode, and the surrogate polymer is passed between the first and the second electrodes. In yet other embodiments, the individual reporter elements induce a change in electrolyte current as the surrogate polymer passes between the first and the second electrodes. In still other embodiments, the individual reporter elements form a current path between the first and the second electrodes as the surrogate polymer passes between the first and the second electrodes.

In other further embodiments, the surrogate polymer is presented to the detector construct as a linearized array, wherein the linearized array comprises a substrate. In some other embodiments, reading the individual reporter elements comprises electron beam microscopy, wherein the electron beam forms a line. In other embodiments, the individual reporter elements comprise boron or nanogold. In another embodiment, the substrate comprises a contrast coating for improved signal-to-noise ratio.

In other further embodiments of the foregoing, the detector construct comprises at least one knife-edge electrode, the individual reporter elements comprise conductive polymeric bristles, and reading the individual reporter elements comprises:

a) applying an electric potential between the at least one knife-edge electrode and the substrate; and b) measuring an electric current as the surrogate polymer passes under the at least one knife-edge electrode.

In some other embodiments of the foregoing, the substrate comprises a conductive film. In some embodiments, the conductive polymeric bristles comprise polymers selected from polyacetylene, polyaniline, or polypyrrole.

In other further embodiments, the individual reporter elements comprise at least one fluorophore, wherein the at least one fluorophore comprises at least one spectral type, and reading the individual reporter elements comprises:

a) providing an excitation energy, localizing the excitation energy to excite the at least one fluorophore of the individual reporter elements; and b) detecting a fluorescent signal emitted by the at least one fluorophore.

In some embodiments of the foregoing, the excitation energy is from a near field source, the near field source emerging from a slit, and reading the individual reporter elements further comprises:

a) moving the slit parallel to the surrogate polymer; and b) detecting the fluorescent signal of the at least one fluorophore of the individual reporter elements.

For example, in some embodiments, the fluorescent signal is detected in the far field.

In other embodiments, the present disclosure provides a method of detecting an analyte, comprising:

a) providing at least one analyte;

b) providing at least one indicator moiety, wherein the indicator moiety is not associated with the analyte;

c) providing a detector construct, wherein the detector construct comprises a first and a second reservoir comprising first and second electrodes, respectively, wherein the first and second reservoirs are separated by a nanopore substrate positioned between the first and second reservoirs;

d) providing an electric potential to the first and second electrodes, wherein the electric potential is sufficient to translocate the at least one analyte and the at least one indicator moiety through the at least one nanopore channel; and c) detecting a change in an optical signal emitted from the at least one indicator moiety at or near the at least one nanopore channel as the at least one analyte translocates through the at least one nanopore channel.

In some embodiments, the foregoing method further comprises providing an excitation wavelength, wherein the excitation wavelength is sufficient to induce a fluorescent signal from the at least one indicator moiety. In other embodiments, the at least one analyte is a nucleic acid. In yet other embodiments, the at least one analyte is a surrogate polymer. In some other embodiments, the at least one nanopore comprises a nanopore array, and the nanopore array shares the first and second reservoirs.

In further embodiments, the at least one indicator moiety is a fluorophore, the first reservoir comprises a high concentration of the fluorophores relative to the second reservoir, and detecting a change in optical signal further comprises detecting a change in fluorescent signal as the fluorophores translocate through the at least one nanopore channel. In some embodiments, epifluorescence microscopy is used for detecting the change in fluorescent signal. In other embodiments, conoscopy is used for detecting the change in fluorescent signal. In other embodiments, the nanopore substrate comprises a blocking film. In yet other embodiments, the fluorophores are fluoroscein. In some other embodiments, the second reservoir comprises a fluorescence quenching agent, and detecting a change in optical signal further comprises detecting a change in fluorescent signal as the fluorophores or the quenching agent translocate through the at least one nanopore channel. For example, in some embodiments, the quenching agent is selected from QSY®7, QSY®9, and free radicals.

In some further embodiments, the method further comprises providing two indicator moieties, wherein a first indicator moiety is selected from indicator ions, a second indicator moiety is selected from fluorescence indicators, the first reservoir comprises indicator ions, the second reservoir comprises fluorescence indicators, and detecting a change in an optical signal further comprises detecting the change in fluorescence signal emitted as either the indicator ions or the indicator moiety pass through the at least one nanopore channel. In some other embodiments, the second reservoir further comprises a non-fluorescing absorber. In yet other embodiments, the nanopore channel is masked to create a circular opening of about 1 μm in diameter, wherein the opening is concentric with the nanopore channel. In other embodiments, the indicator ions are selected from calcium ions, singlet hydrogen ions, singlet oxygen ions, potassium ions, zinc ions, magnesium ions, chlorine ions, and sodium ions. In some embodiments, the fluorescence indicator is selected from Fura-3, Fluo-3, Indo-1, and Fura Red. In other embodiments, the fluorescence indicator is a fluorescence quencher. In yet other embodiments, the first reservoir comprises iodide ions and the second reservoir comprises fluorescein.

In some further embodiments, the method further comprises providing two indicator moieties, wherein the first reservoir comprises a first indicator moiety and the second reservoir comprises a second indicator moiety, wherein the first and second indicator moieties are capable of combining to form a third indicator moiety in an excited state, and detecting a change in optical signal further comprises detecting photons which are emitted when the third indicator moiety relaxes to a ground state.

In other embodiments a method of presenting at least one surrogate polymer for detection is provided, wherein the method comprises:
  a) providing a detector construct, wherein the detector construct comprises at least one detector element;
  b) providing the at least one surrogate polymer, wherein the at least one surrogate polymer comprises one or more individual reporter elements; and
  c) processing the at least one surrogate polymer to obtain a uniform spatial and temporal spacing of the one or more individual reporter elements.

In other embodiments, the detector construct comprises at least one nanopore channel. For example, in some embodiments, the detector construct comprises a regular array of nanopore channels. In other embodiments, processing the at least one surrogate polymer comprises tethering an end of the at least one surrogate polymer to a solid substrate having at least one binding site. In yet other embodiments, processing the at least one surrogate polymer comprises aligning the at least one surrogate polymer on a substrate surface.

In another further embodiment, processing the at least one surrogate polymer comprises attaching a charged, linear polymer having a low molecular weight to an end of the at least one surrogate polymer. For example, in one embodiment the charged, linear polymer is selected from polyglutamic acid and polyphosphate.

In another further embodiment, processing the at least one surrogate polymer comprises applying a voltage to the at least one nanopore channel, wherein the voltage is higher than a desired measurement voltage, and decreasing the voltage to the desired measurement voltage when a surrogate polymer is detected in the nanopore channel. In another embodiments of the foregoing, the voltage is manipulated such that only one surrogate polymer may occupy the at least one nanopore channel at a time.

In yet another further embodiment, processing the at least one surrogate polymer comprises attaching a stop to an end of the at least one surrogate polymer, wherein the stop prevents the at least one surrogate polymer from passing through the at least one nanopore channel and prevents multiple surrogate polymers from occupying the same nanopore channel, and prefilling the at least one surrogate polymer in the at least one nanopore channel. In some embodiments, the stop is selected from a bulky dendrimer and a bead, for example, a magnetic bead.

In other further embodiments, processing the at least one surrogate polymer comprises attaching a linear ferrite polymer to an end of the at least one surrogate polymer and manipulating a magnetic field and an electric field to obtain a uniform spatial and temporal spacing of the one or more individual reporter elements. For example, in one embodiment, the magnetic field and the electric field are manipulated such that only one surrogate polymer may occupy the at least one nanopore channel at a time.

In another further embodiment, processing the at least one surrogate polymer comprises controlling the flow of the at least one surrogate polymer toward the detector construct. For example, in one embodiment, controlling the flow of the at least one surrogate polymer comprises tethering the surrogate polymer to a substrate, wherein the tether comprises an addressable, cleavable linkage, and selectively cleaving the linkage such that one surrogate polymer is released from the substrate per unit of time. In one embodiment, selectively cleaving the cleavable linkage comprises controlling the cleavage rate such that only one surrogate polymer may occupy the at least one detector element at a time. In some embodiments, the linkage is selected from photocleavable linkages, thermally cleavable linkages and electrochemically cleavable linkage.

In further embodiments, controlling the flow of the at least one surrogate polymer comprises:
  a) providing at least one gating construct, wherein the at least one gating construct comprises a first, second, and third electrode; and
  b) manipulating an electric field applied independently to the first, second, and third electrodes to obtain a uniform spatial and temporal spacing of the one or more individual reporter elements.

In other embodiments of the foregoing, the electric field is manipulated such that only one surrogate polymer may occupy the at least one detector element at a time.

In yet other further embodiments, controlling the flow of the at least one surrogate polymer comprises:

a) providing at least one gating construct, wherein the at least one gating construct comprises a first and second porous electrode and a gating element, wherein the first and second porous electrodes are affixed to a first and second side of the gating element, respectively;

b) applying an electric field to the first and second electrodes; and c) transporting the at least one surrogate polymer through the gate toward the at least one detector element.

In other embodiments of the foregoing, the gating element is selected from a porous membrane and a nanohole. In some embodiments, the electric field is manipulated to obtain a uniform spatial and temporal spacing of the one or more individual reporter elements. In other embodiments, the electric field is manipulated such that only one surrogate polymer may occupy the at least one detector element at a time. In some embodiments, the gating element is a porous membrane. For example, in some embodiments, the porous membrane comprises pores from about 20 nm to about 100 nm in diameter. In other embodiments, the porous membrane is selected from aluminum oxide and a polymer track-formed membrane. In other embodiments, a multiplexed gating construct is provided (i.e. more than one gating construct is provided).

In other further embodiments, the flow of the at least one surrogate polymer comprises providing at least one gating construct selected from an affinity gel or a channel (e.g. aluminum oxide), and processing the at least one surrogate polymer comprises:

a) attaching an affinity drag tag to an end of the surrogate polymer; and b) applying an electric field sufficient to translocate the surrogate polymer through the gating construct toward the at least one detector element.

In other further embodiments of the foregoing, the electric field is manipulated to obtain a uniform spatial and temporal spacing of the one or more individual reporter elements. In yet other embodiments, the electric field is manipulated such that only one surrogate polymer may occupy the at least one detector element at a time. In some embodiments, the gating construct is an affinity gel.

In other further embodiments, the solid substrate has uniformly spaced binding sites. In some embodiments, the binding sites are a spot about 1 μm in size. In other embodiments, a maximum of one surrogate polymer binds to each individual binding site. In even other embodiments, the surrogate polymer further comprises a dendrimer attached to the end of the surrogate polymer, wherein the dendrimer sterically inhibits binding of another surrogate polymer to the same binding site. In other embodiments, the solid substrate is selected from flexible polyethylene terephthalate (PET) film, float glass, a silicon wafer, and stainless steel. In even other embodiments, the at least one binding site comprises a line on the solid substrate. For example, in some embodiments, the width of the line is less than the distance between the surrogate polymers bound thereto.

In other further embodiments, the substrate, having at least one surrogate polymer bound thereto, is rotated from normal to 180 degrees to an applied electric field, the electric field causing the at least one surrogate polymer to lie down in a straight and elongated orientation on the surface of the substrate. In some embodiments, the at least one surrogate polymer is further attached to the substrate surface in a laid down, straight and elongated orientation. For example, in some embodiments, the at least one surrogate polymer is attached to the substrate surface by ultraviolet or chemical activation of the substrate surface. In other embodiments, the solid substrate is a flexible polyethylene terephthalate (PET) film.

In further embodiments, the substrate, having at least one surrogate polymer bound thereto, is passed through a comb construct, wherein the comb construct comprises a stretching electric field at an input side, a pinning electric field at an output side, and a comb element between the input and output sides, and processing the at least one surrogate polymer further comprises passing the substrate through the stretching electric field, under the comb, and through the electric pinning field such that the at least one surrogate polymer is laid down in a straight and elongated orientation on the substrate surface. In some embodiments, the at least one surrogate polymer is further attached to the substrate surface in a laid down, straight and elongated orientation. For example, in some embodiments, the at least one surrogate polymer is attached to the substrate surface by application of an electric filed or by ultraviolet or chemical activation of the substrate surface.

In other further embodiments, the substrate, having at least one surrogate polymer bound thereto, is passed under a brush construct, wherein the brush construct comprises bristles, the bristles causing the at least one surrogate polymer to lay down in a straight and elongated orientation on the substrate surface. In other embodiments, the at least one surrogate polymer is further attached to the substrate surface in a laid down, straight and elongated orientation. For example, in some embodiments, the at least one surrogate polymer is attached to the substrate surface by application of an electric field or by ultraviolet or chemical activation of the substrate surface. In other embodiments, the bristles are about 10 nm in diameter. In yet other embodiments, the bristles comprise polymers, for example ultraviolet cured or thermal cured polymers.

In further embodiments, the substrate comprises a closed loop of flexible film, and processing the at least one surrogate polymer further comprises a continuous process comprising:

a) rotating the substrate through the detector construct;

b) removing the at least one surrogate polymer from the substrate surface after it passes through the detector element;

c) reattaching another surrogate polymer to the substrate surface;

d) and repeating steps a and b until all surrogate polymers are analyzed.

In other embodiments of the foregoing, the substrate is a flexible polyethylene terephthalate (PET) film.

In yet other further embodiments, processing the at least one surrogate polymer comprises affixing the at least one surrogate polymer to a solid substrate comprising nanopore channels, wherein affixing the at least one surrogate polymer to the solid substrate comprises attaching a stop to an end of the at least one surrogate polymer, wherein the stop prevents the at least one surrogate polymer from passing through the at least one nanopore channel and prevents multiple surrogate polymer from occupying the same nanopore channel, and prefilling the at least one surrogate polymer in the at least one nanopore channel. For example, in some embodiments, the stop is selected from a bulky dendrimer and a bead. In other embodiments, the bead is a magnetic bead.

These and other aspects of the invention will be apparent upon reference to the attached drawings and following detailed description. To this end, various references are set forth herein which describe in more detail certain procedures, compounds and/or compositions, and are hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIGS. 1A and 18 illustrate the limited separation between nucleobases that must be resolved in order to determine the sequence of nucleotides in a nucleic acid target.

FIGS. 15A, 15B, and 15C illustrate different methods for presenting nucleic acid polymers for detection.

FIG. 22C is an end view of a comb.

FIGS. 24A through 24D are gels of ligation experiments.

DETAILED DESCRIPTION

Figure 2A:
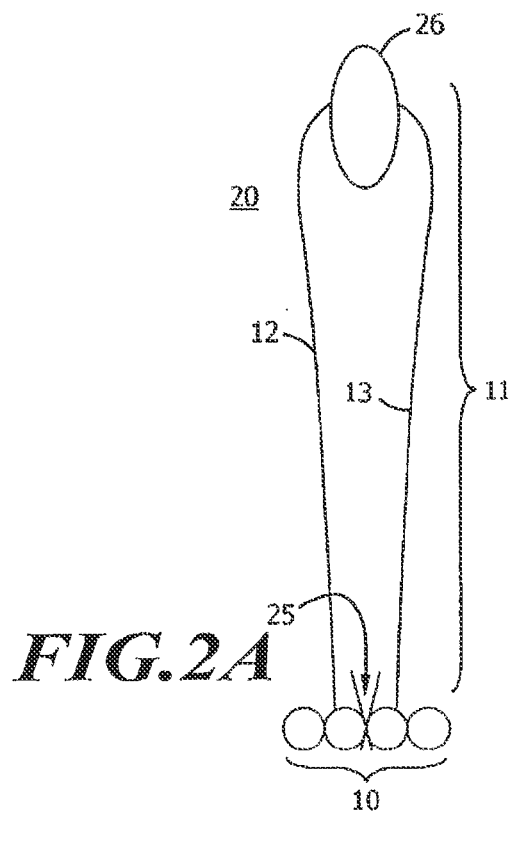
FIGS. 2A through 2D illustrate schematically several representative structures of substrates useful in the invention.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Definitions

As used herein, and unless the context dictates otherwise, the following terms have the meanings as specified below.

"SBX" refers to Sequence by Expansion. SBX processes and methods are described in detail herein.

"Nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyndine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, LO), all herein incorporated by reference in their entireties.

"Nucleobase residue" includes nucleotides, nucleosides, fragments thereof, and related molecules having the property of binding to a complementary nucleotide. Deoxynucleotides and ribonucleotides, and their various analogs, are contemplated within the scope of this definition. Nucleobase residues may be members of oligomers and probes. "Nucleobase" and "nucleobase residue" may be used interchangeably herein and are generally synonymous unless context dictates otherwise.

"Polynucleotides", also called nucleic acids or nucleic acid polymers, are covalently linked series of nucleotides. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound, including the surrogate polymers disclosed herein, having a linear backbone of nucleotides. Oligonucleotides, also termed oligomers, are generally shorter chained polynucleotides.

"Complementary" generally refers to specific nucleotide duplexing to form canonical Watson-Crick base pairs, as is understood by those skilled in the art. However, complementary as referred to herein also includes base-pairing of nucleotide analogs, which include, but are not limited to, 2'-deoxyinosine and 5-nitroindole-2'-deoxyriboside, which are capable of universal base-pairing with A, T, G or C nucleotides and locked nucleic acids, which enhance the thermal stability of duplexes. One skilled in the art will recognize that hybridization stringency is a determinant in the degree of match or mismatch in the duplex formed by hybridization.

"Nucleic acid" is a polynucleotide or an oligonucleotide. A nucleic acid molecule can be deoxyribonucleic acid (DNA), ribonucleic acid (RNA), or a combination of both. Nucleic acids are generally referred to as "target nucleic acids" or "target sequence" if targeted for sequencing. Nucleic acids can be mixtures or pools of molecules targeted for sequencing.

"Probe" is a short strand of nucleobase residues, referring generally to two or more contiguous nucleobase residues which are generally single-stranded and complementary to a target sequence of a nucleic acid. As embodied in "Substrate Members" and "Substrate Constructs", probes can be up to 20 nucleobase residues in length. Probes may include modified nucleobase residues and modified intra-nucleobase bonds in any combination. Backbones of probes can be linked together by any of a number of types of covalent bonds, including, but not limited to, ester, phosphodiester, phosphoramide, phosphonate, phosphorothioate, phosphorothiolate, amide bond and any combination thereof. The probe may also have 5' and 3' end linkages that include, but are not limited to, the following moieties: monophosphate, triphosphate, hydroxyl, hydrogen, ester, ether, glycol, amine, amide, and thioester.

"Selective hybridization" refers to specific complementary binding. Polynucleotides, oligonucleotides, probes, nucleobase residues, and fragments thereof selectively hybridize to target nucleic acid strands, under hybridization and wash conditions that minimize nonspecific binding. As known in the art, high stringency conditions can be used to achieve selective hybridization conditions favoring a perfect match. Conditions for hybridization such as salt concentration, temperature, detergents, PEG, and GC neutralizing agents such as betaine can be varied to increase the stringency of hybridization, that is, the requirement for exact matches of C to base pair with G, and A to base pair with T or U, along a contiguous strand of a duplex nucleic acid.

"Template-directed synthesis", "template-directed assembly", "template-directed hybridization", "template-directed binding" and any other template-directed processes, refer to a process whereby nucleobase residues or probes bind selectively to a complementary target nucleic acid, and are incorporated into a nascent daughter strand. A daughter strand produced by a template-directed synthesis is complementary to the single-stranded target from which it is synthesized. It should be noted that the corresponding sequence of a target strand can be inferred from the sequence of its daughter strand, if that is known. "Template-directed polymerization" and "template-directed ligation" are special cases of template-directed synthesis whereby the resulting daughter strand is polymerized or ligated, respectively.

"Daughter strand" means a strand produced by a template-directed synthesis which is complementary to the single-stranded target from which it is synthesized. Daughter strands include Xdaughter strands and S-Xdaughter strands, as defined herein, as well as daughter strands of other nucleic acids.

"Paired-end daughter strand" means a daughter strand produced by a bi-directional synthesis. A paired end daughter strand comprises a first and second sequence region attached to first and second end of a primer. The first and second sequence regions independently comprise nucleobase residues encoding the genetic information of a target nucleic acid. Typically, the first and second sequence regions independently comprise 10 or more decodable nucleobase residues, although paired-end daughter strands having first and second regions comprising less than 10 decodable nucleobase residues are also included with the definition of "paired-end daughter strand". Paired-end daughter strands include Paired-end Xdaughter strands and Paired-end S-Xdaugther strands, as defined herein, as well as Paired-end daughter strands of other nucleic acids.

"Sequence region" means a region of a nucleic acid (surrogate polymer or otherwise) which comprises nucleobase residues coupled in a sequence corresponding to a contiguous nucleotide sequence of all or a portion of a target nucleic acid.

"Not associated with" in the context of an indicator moiety which is not associated with an analyte, means that the indicator moiety is not bonded (e.g. covalent bond, hydrogen bond, etc.) or otherwise conjugated to the analyte.

"Indicator moiety" means a moiety, for example a chemical species, which can be detected under the conditions of a particular assay. Non-limiting examples of indicator moieties include: fluorophores, chemiluminescent species, and any species capable of inducing fluorescence or chemiluminescence in another species.

"Analyte nucleic acid" means a nucleic acid which is the subject of analysis and/or detection. Analyte nucleic acids include surrogate polymers as well as other nucleic acids.

"Primer" means a nucleic acid strand used as a template for template-directed synthesis of a daughter strand.

"Primer adapter" means a nucleic acid strand used as a template to produce a primer.

"Contiguous" indicates that a sequence continues without interruption or missed nucleobase. The contiguous sequence of nucleotides of the template strand is said to be complementary to the contiguous sequence of the daughter strand.

"Substrates" or "substrate members" are oligomers, probes or nucleobase residues that have binding specificity to the target template. The substrates are generally combined with tethers to form substrate constructs. Substrates of substrate constructs that form the primary backbone of the daughter strand are also substrates or substrate members of the daughter strand.

"Substrate constructs" are reagents for template-directed synthesis of daughter strands, and are generally provided in the form of libraries. Substrate constructs generally contain a substrate member for complementary binding to a target template and either a tether member or tether attachment sites to which a tether may be bonded. Substrate constructs are provided in a variety of forms adapted to the invention. Substrate constructs include both "oligomeric substrate constructs" (also termed "probe substrate constructs") and "monomeric substrate constructs" (also termed "nucleobase substrate constructs").

"Subunit motif" or "motif" refers to a repeating subunit of a polymer backbone, the subunit having an overall form characteristic of the repeating subunits, but also having species-specific elements that encode genetic information. Motifs of complementary nucleobase residues are represented in libraries of substrate constructs according to the number of possible combinations of the basic complementary sequence binding nucleobase elements in each motif. If the nucleobase binding elements are four (e.g., A, C, G, and T), the number of possible motifs of combinations of four elements is $4^x$, where x is the number of nucleobase residues in the motif. However, other motifs based on degenerate pairing bases, on the substitution of uracil for thymidine in ribonucleobase residues or other sets of nucleobase residues, can lead to larger libraries (or smaller libraries) of motif-bearing substrate constructs. Motifs are also represented by species-specific reporter constructs, such as the reporters making up a reporter tether. Generally there is a one-to-one correlation between the reporter construct motif identifying a particular substrate species and the binding complementarity and specificity of the motif.

"Xpandomer intermediate" or "S-Xpandomer intermediate" is an intermediate product (also referred to herein as a "Xdaughter strand or S-Xdaugther strand, respectively") assembled from substrate constructs, and is formed by a template-directed assembly of substrate constructs using a target nucleic acid template. Optionally, other linkages between abutted substrate constructs are formed which may include polymerization or ligation of the substrates, tether-to-tether linkages or tether-to-substrate linkages. The Xpandomer intermediate or S-Xpandomer intermediate contains two structures; namely, the constrained Xpandomer or S-Xpandomer and the primary backbone. The constrained Xpandomer or S-Xpandomer comprises all of the tethers in the daughter strand but may comprise all, a portion or none of the substrate as required by the method. The primary backbone comprises all of the abutted substrates. Under the process step in which the primary backbone is fragmented or dissociated, the constrained Xpandomer or S-Xpandomer is no longer constrained and is the Xpandomer or S-Xpandomer product which is extended as the tethers are stretched out. "Duplex daughter strand" refers to an Xpandomer intermediate or S-Xpandomer intermediate that is hybridized or duplexed to the target template.

"Primary backbone" refers to a contiguous or segmented backbone of substrates of the daughter strand. A commonly encountered primary backbone is the ribosyl 5'-3' phosphodiester backbone of a native polynucleotide. However, the primary backbone of an daughter strand may contain analogs of nucleobases and analogs of oligomers not linked by phosphodiester bonds or linked by a mixture of phosphodiester bonds and other backbone bonds, which include, but are not limited to following linkages: phosphorothioate, phosphorothiolate, phosphonate, phosphoramidate, and peptide nucleic acid "PNA" backbone bonds which include phosphono-PNA, serine-PNA, hydroxyproline-PNA, and combinations thereof. Where the daughter strand is in its duplex form (i.e., duplex daughter strand), and substrates are not covalently bonded between the subunits, the substrates are nevertheless contiguous and form the primary backbone of the daughter strand.

"Constrained Xpandomer" or "constrained S-Xpandomer" is an Xpandomer or S-Xpandomer in a configuration before it has been expanded. The constrained Xpandomer or S-Xpandomer comprises all tether members of the daughter strand. It is constrained from expanding by at least one bond or linkage per tether attaching to the primary backbone. During the expansion process, the primary backbone of the daughter strand is fragmented or dissociated to transform the constrained Xpandomer or constrained S-Xpandomer into an Xpandomer or S-Xpandomer, respectively.

"Constrained Xpandomer backbone" or "constrained S-Xpandomer backbone" refers to the backbone of the constrained Xpandomer or constrained S-Xpandomer, respectively. It is a synthetic covalent backbone co-assembled along with the primary backbone in the formation of the daughter strand. In some cases both backbones may not be discrete but may both have the same substrate or portions of the substrate in their composition. The constrained Xpandomer or constrained S-Xpandomer backbone always comprises the tethers whereas the primary backbone comprises no tether members.

"Xpandomer" or "Xpandomer product" is a synthetic molecular construct produced by expansion of a constrained Xpandomer, which is itself synthesized by template-directed assembly of substrate constructs. The Xpandomer is elongated relative to the target template it was produced from. It is composed of a concatenation of subunits, each subunit a motif, each motif a member of a library, comprising sequence information, a tether and optionally, a portion, or all of the substrate, all of which are derived from the formative substrate construct. The Xpandomer is designed to expand to be longer than the target template thereby lowering the linear density of the sequence information of the target template along its length. Xpandomers comprise reporter constructs which comprise all the sequence information of the Xpandomer. In addition, the Xpandomer optionally provides a platform for increasing the size and abundance of reporters which in turn improves signal to noise for detection. Lower linear information density and stronger signals increase the resolution and reduce sensitivity requirements to detect and decode the sequence of the template strand.

"S-Xpandomer" or "S-Xpandomer product" is similar to the Xpandomer defined above, except that S-Xpanomers or S-Xpandomer products comprise reporter constructs which comprise only a portion of the sequence information of the S-Xpandomer. The reduced reporter content allows for reduced resolution requirements.

The term "surrogate polymer" refers to both Xpandomers and S-Xpandomers.

The term "surrogate polymer daughter strand" or surrogate daughter strand" refers to both Xdaughter strands and S-Xdaugther strands.

"Selectively cleavable bond" refers to a bond which can be broken under controlled conditions such as, for example, conditions for selective cleavage of a phosphorothiolate bond, a photocleavable bond, a phosphoramide bond, a 3'-O-B-D-ribofuranosyl-2' bond, a thioether bond, a selenoether bond, a sulfoxide bond, a disulfide bond, deoxyribosyl-5'-3' phosphodiester bond, or a ribosyl-5'-3' phosphodiester bond, as well as other cleavable bonds known in the art. A selectively cleavable bond can be an intra-tether bond or between or within a probe or a nucleobase residue or can be the bond formed by hybridization between a probe and a template strand. Selectively cleavable bonds are not limited to covalent bonds, and can be non-covalent bonds or associations, such as those based on hydrogen bonds, hydrophobic bonds, ionic bonds, pi-bond ring stacking interactions, Van der Waals interactions, and the like.

"Moiety" is one of two or more parts into which something may be divided, such as, for example, the various parts of a tether, a molecule or a probe.

"Tether" or "tether member" refers to a polymer or molecular construct having a generally linear dimension and with an end moiety at each of two opposing ends. A tether is attached to a substrate with a linkage in at least one end moiety to form a substrate construct. The end moieties of the tether may be connected to cleavable linkages to the substrate or cleavable intra-tether linkages that serve to constrain the tether in a "constrained configuration". After the daughter strand is synthesized, each end moiety has an end linkage that couples directly or indirectly to other tethers. The coupled tethers comprise the constrained Xpandomer or S-Xpandomer that further comprises the daughter strand. Tethers have a "constrained configuration" and an "expanded configuration". The constrained configuration is found in substrate constructs and in the daughter strand. The constrained configuration of the tether is the precursor to the expanded configuration, as found in Xpandomer products and S-Xpandomers products. The transition from the constrained configuration to the expanded configuration results from cleavage of selectively cleavable bonds that may be within the primary backbone of the daughter strand or intra-tether linkages. A tether in a constrained configuration is also used where a tether is added to form the daughter strand after assembly of the "primary backbone". Tethers can optionally comprise one or more reporter elements or reporter constructs along its length that can encode sequence information of substrates. The tether provides a means to expand the length of the Xpandomer or S-Xpandomer and thereby lower the sequence information linear density.

"Tether constructs" are tethers or tether precursors composed of one or more tether segments or other architectural components for assembling tethers such as reporter constructs, or reporter precursors, including polymers, graft copolymers, block copolymers, affinity ligands, oligomers, haptens, aptamers, dendrimers, linkage groups or affinity binding group (e.g., biotin).

"Tether element" or "tether segment" is a polymer having a generally linear dimension with two terminal ends, where the ends form end-linkages for concatenating the tether elements. Tether elements may be segments of tether constructs. Such polymers can include, but are not limited to: polyethylene glycols, polyglycols, polypyridines, polyisocyanides, polyisocyanates, poly(triarylmethyl) methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

"Peptide nucleic acid" or "PNA" is a nucleic acid analog having nucleobase residues suitable for hybridization to a nucleic acid, but with a backbone that comprises amino acids or derivatives or analogs thereof.

"Phosphono-peptide nucleic acid" or "pPNA" is a peptide nucleic acid in which the backbone comprises amino acid analogs, such as N-(2-hydroxyethyl)phosphonoglycine or N-(2-aminoethyl)phosphonoglycine, and the linkages between nucleobase units are through phosphonoester or phosphonoamide bonds.

"Serine nucleic acid" or "SerNA" is a peptide nucleic acid in which the backbone comprises serine residues. Such residues can be linked through amide or ester linkages.

"Hydroxyproline nucleic acid" or "HypNA" is a peptide nucleic acid in which the backbone comprises 4-hydroxyproline residues. Such residues can be linked through amide or ester linkages.

"Reporter element" is a signaling element, molecular complex, compound, molecule or atom that is also comprised of an associated "reporter detection characteristic". Reporter elements include, but are not limited to, FRET resonant donor or acceptor, dye, quantum dot, bead, dendrimer, up-converting fluorophore, magnet particle, electron scatterer (e.g., boron), mass, gold bead, magnetic resonance, ionizable group, polar group, hydrophobic group. Still others are fluorescent labels, such as but not limited to, ethidium bromide, SYBR Green, Texas Red, acridine orange, pyrene, 4-nitro-1,8-naphthalimide, TOTO®-1, YOYO®-1, cyanine 3 (Cy3), cyanine 5 (Cy5), phycoerythrin, phycocyanin, allophycocyanin, FITC, rhodamine, 5(6)-carboxyfluorescein, fluorescent proteins, DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (Biological Detection Systems, Inc.), erytrosine, coumaric acid, umbelliferone, texas red rhodaine, tetramethyl rhodamin, Rox, 7-nitrobenzo-1-oxa-1-diazole (NBD), oxazole, thiazole, pyrene, fluorescein or lanthamides; also radioisotopes (such as $^{33}P$, $^{3}H$, $^{14}C$, $^{35}S$, $^{125}I$, $^{32}P$ or $^{131}I$), ethidium, Europium, Ruthenium, and Samarium or other radioisotopes; or mass tags, such as, for example, pyrimidines modified at the C5 position or purines modified at the N7 position, wherein mass modifying groups can be, for examples, halogen, ether or polyether, alkyl, ester or polyester, or of the general type XR, wherein X is a linking group and R is a mass-modifying group, chemiluminescent labels, spin labels, enzymes (such as peroxidases, alkaline phosphatases, beta-galactosidases, and oxidases), antibody fragments, and affinity ligands (such as an oligomer, hapten, and aptamer). Association of the reporter element with the tether can be covalent or non-covalent, and direct or indirect. Representative covalent associations include linker and zero-linker bonds. Included are bonds to the tether backbone or to a tether-bonded element such as a dendrimer or sidechain. Representative non-covalent bonds include hydrogen bonds, hydrophobic bonds, ionic bonds, pi-bond ring stacking, Van der Waals interactions, and the like.

Ligands, for example, are associated by specific affinity binding with binding sites on the reporter element. Direct association can take place at the time of tether synthesis, after tether synthesis, and before or after Xpandomer synthesis.

A "reporter" or "reporter construct" is composed of one or more reporter elements. Reporters include what are known as "tags" and "labels." The probe or nucleobase residue of the Xpandomer or S-Xpandomer can be considered a reporter. Reporters serve to parse the genetic information of the target nucleic acid.

"Reporter construct" comprises one or more reporters that can produce a detectable signal(s), wherein the detectable signal(s) generally contain sequence information. This signal information is termed the "reporter code" and is subsequently decoded into genetic sequence data. A reporter construct may also comprise tether segments or other architectural components including polymers, graft copolymers, block copolymers, affinity ligands, oligomers, haptens, aptamers, dendrimers, linkage groups or affinity binding group (e.g., biotin).

"Reporter detection characteristic" referred to as the "signal" describes all possible measurable or detectable elements, properties or characteristics used to communicate the genetic sequence information of a reporter directly or indirectly to a measurement device. These include, but are not limited to, fluorescence, multi-wavelength fluorescence, emission spectrum fluorescence quenching, FRET, emission, absorbance, reflectance, dye emission, quantum dot emission, bead image, molecular complex image, magnetic susceptibility, electron scattering, ion mass, magnetic resonance, molecular complex dimension, molecular complex impedance, molecular charge, induced dipole, impedance, molecular mass, quantum state, charge capacity, magnetic spin state, inducible polarity, nuclear decay, resonance, or complementarity.

"Reporter Code" is the genetic information from a measured signal of a reporter construct. The reporter code is decoded to provide sequence-specific genetic information data.

"Xprobe" or "S-Xprobe" is an expandable oligomeric substrate construct. Each Xprobe or S-Xprobe has a probe member and a tether member. The tether member generally having one or more reporter constructs. Xprobes or S-Xprobes with 5'-monophosphate modifications are compatible with enzymatic ligation-based methods for Xpandomer or S-Xpandomer synthesis, respectively. Xprobes or S-Xprobes with 5' and 3' linker modifications are compatible with chemical ligation-based methods for Xpandomer or S-Xpandomer synthesis, respectively.

"Xmer" or "S-Xmer" is an expandable oligomeric substrate construct. Each Xmer or S-Xmer has an oligomeric substrate member and a tether member, the tether member generally having one or more reporter constructs. Xmers and S-Xmers are 5'-triphosphates compatible with polymerase-based methods for synthesizing Xpandomers and S-Xpandomers, respectively.

"RT-NTP" is an expandable, 5' triphosphate-modified nucleotide substrate construct ("monomeric substrate") compatible with template dependant enzymatic polymerization. An RT-NTP has a modified deoxyribonucleotide triphosphate ("DNTP"), ribonucleotide triphosphate ("RNTP"), or a functionally equivalent analog substrate, collectively referred to as the nucleotide triphosphate substrate ("NTPS"). An RT-NTP has two distinct functional components; namely, a nucleobase 5'-triphosphate and a tether or tether precursor. After formation of the daughter strand the tether is attached between each nucleotide at positions that allow for controlled RT expansion. In one class of RT-NTP (e.g., Class IX), the tether is attached after RT-NTP polymerization. In some cases, the RT-NTP has a reversible end terminator and a tether that selectively cross-links directly to adjacent tethers. Each tether can be uniquely encoded with reporters that specifically identify the nucleotide to which it is tethered.

"XNTP" is an expandable, 5' triphosphate modified nucleotide substrate compatible with template dependent enzymatic polymerization. An XNTP has two distinct functional components; namely, a nucleobase 5'-triphosphate and a tether or tether precursor that is attached within each nucleotide at positions that allow for controlled RT expansion by intra-nucleotide cleavage.

"Processive" refers to a process of coupling of substrates which is generally continuous and proceeds with directionality. While not bound by theory, both ligases and polymerases, for example, exhibit processive behavior if substrates are added to a nascent daughter strand incrementally without interruption. The steps of hybridization and ligation, or hybridization and polymerization, are not seen as independent steps if the net effect is processive growth of the nascent daughter strand. Some but not all primer-dependent processes are processive.

"Promiscuous" refers to a process of coupling of substrates that proceeds from multiple points on a template at once, and is not primer dependent, and indicates that chain extension occurs in parallel (simultaneously) from more than one point of origin.

"Single-base extension" refers to a cyclical stepwise process in which monomeric substrates are added one by one. Generally the coupling reaction is restrained from proceeding beyond single substrate extension in any one step by use of reversible blocking groups.

"Single-probe extension" refers to a cyclical stepwise process in which oligomeric substrates are added one by one. Generally the coupling reaction is restrained from proceeding beyond single substrate extension in any one step by use of reversible blocking groups.

"Corresponds to" or "corresponding" is used here in reference to a contiguous single-stranded sequence of a probe, oligonucleotide, oligonucleotide analog, or daughter strand that is complementary to, and thus "corresponds to", all or a portion of a target nucleic acid sequence. The complementary sequence of a probe can be said to correspond to its target. Unless otherwise stated, both the complementary sequence of the probe and the complementary sequence of the target are individually contiguous sequences.

"Nuclease-resistant" refers to is a bond that is resistant to a nuclease enzyme under conditions where a DNA or RNA phosphodiester bond will generally be cleaved. Nuclease enzymes include, but are not limited to, DNase I, Exonuclease III, Mung Bean Nuclease, RNase I, and RNase H. One skilled in this field can readily evaluate the relative nuclease resistance of a given bond.

"Ligase" is an enzyme generally for joining 3'-OH 5'-monophosphate nucleotides, oligomers, and their analogs. Ligases include, but are not limited to, $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase, thermostable ligase, Ampligase thermostable DNA ligase, VanC-type ligase, 9° N DNA Ligase, Tsp DNA ligase, and novel ligases discovered by bioprospecting. Ligases also include, but are not limited to, ATP-dependent ligases including T4 RNA ligase, T4 DNA ligase, T7 DNA ligase, Pfu DNA ligase, DNA ligase I, DNA ligase III, DNA ligase IV, and novel ligases discovered by bioprospecting. These ligases include wild-type, mutant isoforms, and genetically engineered variants.

"Polymerase" is an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase I, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 9°N DNA Polymerase, 9°N DNA polymerase, Pfu DNA Polymerase, Tfl DNA Polymerase, Tth DNA Polymerase, RepliPHI Phi29 Polymerase, Ti DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. No. 6,329,178, U.S. Pat. No. 6,602,695, and U.S. Pat. No. 6,395,524 (incorporated by reference). These polymerases include wild-type, mutant isoforms, and genetically engineered variants.

"Encode" or "parse" are verbs referring to transferring from one format to another, and refers to transferring the genetic information of target template base sequence into an arrangement of reporters.

"Extragenetic" refers to any structure in the daughter strand that is not part of the primary backbone; for example, an extragenetic reporter is not the nucleobase itself that lies in the primary backbone.

"Hetero-copolymer" is a material formed by combining differing units (e.g., monomer subunit species) into chains of a "copolymer". Hetero-copolymers are built from discrete "subunit" constructs. A "subunit" is a region of a polymer composed a well-defined motif, where each motif is a species and carries genetic information. The term hetero-copolymer is also used herein to describe a polymer in which all the blocks are blocks constructed of repeating motifs, each motif having species-specific elements. The daughter strand and the Xpandomer are both hetero-copolymers whereby each subunit motif encodes 1 or more bases of the target template sequence and the entire target sequence is defined further with the sequence of motifs.

"Solid support" or "solid substrate" is a solid material having a surface for attachment of molecules, compounds, cells, or other entities. The surface of a solid support can be flat or not flat. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, polystyrene, polypropylene, polycarbonate, or polyallomer. A solid support can also be a bead, resin or particle of any shape. Such particles or beads can be comprised of any suitable material, such as glass or ceramics, and/or one or more polymers, such as, for example, nylon, polytetrafluoroethylene, TEFLON™, polystyrene, polyacrylamide, sepharose, agarose, cellulose, cellulose derivatives, or dextran, and/or can comprise metals, particularly paramagnetic metals, such as iron. Solid supports may be flexible, for example, a polyethylene terephthalate (PET) film.

"Reversibly blocking" or "terminator" refers to a chemical group that when bound to a second chemical group on a moiety prevents the second chemical group from entering into particular chemical reactions. A wide range of protecting groups are known in synthetic organic and bioorganic chemistry that are suitable for particular chemical groups and are compatible with particular chemical processes, meaning that they will protect particular groups during those processes and may be subsequently removed or modified (see, e.g., Metzker et al. Nucleic Acids Res., 22(20): 4259, 1994).

"Linker" is a molecule or moiety that joins two molecules or moieties, and provides spacing between the two molecules or moieties such that they are able to function in their intended manner. For example, a linker can comprise a diamine hydrocarbon chain that is covalently bound through a reactive group on one end to an oligonucleotide analog molecule and through a reactive group on another end to a solid support, such as, for example, a bead surface. Coupling of linkers to nucleotides and substrate constructs of interest can be accomplished through the use of coupling reagents that are known in the art (see, e.g., Efimov et al., *Nucleic Acids Res.* 27: 4416-4426, 1999). Methods of derivatizing and coupling organic molecules are well known in the arts of organic and bioorganic chemistry. A linker may also be cleavable or reversible.

"Detector construct" is an apparatus used for detection of the surrogate polymers. Detector constructs include any element necessary for detection of the surrogate polymers, and generally comprise at least one detector element. The detector element is capable of detecting the reporter elements of the surrogate polymers. Examples of detector elements include, but are not limited to, a nanopore channel, fluorescence detectors, UV detectors, chemical and electrochemical detectors, photoelectric detectors, and the like.

"Gating construct" is an apparatus used for controlling the flow of surrogate polymers. Gating constructs include all elements necessary to control the flow of surrogate polymers, and generally comprise at least one gating element. Examples of gating elements include nanoholes, and porous membranes, such as an aluminum oxide porous membrane.

"Paired-end surrogate polymer" or "paired-end daughter strand" both refer to a surrogate polymer or daughter strand produced by a bidirectional template-directed synthesis. A rolling circle polymerization process is an exemplary method for making a "paired-end surrogate polymer" or "paired-end daughter strand."

The term "reading", within the context of reading a reporter element or reporter construct, means identifying the reporter element or reporter construct. The identity of the reporter element or reporter construct can then be used to decode the genetic information of the target nucleic acid.

An "addressable, cleavable linkage" is a cleavable linkage whose location is known and can be individually targeted for cleavage.

A "fluorophore" is a fluorescent molecule or a component of a molecule that causes the molecule to be fluorescent. Fluorescien is a non-limiting example of a fluorophore.

General Overview

In general terms, methods and corresponding devices and products are described for replicating single-molecule target nucleic acids. Such methods utilize "Xpandomers" and "S-Xpandomers" (collectively referred to herein as "surrogate polymers") which permit sequencing of the target nucleic acid with increased throughput and accuracy. A surrogate polymer encodes (parses) the nucleotide sequence data of the target nucleic acid in a linearly expanded format, thereby improving spatial resolution, optionally with amplification of signal strength. These processes are referred to herein as "Sequencing by Expansion" or "SBX".

Sequencing by expansion enables low cost, high throughput detection methods by providing sequence targets that: (a) have high signal-to-noise reporters engineered for the detection method; (b) require no concurrent chemistry with detection; and/or (c) are engineered to the resolution requirements of the instrument. These surrogates enable high fidelity read lengths >100 bases which reduce post processing costs. SBX is disclosed in greater detail in Published PCT WO2008/157696, which is hereby incorporated by reference in its entirety.

More specifically, SBX can be solution-based with reagent costs below US$15 per 100 Gigabases of surrogate suitable for sequence reads. It converts DNA fragments >100 bases long into longer surrogate molecules called Xpandomers or S-Xpandomers (surrogate polymers). The sequential measurement of DNA bases is rescaled from discerning small molecular differences between bases that are spaced apart by ~4 Å to differentiating responses of large 100 Å reporters that are spaced apart by >100 Å. SBX preparation of DNA reduces the resolution requirements and increases the signal-to-noise for any detection methods that measure DNA directly, and provides many new measurement methods for sequencing applications.

SBX processes for synthesizing surrogate polymers are disclosed in more detail below and generally include polymerase and enzymatic or chemical ligation to sequentially link probes in the formation of surrogate polymers. For purpose of illustration, the processes described herein are enzymatic ligation processes. However, it should be understood that the procedures disclosed herein can be readily adapted for Xpandomers created by other SBX processes as described in WO2008/157696.

Sequencing Methods

As shown in FIG. 1A, native duplex nucleic acids have an extremely compact linear data density; about a 3.4 Å center-to-center separation between sequential stacked bases (2) of each strand of the double helix (1), and are therefore tremendously difficult to directly image or sequence with any accuracy and speed. When the double-stranded form is denatured to form single stranded polynucleotides (3,4), the resulting base-to-base separation distances are similar, but the problem becomes compounded by domains of secondary structure.

As shown in FIG. 1B, surrogate polymer (5), here illustrated as a concatenation of short oligomers (6,7) held together by extragenetic tethers T (8,9), is a synthetic replacement or "surrogate" for the nucleic acid target to be sequenced. Bases complementary to the template are incorporated into the surrogate polymer, and the regularly spaced tethers serve to increase the distance between the short oligomers (here each shown with four nucleobases depicted by circles). The surrogate polymer is made by a process in which a synthetic duplex intermediate is first formed by replicating a template strand. The daughter strand is unique in that it has both a linear backbone formed by the oligomers and a constrained surrogate polymer backbone comprised of folded tethers. The tethers are then opened up or "expanded" to transform the product into a chain of elongated tethers. Figuratively, the daughter strand can be viewed as having two superimposed backbones: one linear (primary backbone) and the other with "accordion" folds (constrained surrogate polymer). Selective cleavage of bonds in the daughter strand allows the accordion folds to expand to produce the surrogate polymer product. This process will be explained in more detail below, but it should be noted that the choice of four nucleobases per oligomer and particulars of the tether as shown in FIG. 1B is for purpose of illustration only, and in no way should be construed to limit the invention. It should also be noted that for purposes of illustration only, reporter elements are not shown in the surrogate polymer depicted in FIG. 1B.

The separation distance "D" between neighboring oligomers in the surrogate polymer is a process-dependent variable and is determined by the length of the tether T. As will be shown, the length of the tether T is designed into the substrate constructs, the building blocks from which the surrogate polymer is made. The separation distance D can be selected to be greater than 0.5 nm, or greater than 2 nm, or greater than 5 nm, or greater than 10 nm, or greater than 50 nm, for example. As the separation distance increases, the process of discriminating or "resolving" the individual oligomers becomes progressively easier. This would also be true if, instead of oligomers, individual nucleobases of another surrogate polymer species were strung together on a chain of tethers.

Referring again to FIG. 1A, native DNA replicates by a process of semi-conservative replication; each new DNA molecule is a "duplex" of a template strand (3) and a native daughter strand (4). The sequence information is passed from the template to the native daughter strand by a process of "template-directed synthesis" that preserves the genetic information inherent in the sequence of the base pairs. The native daughter strand in turn becomes a template for a next generation native daughter strand, and so forth. Surrogate polymers are formed by a similar process of template-directed synthesis, which can be an enzymatic or a chemical coupling process. However, unlike native DNA, once formed, surrogate polymers cannot be replicated by a biological process of semi-conservative replication and are not suitable for amplification by processes such as PCR. The surrogate polymer product is designed to limit unwanted secondary structure.

Figure 2B:
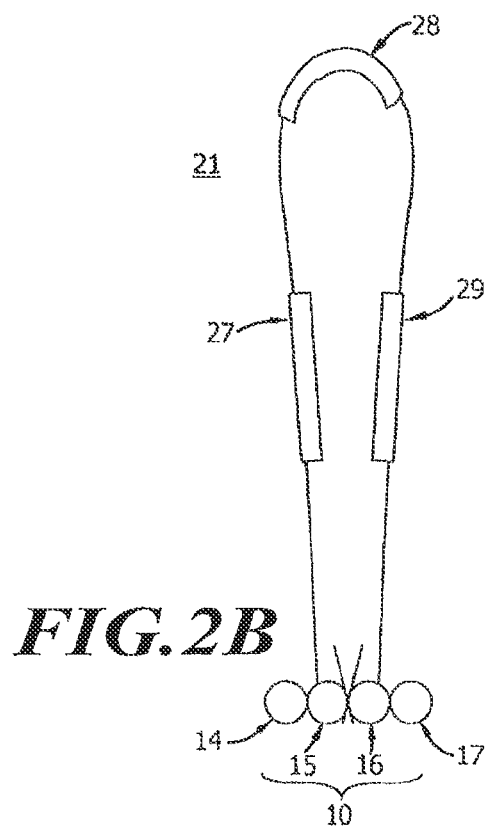

FIGS. 2A through 2D show representative surrogate polymer substrates (20,21,22,23). These are the building blocks from which surrogate polymers are synthesized. Other exemplary surrogate polymer substrates are addressed in subsequent sections. The surrogate polymer substrate constructs shown here have two functional components; namely, a probe member (10) and a "tether" member (11) in a loop configuration. The loop forms the elongated tether "T" of the final product. Solely for convenience in explanation, the probe member is again depicted with four nucleobase residues (14,15,16,17) as shown in FIG. 2B.

These substrate constructs can be end modified with R-groups, for example a 5'-monophosphate, 3'-OH suitable for use with a ligase (herein termed an "Xprobe" or "S-Xprobe") or as a 5'-triphosphate, 3'-OH suitable for use with a polymerase (herein termed an "Xmer" or "S-Xmer"). Other R groups may be of use in various protocols. In the first example shown in FIG. 3B, we present the synthesis of a surrogate polymer from a template strand of a target nucleic acid by a ligase-dependent process.

The four nucleobase residues (14,15,16,17) of the probe member (10) are selected to be complementary to a contiguous sequence of four nucleotides of the template. Each "probe" is thus designed to hybridize with the template at a complementary sequence of four nucleotides. By supplying a library of many such probe sequences, a contiguous complementary replica of the template can be formed. This daughter strand is termed an "Xpandomer intermediate" or "S-Xpandomer intermediate". The intermediates have duplex or single-stranded forms.

The tether loop is joined to the probe member (10) at the second and third nucleobase residues (15,16). The second and third nucleobase residues (15,16) are also joined to each other by a "selectively cleavable bond" (25) depicted by a "V". Cleavage of this cleavable bond enables the tether loop to expand. The linearized tether can be said to "bridge" the selectively cleavable bond site of the primary polynucleotide backbone of a daughter strand. Cleaving these bonds breaks up the primary backbone and forms the longer Xpandomer.

Selective cleavage of the selectively cleavable bonds (25) can be done in a variety of ways including, but not limited to, chemical cleavage of phosphorothiolate bonds, ribonuclease digestion of ribosyl 5'-3' phosphodiester linkages, cleavage of photocleavable bonds, and the like, as discussed is greater detail below.

FIGS. 2A through 2D represent exemplary embodiments of S-Xpandomers and Xpandomers. As mentioned above, an Xpandomer comprises probes which further comprise one or more reporter elements for parsing the entire genetic code of the probe, and an S-Xpandomer comprises probes which further comprise one or more reporter elements for parsing less than the entire genetic code of the probe. Any representation throughout the figures of one or more reporter elements attached to an Xprobe, Xmer, S-Xprobe or Smer or a surrogate polymer derived therefrom, is for exemplary purposes and, unless the content clearly dictates otherwise, is not meant to indicate the amount of genetic information contained within the probe or surrogate polymer (i.e. the exemplary surrogate polymers and components thereof represented in the figures represent both S-Xpandomers and Xpandomers and their respective components unless clearly stated otherwise).

Figure 2C:
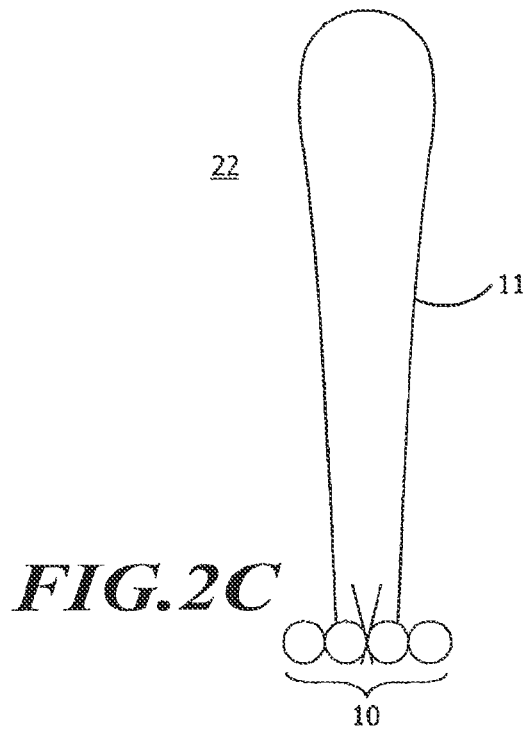
Figure 2D:
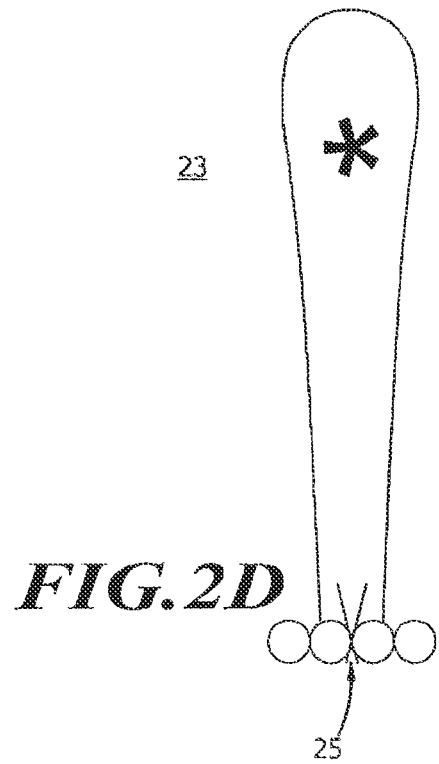

The substrate construct (20) shown in FIG. 2A has a single tether segment, represented here by an ellipse (26), for attachment of reporter elements. This segment is flanked with spacer tether segments (12,13), all of which collectively form the tether construct. One to many dendrimer(s), polymer(s), branched polymer(s) or combinations therein can be used, for example, to construct the tether segment. For the substrate construct (21) of FIG. 2B, the tether construct is composed of three tether segments for attachment of reporter elements (27,28,29), each of which is flanked with a spacer tether segment. The combination of reporter elements collectively form a "reporter construct" to produce a unique digital reporter code (for probe sequence identification). These reporter elements include, but are not limited to, fluorophores, FRET tags, beads, ligands, aptamers, peptides, haptens, oligomers, polynucleotides, dendrimers, stem-loop structures, affinity labels, mass tags, and the like. The tether loop (11) of the substrate construct (22) in FIG. 2C is "naked". The genetic information encoded in this construct is not encoded on the tether, but is associated with the probe (10), for example, in the form of one or more tagged nucleotides. The substrate construct (23) of FIG. 2D illustrates the general principal: as indicated by the asterisk (*), the sequence information of the probe is encoded or "parsed" in the substrate construct in a modified form more readily detected in a sequencing protocol. Because the sequence data is physically better resolved after cleavage of the selectively cleavable bond (25) to form the linearly elongated surrogate polymer, the asterisk (*) represents any form of encoded genetic information for which this is a benefit. The bioinformatic element or elements (*) of the substrate construct, whatever their form, can be detectable directly or can be precursors to which detectable elements are added in a post-assembly labeling step. In some instances, the genetic information is encoded in a molecular property of the substrate construct itself, for example a multi-state mass tag. In other instances, the genetic information is encoded by one or more fluorophores of FRET donor:acceptor pairs, or a nanomolecular barcode, or a ligand or combination of ligands, or in the form of some other labeling technique drawn from the art. Various embodiments will be discussed in more detail below.

The tether generally serves a number of functions: (1) to sequentially link, directly or indirectly, to adjacent tethers forming the surrogate polymer intermediate; (2) to stretch out and expand to form an elongated chain of tethers upon cleavage of selected bonds in the primary backbone or within the tether (see FIG. 1B); and/or (3) to provide a molecular construct for incorporating reporter elements, also termed "tags" or "labels", that encode the nucleobase residue sequence information of its associated substrate. The tether can be designed to optimize the encoding function by adjusting spatial separations, abundance, informational density, and signal strength of its constituent reporter elements. A broad range of reporter properties are useful for amplifying the signal strength of the genetic information encoded within the substrate construct. The literature directed to reporters, molecular bar codes, affinity binding, molecular tagging and other reporter elements is well known to one skilled in this field.

It can be seen that if each substrate of a substrate construct contains x nucleobases, then a library representing all possible sequential combinations of x nucleobases would contain $4^x$ probes (when selecting the nucleobases from A, T, C or G). Fewer or more combinations can be needed if other bases are used. These substrate libraries are designed so that each substrate construct contains (1) a probe (or at least one nucleobase residue) complementary to any one of the possible target sequences of the nucleic acid to be sequenced and (2) a unique reporter construct that encodes the identity or partial identity of the target sequence which that particular probe (or nucleobase) is complementary to. A library of probes containing two nucleobases would have 16 unique members; a library of probes containing three nucleobases would have 64 unique members, and so forth. A representative library would have the four individual nucleobases themselves, but configured to accommodate a tethering means.

Figure 3A:
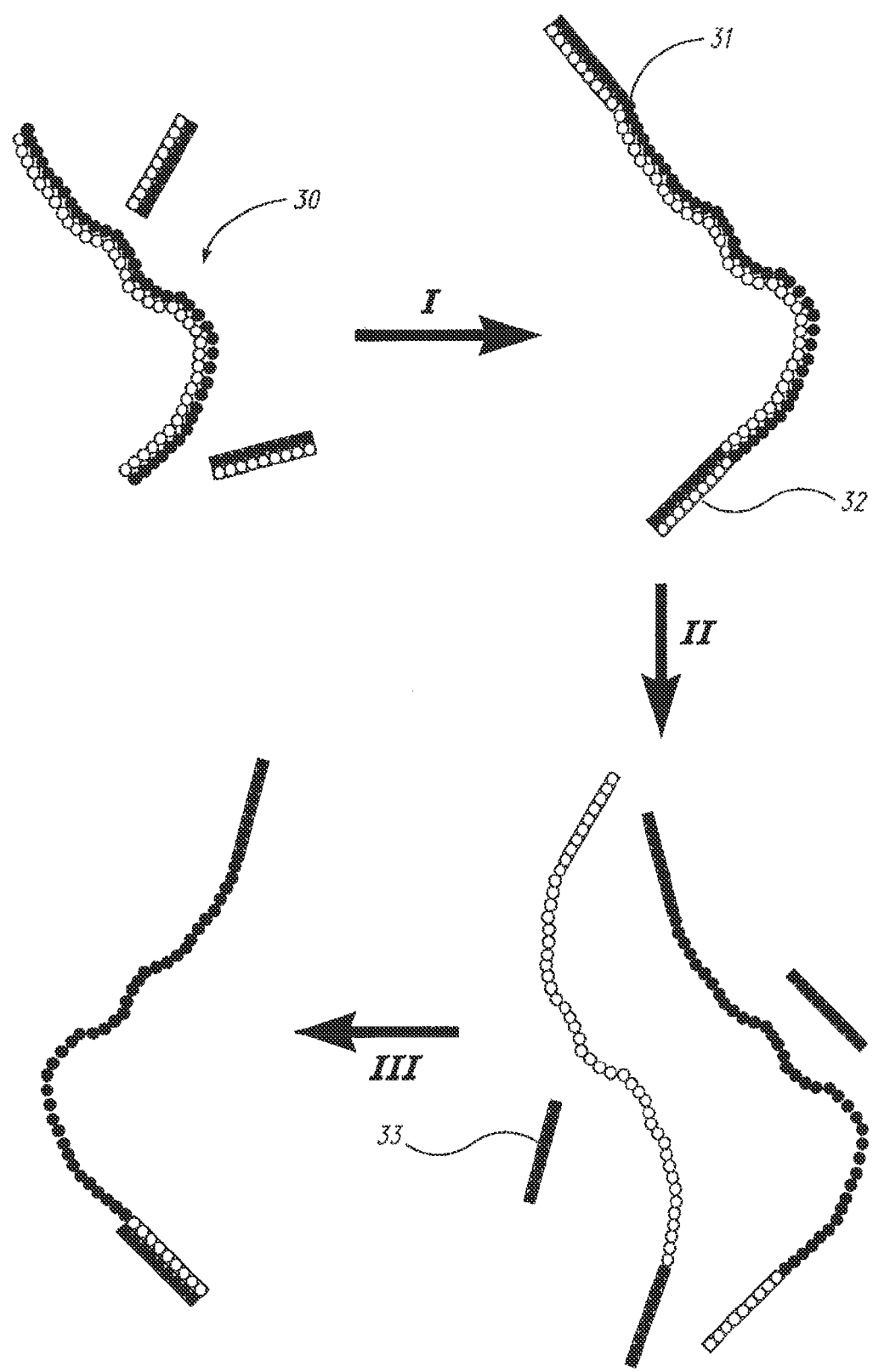
FIGS. 3A, 3B and 3C are schematics illustrating simplified steps for synthesizing an Xpandomer from a target nucleic acid.
Figure 3B:
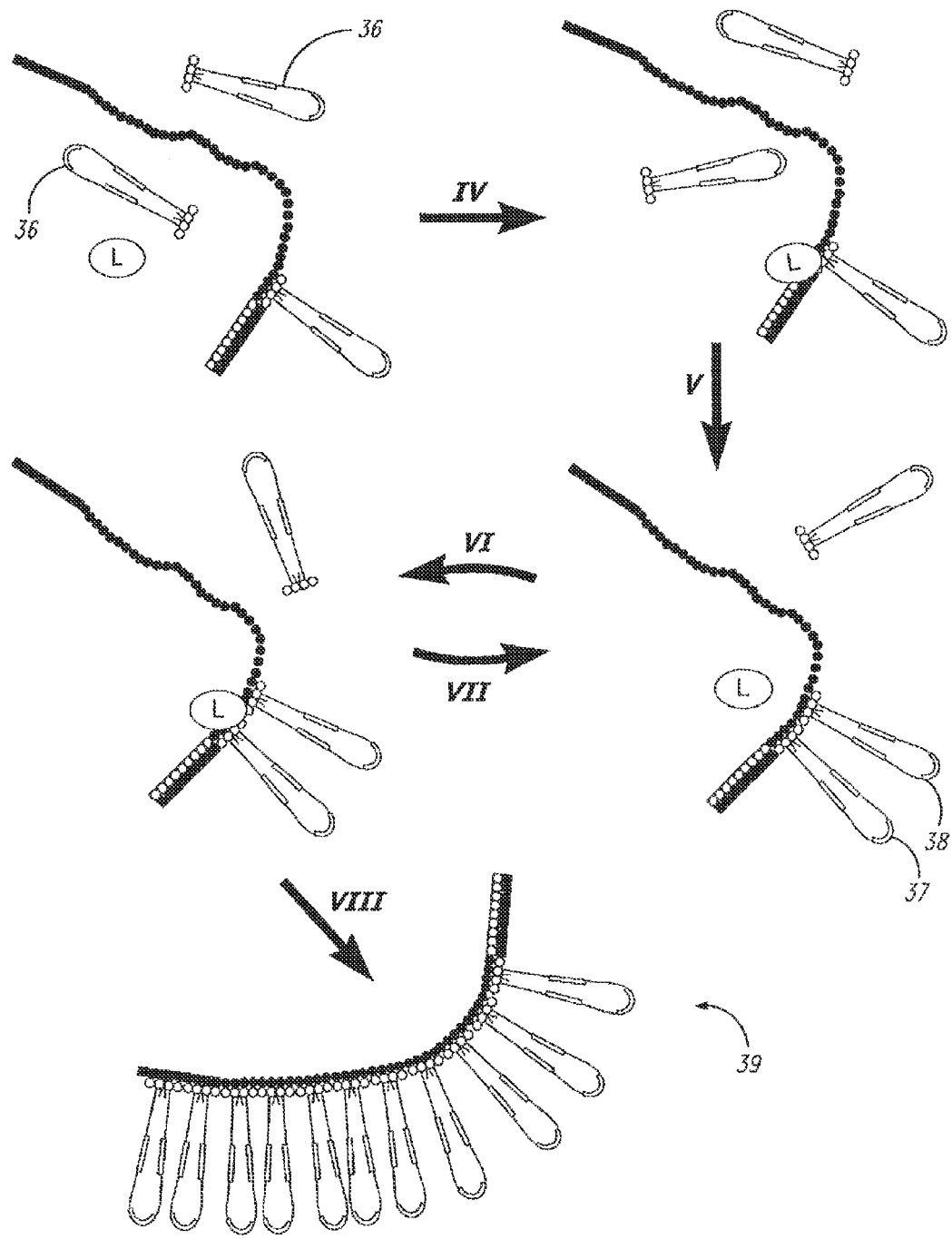
Figure 3C:
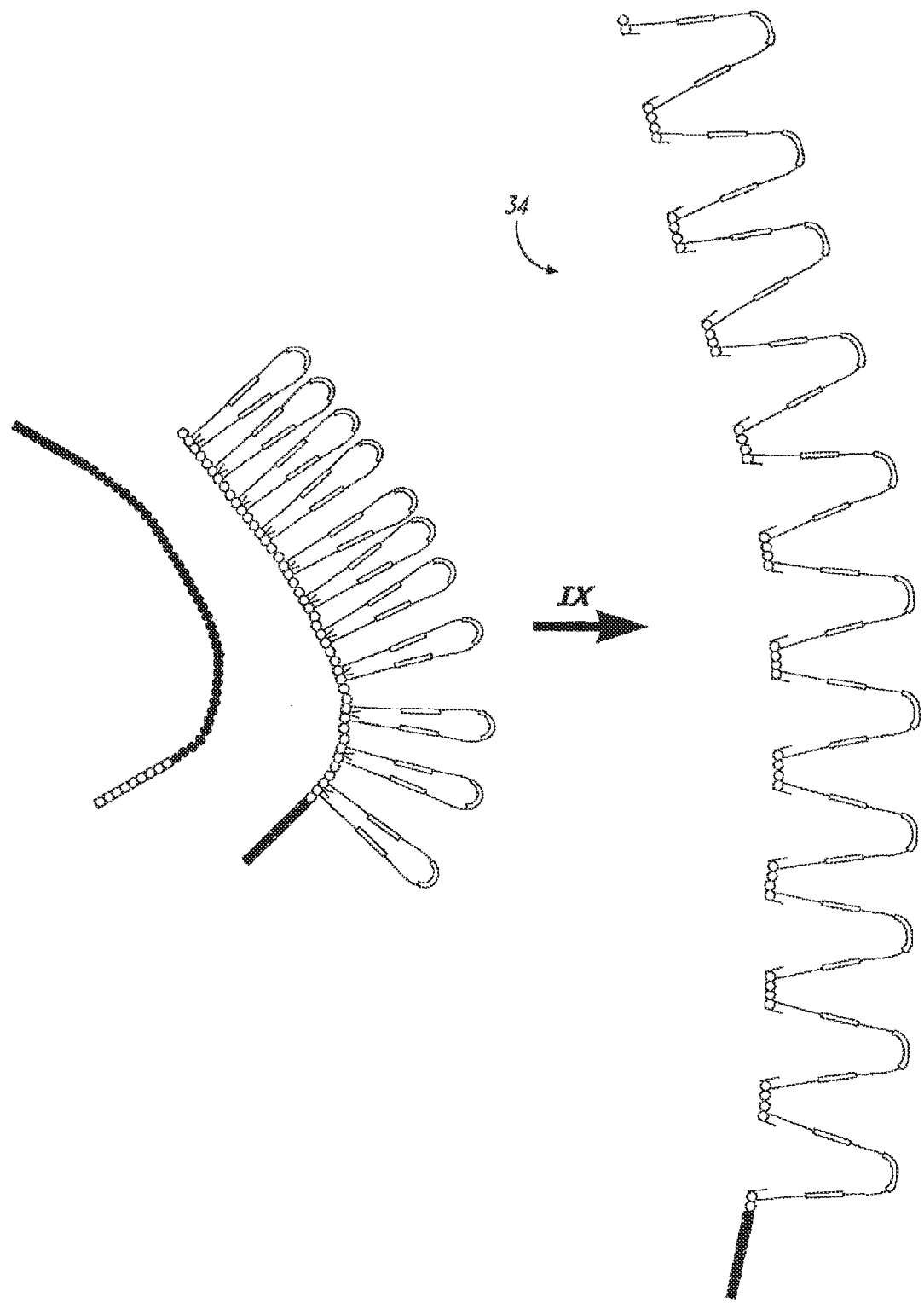

An exemplary synthesis of an Xpandomer is illustrated in FIGS. 3A through 3C. The substrate depicted here is an Xprobe and the method can be described as hybridization with primer-dependent processive ligation in free solution. S-Xpandomers can be synthesized in an analogous manner.

Many well known molecular biological protocols, such as protocols for fragmenting the target DNA and ligating end adaptors, can be adapted for use in sequencing methods and are used here to prepare the target DNA (30) for sequencing. Here we illustrate, in broad terms that which would be familiar to those skilled in the art, processes for polishing the ends of the fragments and blunt-ended ligation of adaptors (31,32) designed for use with sequencing primers. These actions are shown in Step I of FIG. 3A. In Steps II and III, the target nucleic acid is denatured and annealed with suitable primers (33) complementary to the adaptors.

In FIG. 3B, the primed template strand of Step III is contacted with a library of substrate constructs (36) and ligase (L), and in Step IV conditions are adjusted to favor hybridization followed by ligation at a free 3'-OH of a primer-template duplex. Optionally in Step V the ligase dissociates, and in Steps VI and VII, the process of hybridization and ligation can be recognized to result in extension by cumulative addition of substrates (37,38) to the primer end. Although priming can occur from adaptors at both ends of a single stranded template, the growth of a nascent Xpandomer daughter strand is shown here to proceed from a single primer, solely for simplicity. Extension of the daughter strand is represented in Steps VI and VII, which are continuously repeated (incrementally, without interruption). These reactions occur in free solution and proceed until a sufficient amount of product has been synthesized. In Step VIII, formation of a completed Xpandomer intermediate (39) is shown.

Relatively long lengths of contiguous nucleotide sequence can be efficiently replicated in this manner to form Xpandomer intermediates (and S-Xpandomer intermediates analogously). It can be seen that continuous read lengths ("contigs") corresponding to long template strand fragments can be achieved with this technology. It will be apparent to one skilled in the art that billions of these single molecule SBX reactions can be done simultaneously in an efficient batch process in a single tube. Subsequently, the shotgun products of these syntheses can be sequenced.

In FIG. 3C, the next steps of the SBX process are depicted. Step IX shows denaturation of the duplex Xpandomer intermediate followed by cleavage of selectively cleavable bonds in the backbone, with the selectively cleavable bonds designed so that the tether loops "open up", forming the linearly elongated Xpandomer product (34). Such selective cleavage may be achieved by any number of techniques known to one skilled in the art, including, but not limited to, phosphorothiolate cleavage with metal cations as disclosed by Mag et al. ("Synthesis and selective cleavage of an oligodeoxynucleotide containing a bridged internucleotide 5'-phosphorothioate linkage", *Nucleic Acids Research* 19(7):1437-1441, 1991), acid catalyzed cleavage of phosphoramidate as disclosed by Mag et al. ("Synthesis and selective cleavage of oligodeoxyribonucleotides containing non-chiral internucleotide phosphoramidate linkages", *Nucleic Acids Research* 17(15): 5973-5988, 1989), selective nuclease cleavage of phosphodiester linkages as disclosed by Gut et al. ("A novel procedure for efficient genotyping of single nucleotide polymorphisms", *Nucleic Acids Research* 28(5): E13, 2000) and separately by Eckstein et al. ("Inhibition of restriction endonuclease hydrolysis by phosphorothioate-containing DNA", *Nucleic Acids Research*, 25; 17(22): 9495, 1989), and selective cleavage of photocleavable linker modified phosphodiester backbone as disclosed by Sauer et al. ("MALDI mass spectrometry analysis of single nucleotide polymorphisms by photocleavage and charge-tagging", *Nucleic Acids Research* 31, 11 e63, 2003), Vallone et al. ("Genotyping SNPs using a UV-photocleavable oligonucleotide in MALDI-TOF MS", *Methods Mol. Bio.* 297:169-78, 2005), and Ordoukhanian et al. ("Design and synthesis of a versatile photocleavable DNA building block, application to phototriggered hybridization", *J. Am. Chem. Soc.* 117, 9570-9571, 1995).

Refinements of the basic process, such as wash steps and adjustment of conditions of stringency are well within the skill of an experienced molecular biologist. Variants on this process include, for example, immobilization and parsing of the target strands, stretching and other techniques to reduce secondary structure. Methods for preparation of Xpandomers are described in greater detail in Published PCT WO 2008/157696, which is hereby incorporated by reference. One skilled in the art will understand that the methods described herein, and in Published PCT WO 2008/157696, for preparation of Xpandomers are applicable in an analogous manner to preparation of S-Xpandomers.

The surrogate polymers comprise a plurality of subunits coupled in a sequence corresponding to a contiguous nucleotide sequence of all or a portion of the target nucleic acid. In one embodiment, the surrogate polymers may be represented by the following structures:

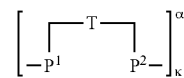

wherein
T represents the tether;
$P^1$ represents a first probe moiety;
$P^1$ represents a second probe moiety;
$\kappa$ represents the $\kappa^{th}$ subunit in a chain of m subunits, where m is an integer greater than three; and
$\alpha$ represents a species of a subunit motif selected from a library of subunit motifs, wherein each of the species comprises sequence information of the contiguous nucleotide sequence of a portion of the target nucleic acid;

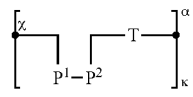

wherein
T represents the tether;
$P^1$ represents a first probe moiety;
$P^2$ represents a second probe moiety;
$\kappa$ represents the $\kappa^{th}$ subunit in a chain of m subunits, where m is an integer greater than three;
$\alpha$ represents a species of a subunit motif selected from a library of subunit motifs, wherein each of the species comprises sequence information of the contiguous nucleotide sequence of a portion of the target nucleic acid; and
$\chi$ represents a bond with the tether of an adjacent subunit;

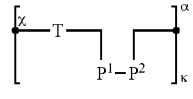

wherein
T represents the tether;
$P^1$ represents a first probe moiety;
$P^2$ represents a second probe moiety;
$\kappa$ represents the $k^{th}$ subunit in a chain of m subunits, where m is an integer greater than three;
$\alpha$ represents a species of a subunit motif selected from a library of subunit motifs, wherein each of the species comprises sequence information of the contiguous nucleotide sequence of a portion of the target nucleic acid; and
$\chi$ represents a bond with the tether of an adjacent subunit;

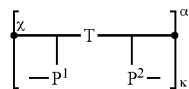

wherein

T represents the tether;

$P^1$ represents a first probe moiety;

$P^2$ represents a second probe moiety;

κ represents the $κ^{th}$ subunit in a chain of m subunits, where m is an integer greater than three;

α represents a species of a subunit motif selected from a library of subunit motifs, wherein each of the species comprises sequence information of the contiguous nucleotide sequence of a portion of the target nucleic acid; and χ represents a bond with the tether of an adjacent subunit;

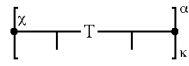

wherein

T represents the tether;

κ represents the $κ^{th}$ subunit in a chain of m subunits, where m is an integer greater than three;

α represents a species of a subunit motif selected from a library of subunit motifs, wherein each of the species comprises sequence information of the contiguous nucleotide sequence of a portion of the target nucleic acid; and χ represents a bond with the tether of an adjacent subunit;

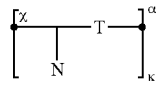

wherein

T represents the tether;

N represents a nucleobase residue;

χ represents the $κ^{th}$ subunit in a chain of m subunits, where m is an integer greater than ten;

α represents a species of a subunit motif selected from a library of subunit motifs, wherein each of the species comprises sequence information of the contiguous nucleotide sequence of a portion of the target nucleic acid; and χ represents a bond with the tether of an adjacent subunit;

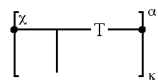

wherein

T represents the tether;

κ represents the $κ^{th}$ subunit in a chain of m subunits, where m is an integer greater than ten;

α represents a species of a subunit motif selected from a library of subunit motifs, wherein each of the species comprises sequence information of the contiguous nucleotide sequence of a portion of the target nucleic acid; and χ represents a bond with the tether of an adjacent subunit;

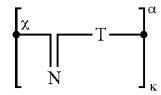

wherein

T represents the tether;

N represents a nucleobase residue;

κ represents the $κ^{th}$ subunit in a chain of m subunits, where m is an integer greater than ten;

α represents a species of a subunit motif selected from a library of subunit motifs, wherein each of the species comprises sequence information of the contiguous nucleotide sequence of a portion of the target nucleic acid; and χ represents a bond with the tether of an adjacent subunit;

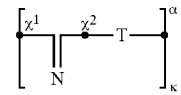

wherein

T represents the tether;

N represents a nucleobase residue;

κ represents the $κ^{th}$ subunit in a chain of m subunits, where m is an integer greater than ten;

α represents a species of a subunit motif selected from a library of subunit motifs, wherein each of the species comprises sequence information of the contiguous nucleotide sequence of a portion of the target nucleic acid;

$χ^1$ represents a bond with the tether of an adjacent subunit; and $χ^2$ represents an inter-tether bond; or

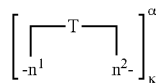

wherein

T represents the tether;

$n^1$ and $n^2$ represents a first portion and a second portion, respectively, of a nucleobase residue;

κ represents the $κ^{th}$ subunit in a chain of m subunits, where m is an integer greater than ten; and α represents a species of a subunit motif selected from a library of subunit motifs, wherein each of the species comprises sequence information of the contiguous nucleotide sequence of a portion of the target nucleic acid.

In some embodiments, the surrogate polymer daughter strands may be formed by template-directed synthesis from a plurality of subunits having the following structure:

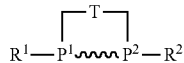

wherein
T represents the tether;
P¹ represents a first probe moiety;
P² represents a second probe moiety;
~ represents the at least one selectively cleavable bond; and
R¹ and R² represent the same or different end groups for the template directed synthesis of the daughter strand;

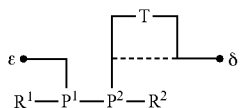

wherein
T represents the tether;
P¹ represents a first probe moiety;
P² represents a second probe moiety;
R¹ and R² represent the same or different end groups for the template directed synthesis of the daughter strand;
ε represents a first linker group;
δ represents a second linker group; and
"- - - -" represents a cleavable intra-tether crosslink;

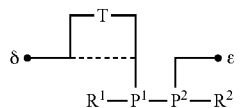

wherein
T represents the tether;
P¹ represents a first probe moiety;
P² represents a second probe moiety;
R¹ and R² represent the same or different end groups for the template directed synthesis of the daughter strand;
ε represents a first linker group;
δ represents a second linker group; and
"- - - -" represents a cleavable intra-tether crosslink;

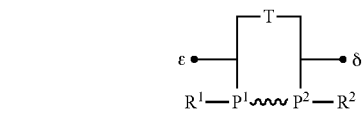

wherein
T represents the tether;
P¹ represents a first probe moiety;
P² represents a second probe moiety;
~ represents the at least one selectively cleavable bond;
R¹ and R² represent the same or different end groups for the template directed synthesis of the daughter strand;
ε represents a first linker group; and
δ represents a second linker group;

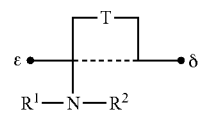

wherein
T represents the tether;
P¹ represents a first probe moiety;
P² represents a second probe moiety;
~ represents the at least one selectively cleavable bond;
R¹ and R² represent the same or different end groups for the template directed synthesis of the daughter strand;
ε represents a first linker group; and
δ represents a second linker group;

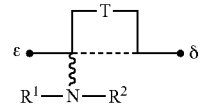

wherein
T represents the tether;
N represents a nucleobase residue;
R¹ and R² represent the same or different end groups for the template directed synthesis of the daughter strand;
ε represents a first linker group;
δ represents a second linker group; and
"- - - -" represents a cleavable intra-tether crosslink;

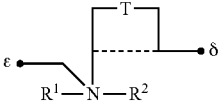

wherein
T represents the tether;
N represents a nucleobase residue;
R¹ and R² represent the same or different end groups for the template directed synthesis of the daughter strand;
~ represents the at least one selectively cleavable bond;
ε represents a first linker group;
δ represents a second linker group; and
"- - - -" represents a cleavable intra-tether crosslink;

wherein
T represents the tether;
N represents a nucleobase residue;
R¹ and R² represent the same or different end groups for the template directed synthesis of the daughter strand;
ε represents a first linker group;
δ represents a second linker group; and
"- - - -" represents a cleavable intra-tether crosslink;

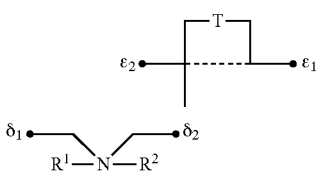

wherein

T represents the tether;

N represents a nucleobase residue;

$R^1$ and $R^2$ represent the same or different end groups for the template directed synthesis of the daughter strand;

$\epsilon_1$ and E2 represent the same or different first linker groups;

$\delta_1$ and $\delta_2$ represent the same or different second linker groups; and "- - - -" represents a cleavable intra-tether crosslink; or

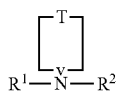

wherein

T represents the tether;

N represents a nucleobase residue;

V represents an internal cleavage site of the nucleobase residue; and $R^1$ and $R^2$ represent the same or different end groups for the template directed synthesis of the daughter strand.

$R^1$ and $R^2$ are end groups configured as appropriate for the synthesis protocol in which the subunit is used. For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

Other exemplary surrogate polymer and surrogate polymer daughter strands are disclosed in greater detail in Published PCT WO 2008/157696.

In one embodiment, the reporter constructs are attached to the probe or nucleobase by a polymer tether. In other embodiments, the tether is not associated with the reporter constructs. The tethers can be constructed of one or more durable, aqueous- or solvent-soluble polymers including, but not limited to, the following segment or segments: polyethylene glycols, polyglycols, polypyridines, polyisocyanides, polyisocyanates, poly(triarylmethyl) methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments. Such polymers can be circularized at attachment points on a substrate construct.

The tether is generally resistant to entanglement or is folded so as to be compact. Polyethylene glycol (PEG), polyethylene oxide (PEO), methoxypolyethylene glycol (mPEG), and a wide variety of similarly constructed PEG derivatives (PEGs) are broadly available polymers that can be utilized in the practice of this invention. Modified PEGs are available with a variety of bifunctional and heterobifunctional end crosslinkers and are synthesized in a broad range of lengths. PEGs are generally soluble in water, methanol, benzene, dichloromethane, and many common organic solvents. PEGs are generally flexible polymers that typically do not non-specifically interact with biological chemicals.

Other polymers that may be employed as tethers, and provide "scaffolding" for reporters, include, for example, poly-glycine, poly-proline, poly-hydroxyproline, poly-cysteine, poly-serine, poly-aspartic acid, poly-glutamic acid, and the like. Side chain functionalities can be used to build functional group-rich scaffolds for added signal capacity or complexity.

Reducing the size and mass of the substrate construct can also be achieved by using unlabeled tethers. By eliminating bulky reporters (and reporter scaffolding such as dendrimers, which for some encoding embodiments comprise over 90% of the tether mass), hybridization and/or coupling kinetics can be enhanced. Post-assembly tether labeling can then be employed. Reporters are bound to one or more linkage chemistries that are distributed along the tether constructs using spatial or combinatorial strategies to encode the base sequence information. Post-assembly tether labeling may be particularly advantageous in the context of S-Xpandomers due to their reduced reporter content.

As mentioned above, the S-Xpandomers differ from the Xpandomers in that the reporter construct(s) of the S-Xpandomers encode only a subset of the probe sequence information. This is beneficial in some embodiments because it simplifies the probe and reduces its kinetic load, S-Xprobes are Xprobes that encode less than all the base sequence information of their probes. For example, in one embodiment, an S-Xprobe may have one 4-state reporter that encodes one base (e.g., 5' end base) of its 6-base probe. When assembled into an S-Xpandomer, the base information is sampled as discrete intervals along the target. As a result, multiple S-Xpandomers that are frame shifted with respect to the base position are required to encode the entire target nucleic acid sequence. Rolling circle polymerization is an exemplary method of producing all the required S-Xpandomer sequence.

Figure 4:
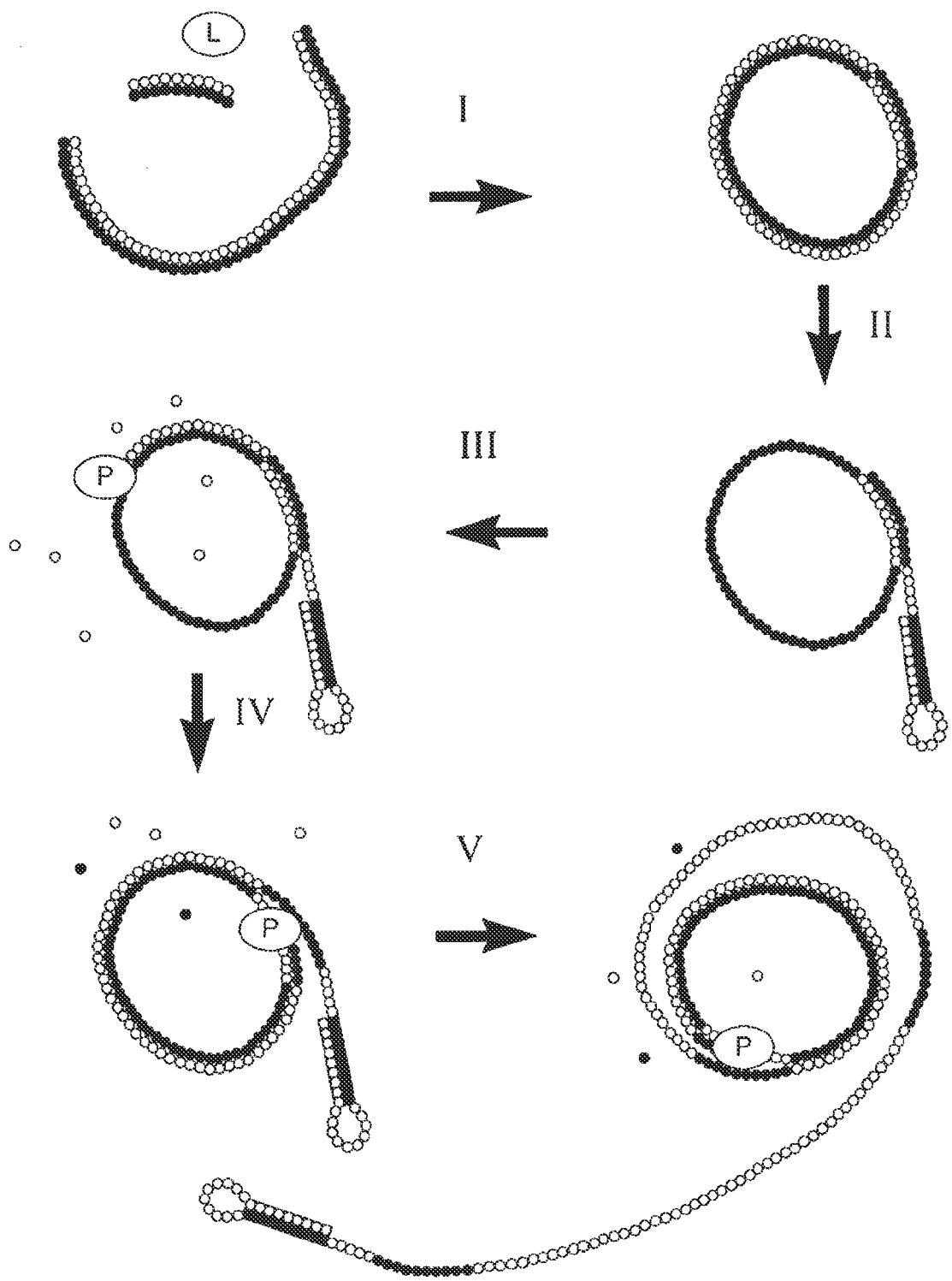
FIG. 4 illustrates rolling circular polymerization.

FIG. 4 shows a rolling circle polymerization process. In Step I, a ligation reaction mix (L) is added, and the target DNA fragment (depicted as the longer duplex) is ligated to a double-stranded adapter oligomer (depicted as the shorter duplex) to form a circularized target construct. In Step II, the target is denatured into a single stranded target and a universal hairpin primer is hybridized to its complement within the adapter portion of the single-stranded, circularized target. The hairpin is not phosphorylated on its 5' end and will only extend from its primer end. In Step III, a polymerase reaction mix (P) is added. Polymerase extension proceeds and extends from the 3' end of the universal primer. In Step IV, polymerization of the available nucleic acid monomers has extended the nascent 3' end around the circularized template and displaces the hairpin to continue for a second time around displacing the strand as it advances. Step V illustrates continuous rolling circle replication. The reaction is stopped when the product is of sufficient average length.

After denaturation and purification, the remaining rolling-circle product has a series of more than R replication units. A replication unit is the rolling-circle extension product portion that replicates one loop of the circularized template. The purified product (i.e. primed DNA) may then be used for an S-Xpandomer synthesis using an such as that shown in FIGS. 3B and 3C. In this case S-Xprobes are incorporated from the nascent 5' end.

An S-Xpandomer, synthesized from S-Xprobes, which encode for single bases, will encode for the whole sequence of the circularized template provided the following condition is met: for the replication unit length in bases, L, the S-Xprobe probe length in bases, S, and the number of replication units R, the remainders of L/S, 2L/S, . . . , RL/S must include the numbers 0, 1, 2, . . . , S−1. In general when this is satisfied, the minimum R is equal to S. Each remainder is equivalent to the frame shift (in number of bases) that occurs in the S-Xprobe position in the subsequent replication unit for the 1st, 2nd, . . . Rth replication unit respectively. This is further equivalent to saying that a frame shift of the S-Xprobe position occurs after each replication unit and that after R replication units, these frame shifts cause an S-Xprobe in the S-Xpandomer to have every position relative to a replication unit reference.

In an exemplary embodiment, a 5-base S-Xprobe probe is used to produce S-Xpandomers of ~1000 base DNA targets. Ignoring other error sources, for target lengths that have equally distributed remainders of 0, 1, 2, 3, or 4 when divided by 5 (S=5) and if R is equal to or greater than 5 then only the case with remainder zero will not generate S-polymers that encode for the entire sequence of the target DNA.

To increase assembly efficiency of sequence reads in redundant or low complexity regions of the genome, sequence reads based upon paired-ends may be use. A paired-end read has two read sequences taken from opposite ends of a long target DNA. By using the length of the DNA target, the two sequences can reference each other to assist in their assembly positioning. Paired-end nucleic acids, including paired-end surrogate polymers, may be produced by ligating probes bidirectionally from the primer. This process starts by shearing and filtering target DNA into a narrow length range 1000s of bases long, 10 kb+/−0.5 kb for example, as illustrated in FIG. 5A.

Figure 5A:
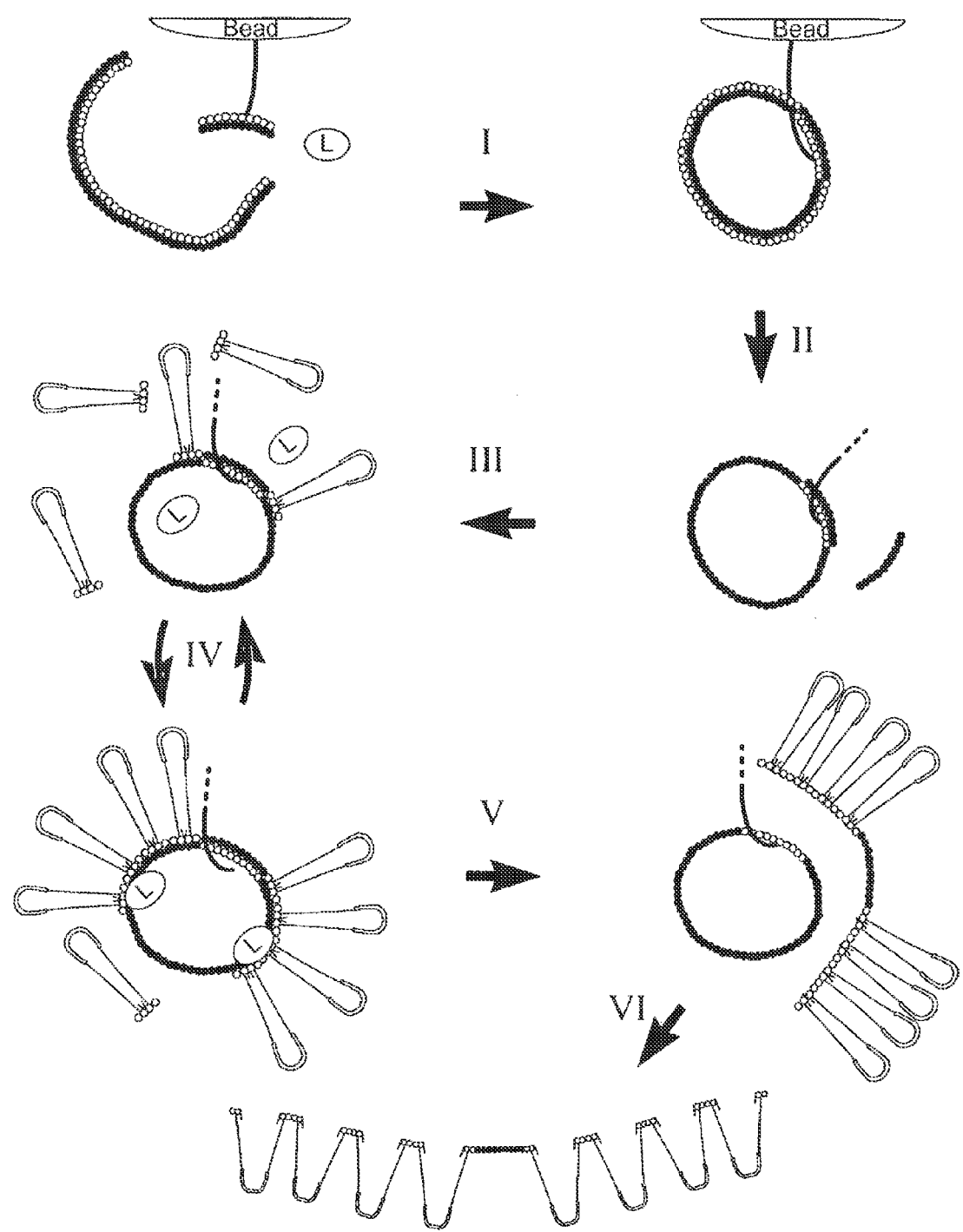
FIGS. 5A and 5B illustrate methods of making paired-end surrogate polymers and methods for preparing target oligomers for preparing paired-end methods, respectively.

FIG. 5A shows bidirectional synthesis of a paired-end surrogate polymer. In step I, the DNA targets are blunt-ended, ligated to a primer adapter, and circularized. The primer adapter optionally comprises a tether for optional attachment to beads or other solid substrate. The tether may use a covalent bond along with a cleavable linkage for this attachment, or may use an oligo to attach by hybridization. In step II, the circularized product is denatured. A primer with a 5' phosphate and a 3' OH then duplexes to the adaptor to initiate ligation bidirectionally. In Step III the SBX process proceeds and s-Xprobes or Xprobes hybridize and are ligated (step IV) along the circularized target in both directions from both the nascent 3' and 5' ends The primer can also be designed in a manner similar to S-Xprobes and Xprobes to carry information on a tether about the reaction such as the length range of the target (e.g., 10 kb, 20 kb, 30 kb) or to identify the target itself if there is target parsing or multiplexing or just to identify the primer relative to each of the pair of ends. The sequence region of paired-end nucleic acids (surrogate polymers as well as other nucleic acids) may contain any number of nucleobase residues. For example, a sequence region comprise 10 more nucleobases, but sequence regions with fewer bases are also possible.

In step V, the paired-end surrogate polymer daughter strand has extended a sufficient number of bases in each direction. The product is washed and denatured from the target. In step VI the product is filtered for the higher value longer reads, and cleaved to open the tethers yielding the paired-end surrogate polymer. This resulting product encodes the paired-end sequence of the circularized target.

Figure 5B:
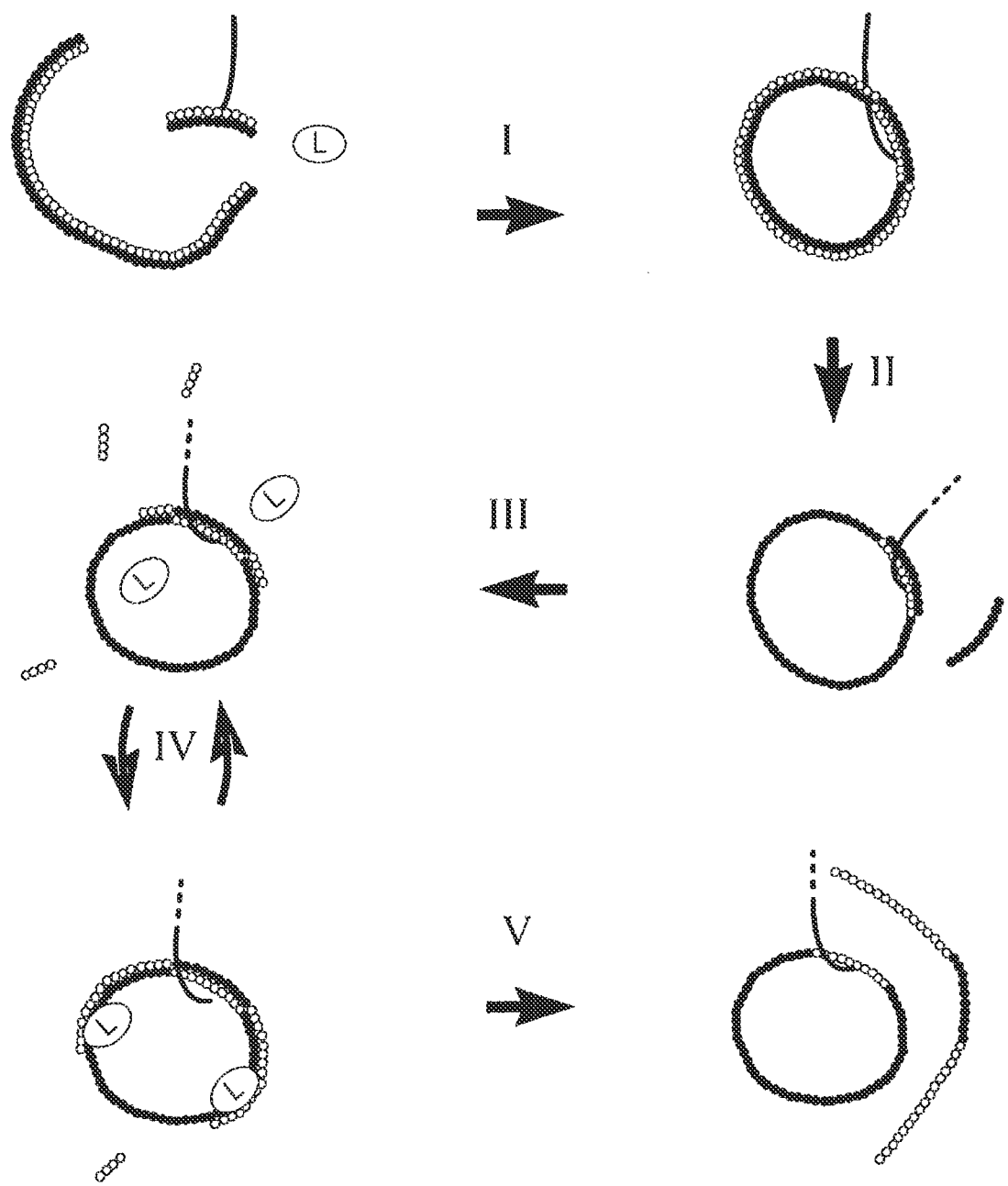

FIG. 5B shows generation of a paired-end DNA target in a way similar to that described above, except that oligo probes are used instead of s-Xprobes or Xprobes. The product in this case may be used as the surrogate polymer DNA target, used as a DNA target for other sequencing methods, or used as the analyte input to a sequencing method. Referring to FIG. 5B, in step I, the DNA targets are blunt-ended, ligated to a primer adapter, and circularized. The primer adapter optionally comprises a tether for optional attachment to beads or other solid substrate. The tether may use a covalent bond along with a cleavable linkage for this attachment, or may use an oligo to attach by hybridization. In step II, the circularized product is denatured. A primer with a 5' phosphate and a 3' OH then duplexes to the adaptor to initiate ligation bidirectionally. In Step III the oligo probes hybridize and are ligated (step IV) along the circularized target in both directions from both the nascent 3' and 5' ends In step V, the daughter strand has extended a sufficient number of bases in each direction. The product is washed and denatured from the target.

The paired-end methods described above find utility in surrogate polymer methods as well as methods employing other nucleic acids (e.g. DNA, etc.) In addition to the above methods, other variations are possible. For example, the bidirectional synthesis may proceed from both the 3' and 5' ends of the primer via ligation reactions. In another exemplary method, the bidirectional synthesis proceeds from the 5' end of the primer via a ligation reaction, and extension of the 3' end of the primer proceeds via a polymerase reaction. On skilled in the art will recognize that other combinations of the above methods are also possible.

The disclosed surrogate polymers may comprise any number of subunits which may be, for example, greater than 10, greater than 100, or greater than 1000. Further, while the reporter constructs, $C^1$, $C^2$, $C^3$, $C^4$, $C^5$ and $C^6$, are depicted above as being joined to the probes, $P^1$, $P^2$, $P^3$, $P^4$, $P^5$ and $P^6$, by a bond, the reporter constructs (also referred to herein as reporter elements) may be joined to the tether or may be a component of the probe or tether itself, and depiction of the reporter constructs as a separate linked moiety is for purpose of illustration only.

The nucleobase residues of the probes may be, for example, adenine (A), guanine (G), cytosine (C) or thymine (T), or other heterocyclic base moieties as discussed in greater detail below, including universal bases. The template-directed synthesis of the daughter strand may be accomplished by any number of methods, including techniques involving one or more enzymatic ligations, polymerase reactions and/or chemical ligations. As noted above, the daughter strand comprises a plurality of subunits, the number of which can vary widely, for example, be greater than 30, or greater than 1000.

Detection of the disclosed surrogate polymers can be accomplished by any of a variety of techniques. For example, the reporter constructs can be detected by passing the surrogate polymer through a nanopore, by interrogation with an electron beam, by scanning tunneling microscopy (STM), and/or transmission electron microscopy (TEM). Other exemplary detection techniques are described hereinbelow. The nature of the reporter construct will largely depend upon the detection method employed. The reporter construct may be joined to at least one nucleobase residue of the probe by a covalent bond. Alternatively, or in addition to, the reporter construct may be a component of at least one nucleobase residue of the probe. The reporter construct may also optionally be associated with or a part of the tether.

In more specific embodiments, the reporter elements for parsing the genetic information may be associated with the tethers of the surrogate polymer, with the surrogate polymer prior to cleavage of the at least one selectively cleavable bond, and/or with the surrogate polymer after cleavage of the at least one selectively cleavable bond. The surrogate polymer may further comprise all or a portion of the at least one probe or nucleobase residue, and the reporter elements for parsing the genetic information may be associated with the at least one probe or nucleobase residue or may be the probe or nucleobase residues themselves. Further, the selectively cleavable bond may be a covalent bond, an intra-tether bond, a bond between or within probes or nucleobase residues of the daughter strand, and/or a bond between the probes or nucleobase residues of the daughter strand and a target template.

A broad range of suitable commercially available chemistries (Pierce, Thermo Fisher Scientific, USA) can be adapted for preparation of the probes comprising selectively cleavable linker bonds. Common linker chemistries include, for example, NHS-esters with amines, maleimides with sulfhydryls, imidoesters with amines, EDC with carboxyls for reactions with amines, pyridyl disulfides with sulfhydryls, and the like. Other embodiments involve the use of functional groups like hydrazide (HZ) and 4-formylbenzoate (4FB) which can then be further reacted to form linkages. More specifically, a wide range of crosslinkers (hetero- and homo-bifunctional) are broadly available (Pierce) which include, but are not limited to, Sulfo-SMCC (Sulfosuccinimidyl 4-[N-maleimidomethyl]cyclohexane-1-carboxylate), SIA (N-Succinimidyl iodoacetate), Sulfo-EMCS ([N-e-Maleimidocaproyloxy]sulfosuccinimide ester), Sulfo-GMBS (N-[g-Maleimido butyryloxy]sulfosuccinimide ester), AMAS N-(a-Maleimidoacetoxy) succinimide ester), BMPS (N EMCA (N-e-Maleimidocaproic acid)-[β-Maleimidopropyloxy]succinimide ester), EDC (1-Ethyl-3-[3-dimethylaminopropyl]carbodiimide Hydrochloride), SANPAH (N-Succinimidyl-6-[4'-azido-2'-nitrophenylamino]hexanoate), SADP (N-Succinimidyl(4-azidophenyl)-1,3'-dithiopropionate), PMPI (N-[p-Maleimidophenyl]isocy, BMPH (N-[β-Maleimidopropionic acid]hydrazide, trifluoroacetic acid salt) anate), EMCH ([N-e-Maleimidocaproic acid]hydrazide, trifluoroacetic acid salt), SANH (succinimidyl 4-hydrazinonicotinate acetone hydrazone), SHTH (succinimidyl 4-hydrazidoterephthalate hydrochloride), and C6-SFB (C6-succinimidyl 4-formylbenzoate). Also, the method disclosed by Letsinger et al. ("Phosphorothioate oligonucleotides having modified internucleoside linkages", U.S. Pat. No. 6,242, 589) can be adapted to form phosphorothiolate linkages.

Further, well established protection/deprotection chemistries are broadly available for common linker moieties (Benoiton, "Chemistry of Peptide Synthesis", CRC Press, 2005). Amino protection include, but are not limited to, 9-Fluorenylmethyl carbamate (Fmoc-NRR'), t-Butyl carbamate (Boc-NRR'), Benzyl carbamate (Z-NRR', Cbz-NRR'), Acetamide Trifluoroacetamide, Phthalimide, Benzylamine (Bn-NRR'), Triphenylmethylamine (Tr-NRR'), and Benzylideneamine p-Toluenesutfonamide (Ts-NRR'). Carboxyl protection include, but are not limited to, Methyl ester, t-Butyl ester, Benzyl ester, S-t-Butyl ester, and 2-Alkyl-1,3-oxazoline. Carbonyl include, but are not limited to, Dimethyl acetal 1,3-Dioxane, and 1,3-Dithiane N,N-Dimethylhydrazone. Hydroxyl protection include, but are not limited to, Methoxymethyl ether (MOM-OR), Tetrahydropyranyl ether (THP-OR), t-Butyl ether, Allyl ether, Benzyl ether (Bn-OR), t-Butyldimethysilyl ether (TBDMS-OR), t-Butyldiphenylsilyl ether (TBDPS-OR), Acetic acid ester, Pivalic acid ester, and Benzoic acid ester.

While the tether is often depicted as a reporter construct with three reporter groups, various reporter configurations can be arrayed on the tether, and can comprise single reporters that identify probe constituents, single reporters that identify probe species, molecular barcodes that identify probe species, or the tether may be naked polymer (having no reporters). In the case of the naked polymer, the reporters may be the probe itself, or may be on a second tether attached to the probe. In some cases, one or more reporter precursors are arrayed on the tether, and reporters are affinity bound or covalently bound following assembly of the Xpandomer product.

In some embodiments, each reporter has a minimum of two states for encoding the base sequence information. Parity or error correction information may also be encoded in the reporters. For example, 9 binary-state reporters could encode the 4 base sequence (2 bits/base) of the associated probe and use the last reporter to encode parity of the previous 8 bits. In another example, three 4-state reporters encode for a three-base probe sequence. In yet further embodiments, template-daughter strand duplexes are disclosed comprising a daughter strand duplexed with a template strand, as well as to methods for forming the same from the template strand and the oligomer or monomer substrate constructs.

In some embodiments, the present disclosure provides a kit useful for SBX methods. The kit may comprise a plurality of constructs (i.e., either Xprobes, Xmers, S-Xprobes or S-Xmers with the appropriate R1/R2 end groups) for forming a daughter strand by a template-directed synthesis, and may optionally comprise appropriate instructions for use of the same in forming a daughter strand. The number of constructs of the kit (which may also be referred to as a "library" of constructs) will depend upon the number of nucleobase residues/construct, as well as the number of universal bases employed as the nucleobases residue(s). For example, such a kit or library of constructs may contain unique members numbering, for example, from 10 to 65000, from 50 to 5000, or from 200 to 1200.

Detection Methods

Synthesis of surrogate polymers is done to facilitate the detection and sequencing of nucleic acids, and is applicable to nucleic acids of all kinds. The process is a method for "expanding" or "elongating" the length of backbone elements (or subunits) encoding the sequence, or partial sequence, information (expanded relative to the small nucleotide-to-nucleotide distances of native nucleic acids) and optionally also serves to increase signal intensity (relative to the nearly indistinguishable, low-intensity signals observed for native nucleotides). As such, the reporter elements incorporated in the expanded synthetic backbone of the surrogate polymers can be detected and processed using a variety of detection methods, including detection methods well known in the art (for example, a CCD camera, an atomic force microscope, or a gated mass spectrometer), as well as by methods such as a massively parallel nanopore sensor array, or a combination of methods. Detection techniques are selected on the basis of optimal signal to noise, throughput, cost, and like factors. The detection methods described herein may optionally employ the fixed and linear array presentation methods described below. Although often described in the context of surrogate polymers for exemplary purposes, the detection methods disclosed herein are equally applicable and useful for detection of nucleic acids in general.

Figure 6:
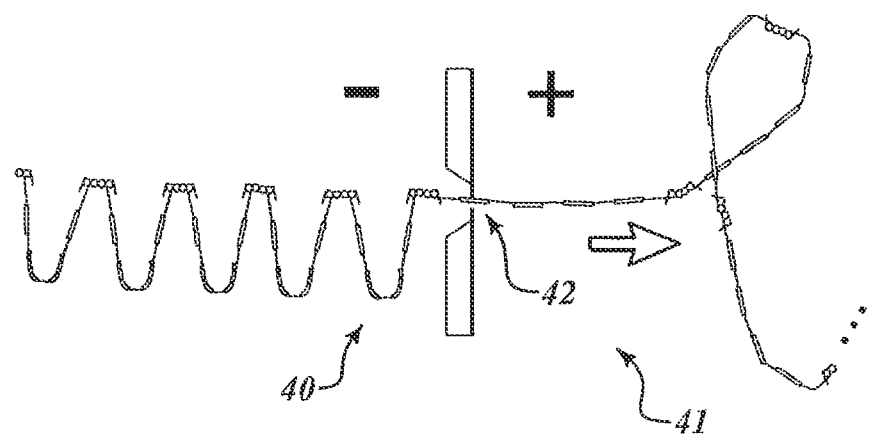
FIG. 6 represents an exemplary nanopore detection technique.

One exemplary detection method is the Coulter-like nanopore process shown in FIG. 6. (It should be noted that these diagrams are not to scale since reporters are anticipated to be >50 times longer than the bases.) The much larger scale of the surrogate polymer reporters relative to native DNA bases enables larger scale, more readily produced nanopores. As depicted in FIG. 6, the nanopore connects two reservoirs (40, 41) that are filled with an aqueous electrolyte solution (typically 1 molar KCl). A potential is applied between electrodes located in each reservoir and a current flows through the nanopore (42). Typically, the surrogate polymer has a negative charge density along its length, and is drawn into the nanopore and is pulled through (translocated) by electrophoretic forces. The nanopore current is modulated by whatever portion of the surrogate polymer that lies within the nanopore channel. In this example, each base type is associated with a reporter type with a unique molecular structure based upon size and/or charge distribution. As each reporter passes through the nanopore, its molecular characteristics alter the current in time and amplitude so the associated base identity can be determined. By capturing this current signal, the sequence information encoded in the sequential reporter constructs is decoded.

Nanopore technology has the potential to serve as a low cost approach to high throughput DNA sequencing. For example, single molecule detection reduces reagent costs and enables long read lengths, and minimal sample preparation eliminates the costs of elaborate template processing and amplification. Rapid DNA translocation rates across the detector (>1 Mbases/s) provides extremely high throughput potential as well as simple low cost single molecule transport. In addition, no chemistry requirement is concurrent with the detection process, thus increasing detection efficiency and decreasing complexity. Finally, simple implementation is utilized that uses direct electrical detection with macro scale electrodes, and low cost instrumentation may be employed that utilizes the power of solid state integration to perform both transport and detection of the DNA sequence.

Figure 7:
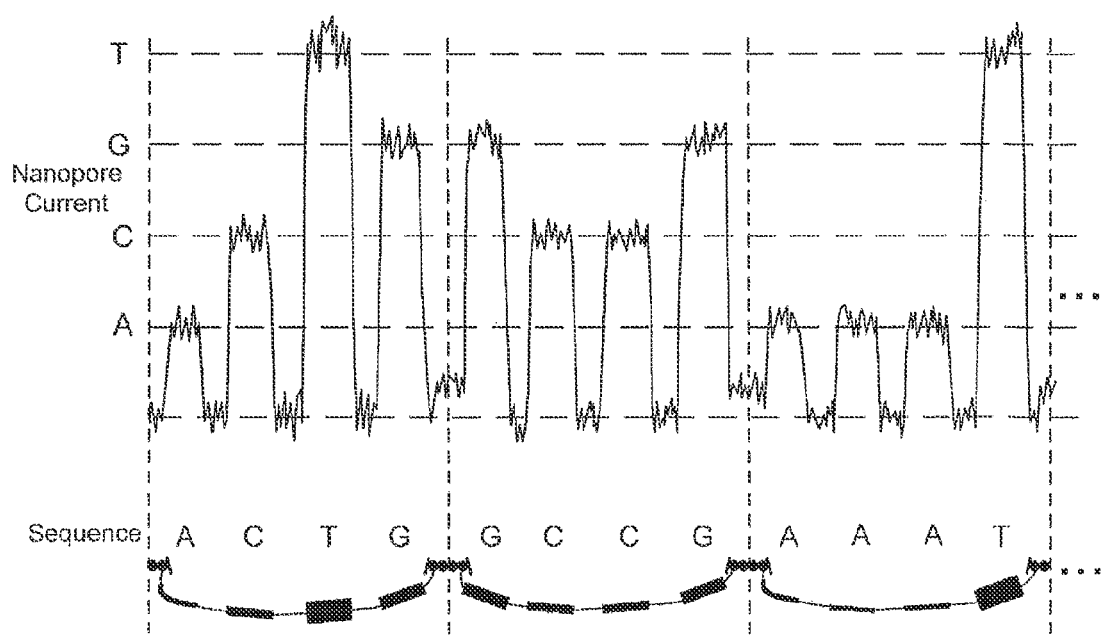
FIG. 7 shows a depiction of a nanopore response as 4 different reporters are passed serially through a nanopore.

Given that ds-DNA is ~2 nm in diameter, reporters designed with molecular cross-sectional diameters of 2, 2.8, 3.5 and 4 nm are believed to give responses in nanopores similar to those shown in FIG. 7. More specifically, FIG. 7 shows a depiction of a nanopore response as 4 different reporters (i.e. reporters encoding A, C, T, and G) are passed serially through the nanopore. (Note that these diagrams are not to scale since reporters are anticipated to be >50 times longer than the bases.)

The surrogate polymer is expected to have higher mass with lower average negative charge and thus will run slower than ds-DNA. Methods to slow the reporter translocation rate include increasing the reporter length, increasing the reporter mass, decreasing the reporter charge density, increasing the reagent viscosity, and/or reducing the translocation potential. Large reporter signals are expected to provide signal-to-noise sufficient for 2-level or higher multi-level coding at detection rates between 10 k to 100 k reporters/s.

A variation of nanopore detection uses optical detection of free fluorescent ions that translocate the nanopore. The advantage of an optical detection technique for nanopores becomes especially relevant for a large nanopore array. An array using Coulter-counting requires each nanopore to be electrically isolated from the next nanopore. Making tiny isolated reservoirs is challenging because the fluids are the conductors. The optical detection techniques disclosed herein allow a nanopore array to share the cis and trans reservoirs (for a common sample) eliminating the need for an array of small reservoirs and the associated fluidics issues. Furthermore, optical detection allows the use of high throughput CCD or CMOS image sensors to measure entire nanopore arrays. Optical detection methods are useful for detection of both surrogate polymers and nucleic acids in general.

Figure 8:
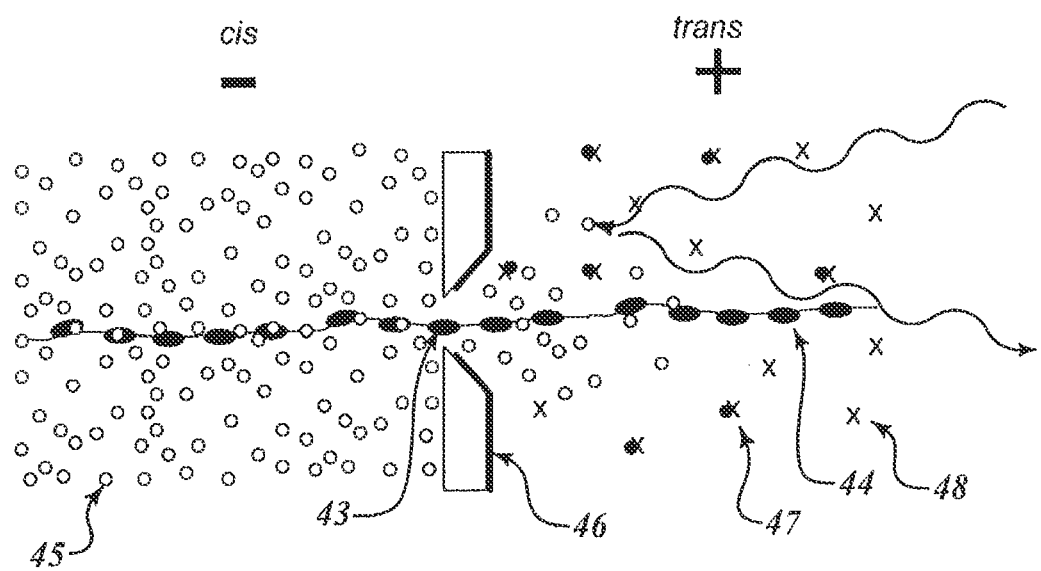
FIG. 8 depicts a nanopore fluorocurrent detection technique.

FIG. 8 shows a nanopore (43) with a surrogate polymer (44) that is passing through the nanopore (translocating). The cis side of the nanopore has a high concentration of fluorophores (45), such as fluorescein (>10 mM). Fluorescein is ~1 nm in diameter and ionizes with a charge of ~−1 elementary charges under weak basic conditions. In a manner similar to Coulter counting, an applied voltage between reservoirs and across the nanopore, drives an ionic current that is limited by the nanopore resistance. For the fluorescein example, its ions consist of a portion of negative ion current that translocates the nanopore. The relative impedance of the reservoirs is balanced by adding other electrolytes such as KCl (at typical concentrations of ~1 mM) to provide adequate conductivity. This electrolyte will also contribute to the ion current and will compete with the fluorophore current if its concentration is too high.

Instead of measuring the current flow, this detection method measures fluorescence of those fluorophores that pass through the nanopore. The fluorophores in the trans reservoir quickly diffuse away from the nanopore opening. As the surrogate polymer translocates the nanopore, it modulates the fluorophore current which in turn modulates the trans side fluorescence.

Fluorescence measurement must limit background noise due to the cis side fluorophores (that are in high relative concentration). One method which uses epifluorescence microscopy for detection limits the background noise by applying a blocking film on the nanopore substrate (46). An exemplary blocking film is a gold film. The film does not need to be up to the edge of the nanopore itself but any holes or gaps in the film should preferably be $\ll \lambda/2n$, the half wavelength of the excitation light in the reagent media (index n). For example, in one embodiment using 480 nm excitation, with n~1.33 (water), gaps must be <<180 nm. A gold film 50 nm thick with a hole 30 nm in diameter centered around the 10 nm nanopore satisfies this criteria and limits transmission of light in both directions across the film and through the gap.

To measure the fluorescence modulation, it is advantageous that the fluorophores have a lifetime in the fluorescence collection volume that is shorter than the rate of modulation. This limited lifetime can be achieved using several different methods. 3D models of the fluorophore diffusion have been conducted that show that the fluorophores diffuse away from the nanopore ~1 micron in the order of milliseconds.

Figure 9:
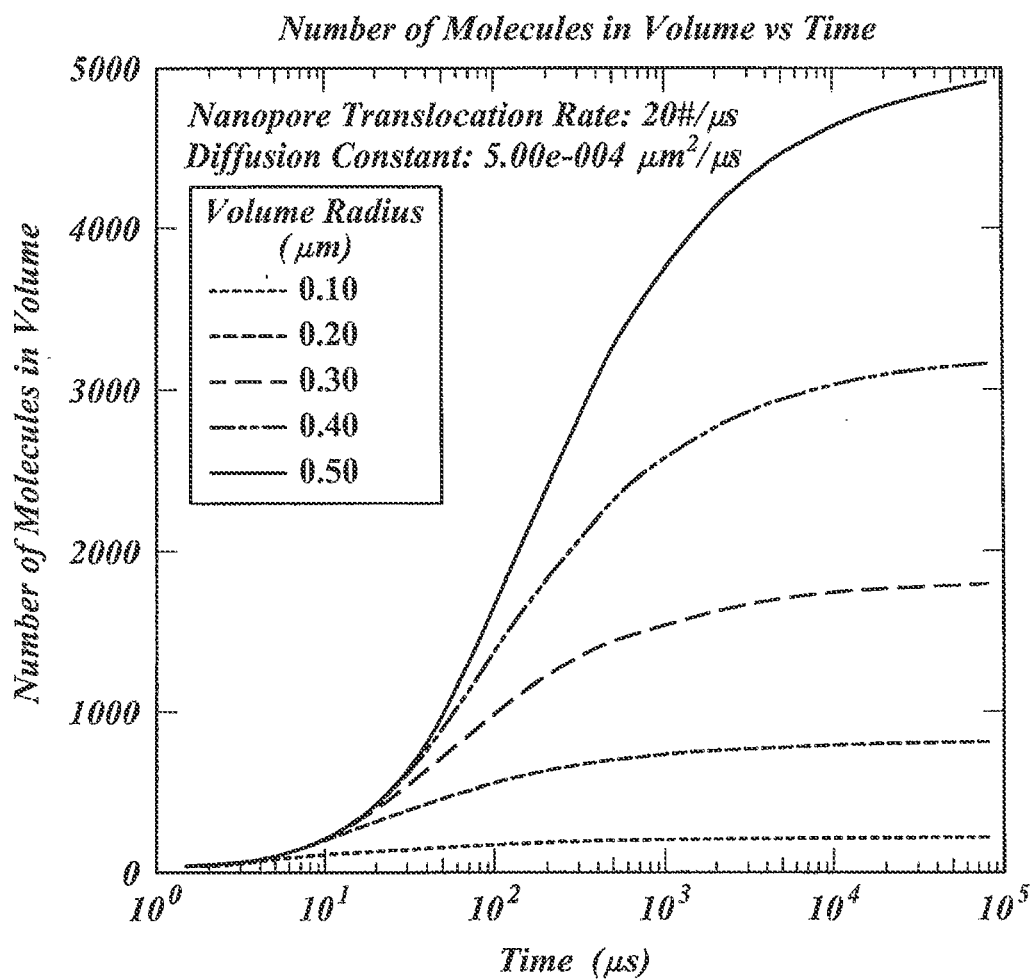
FIG. 9 shows model data of the temporal diffusion of fluorescein into an infinite trans reservoir.

FIG. 9 plots model data of the temporal diffusion of fluorescein into an infinite trans reservoir after translocating a nanopore at 20 molecules/µs. The volumes are defined as the hemispheres centered at the nanopore exit. The fluorophores approach a steady state concentration in each successively larger volume in a successively longer time.

The volume that fluorescence is measured in is limited to a hemisphere centered on the nanopore with a radius ~1 micron or less. The surrogate polymer is translocated through the nanopore at rates slower than 1 ms per base so that the signal level approaches steady-state. In some embodiments, the bandwidth performance may be increased (at the cost of signal) by quenching the fluorophores (as represented by (47) in FIG. 8) with additives (48) after they enter the trans reservoir. Examples of such additives are quenchers (e.g., QSY®7 or QSY®9 available from Molecular Probes/Invitrogen, Carlsbad Calif.) that may be adapted to bind to the fluorophore. Alternately free-radicals that oxidize the fluorophore may be used as fluorescence quenchers. A free radical generator such as azoisobutrylnitrile (AIBN) is a possible source of free radicals. By controlling the concentration of these additives, the time that a fluorophore actively fluoresces inside the trans reservoir can be shortened and background of "old" fluorophores (i.e. fluorophores that have already translocated the nanopore) is reduced.

Figure 10:
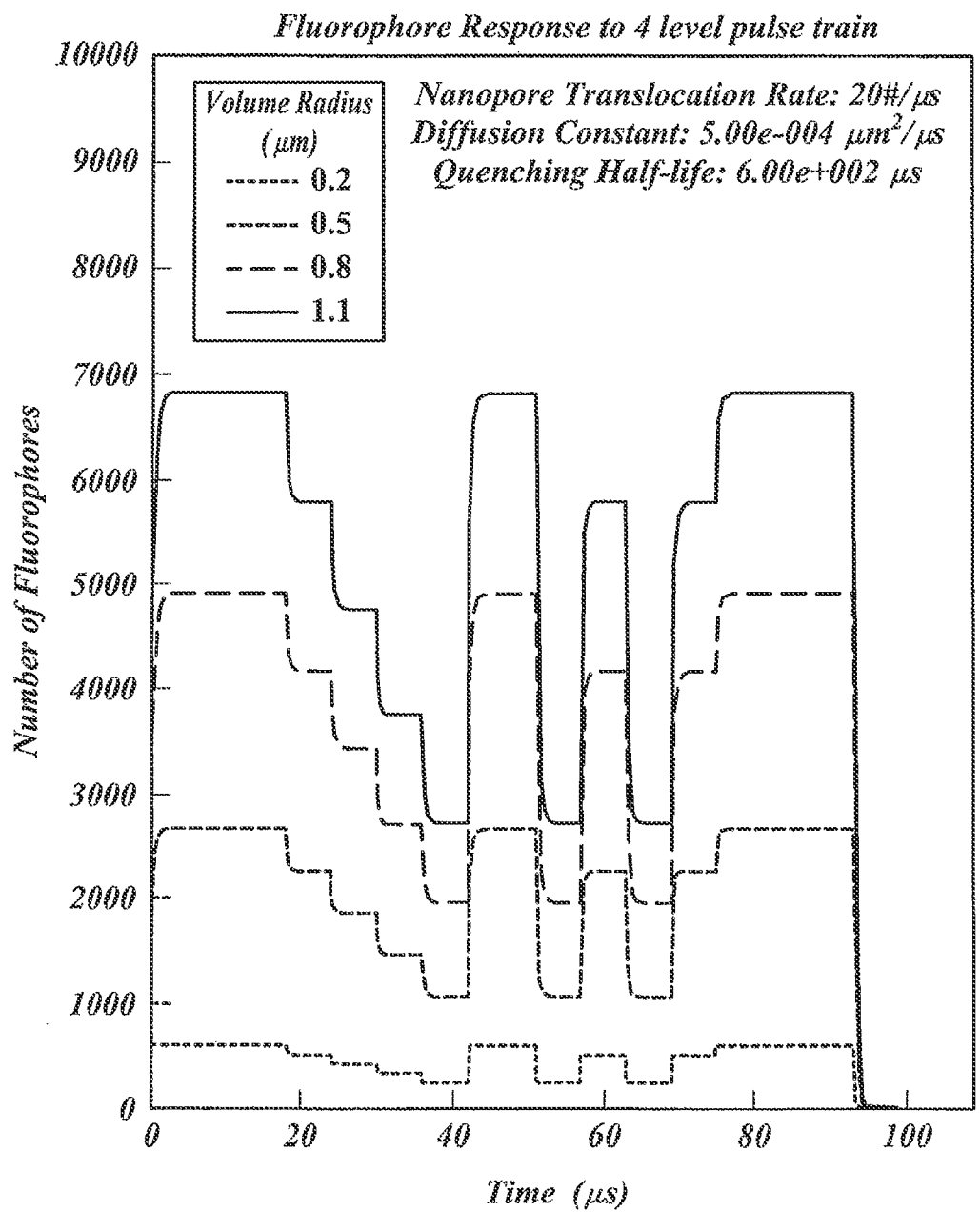
FIG. 10 is a graph showing an exemplary embodiment where fluorophore translocation is limited in time to 5 blocking levels.

FIG. 10 shows graphs based upon an exemplary embodiment where fluorophore translocation is limited in time to 5 blocking levels (20, 17, 14, 11, and 8 fluorophores/us). The fluorophores diffuse away but are quenched randomly throughout the reservoir with a half-life of 600 µs. This action of quenching reduces the number of fluorophores there are for signal but also limits the measurement volume and establishes a faster time to steady-state (at each level).

In another embodiment, a method of eliminating the fluorescent background comprises designing the detector so as to only view a limited volume at the nanopore exit. Conoscopy is one such exemplary method. The advantages of an optical detection method are that the fluorophore current can be a highly amplified signal. For example, in contrast to non-optical methods, the nanopore array can be very high density because it does not require reservoirs to be isolated between nanopores. In addition, the measurement is well suited to a simple single color epifluorescent microscope and takes advantage of the advances in high speed cameras. The fluorescent background can be further reduced by employing a nanopore substrate comprising a blocking film. Exemplary blocking films for this purpose include gold films.

Figure 11:
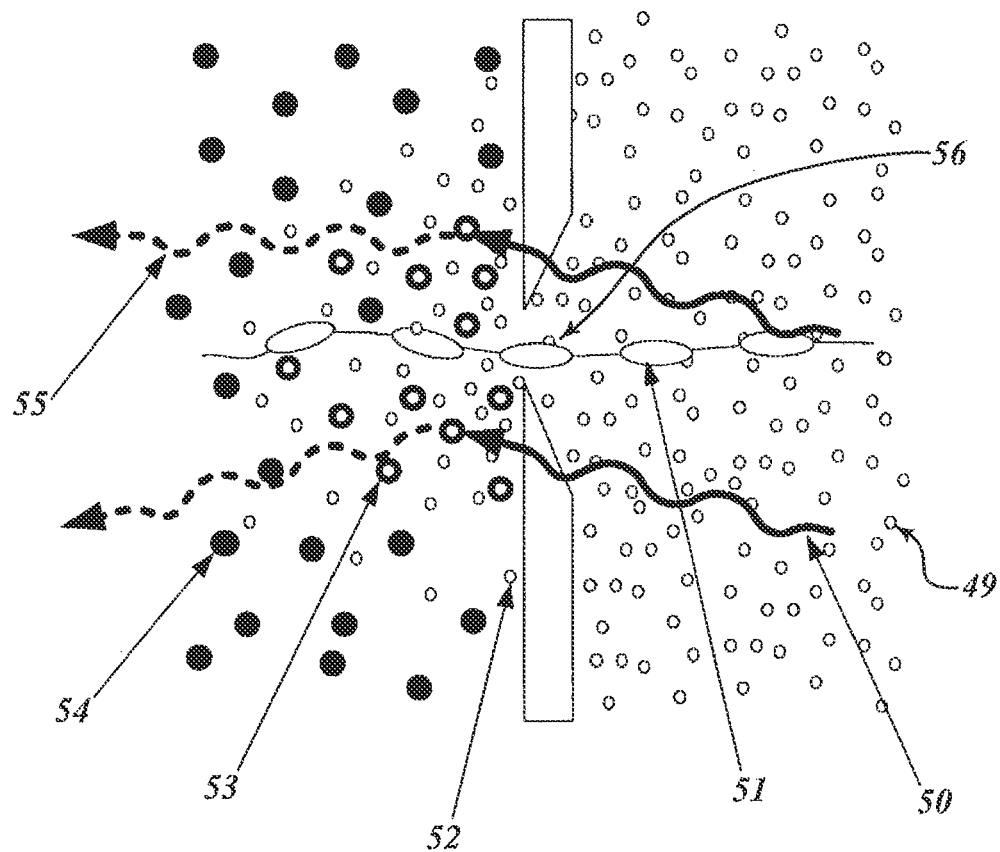
FIG. 11 depicts an ion indicator detection method.

Another exemplary embodiment for reading the reporter constructs of the surrogate polymers is ion indicator detection. FIG. 11 depicts an example of ion indicator detection. This is a nanopore variant that uses excitation light (50) and an ion selective indicator molecule (54) to produce a fluorescent signal (55). The signal amplitude depends upon the number of indicator ions that translocate the nanopore (56). In FIG. 11, the indicator ions (49) are loaded on the cis reservoir and indicator molecules are loaded on the trans reservoir. The indicator ions translocate the nanopore by both entropic and electric field forces. The rate of their translocation depends upon the blockage state of the nanopore. Surrogate polymer reporters are designed to provide different blockage states. Once the indicator ions have translocated (52), the indicator molecules will couple to them (53) and alter their fluorescent emission characteristics (55).

For example, in one ion indicator detection embodiment, the indicator ion $Ca^{+2}$, will couple to the indicator Fura-3 (available from Molecular Probes/Invitrogen, Carlsbad Calif.), and, under UV excitation, the emission at ~520 nm increases by 40×. As the surrogate polymer translocates through the nanopore each reporter limits the rate $Ca^{+2}$ ions will translocate and changes the ion distribution on the trans reservoir side. The indicator located in the trans reservoir couples to the $Ca^{+2}$ ion and increases fluorescence. For a given $Ca^{+2}$ translocation rate, the measured fluorescence level reaches a steady state because the rate that new fluorescing $Ca^{+2}$/indicator compounds are created equals the rate of them dissociating and/or diffusing out of the measurement volume. Unlike the fluoro-current method described above, there is no fluorophore or absorber in the cis reservoir, which means the volume at the nanopore exit (i.e in the trans reservoir side) can be illuminated from the cis side to excite the fluorophores. As with the fluoro-current approach above, the ion/indicator couplet diffuses away from the nanopore and steady state is established in the least time (<1 ms) in a small volume close to the nanopore (<1 um).

To limit the measurement volume to this small volume, two exemplary methods may be used. A nonfluorescing absorber in the trans reservoir will absorb the excitation light exponentially with depth into the reservoir to limit the measurement depth. An epi-illumination microscope can be used to spatially delineate the lateral dimensions of the volume.

In an alternative embodiment which also uses an epi-illumination microscope, the volume can be delineated by masking a small opening (<1 um diameter) centered on the nanopore. This limits most of the fluorescence collection to the small unshadowed volume at the nanopore exit.

Other exemplary indicators useful in this method include Fluo-3, Indo-1, and Fura Red (available from Molecular Probes/Invitrogen, Carlsbad Calif.). Other exemplary ion indicators that can be used in, this method include but are not limited to, ions of singlet hydrogen, singlet oxygen, potassium, zinc, magnesium, chlorine and sodium, all of which have commercially available fluorescence indicators (available from Molecular Probes/Invitrogen, Carlsbad Calif.).

Figure 12:
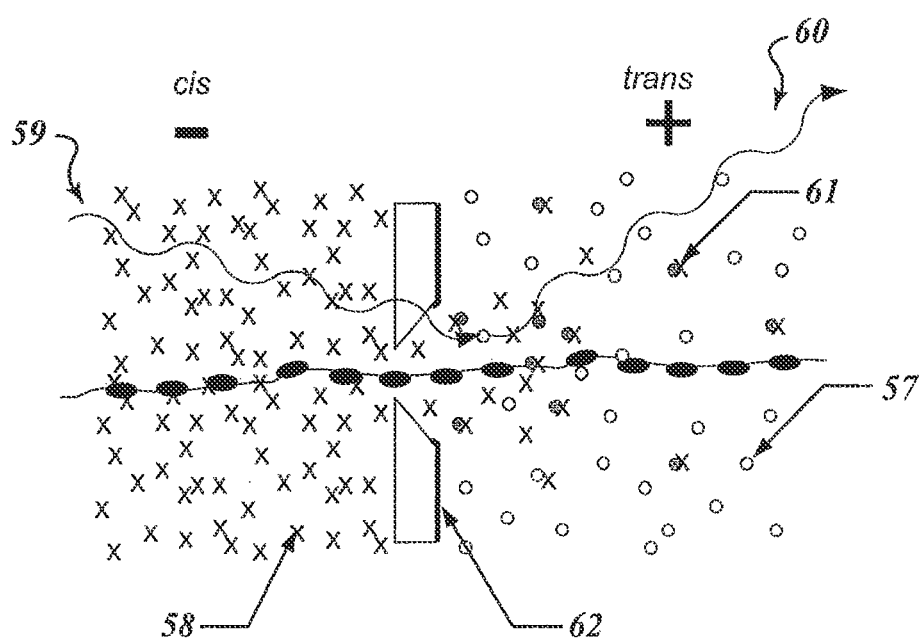
FIG. 12 shows a quenching fluorescence detection method.

In another embodiment, quenching instead of enhancement is used. FIG. 12 illustrates this quenching fluorescence approach. As shown in FIG. 12, fluorophores (57) are present in one reservoir and a quencher (58) is present in the other reservoir. As quencher flows through the nanopore, it is in highest concentration at the nanopore and drops to lower concentration as it diffuses away from the nanopore. Excitation light (59) causes the fluorophores to fluoresce (60), but this fluorescence is quenched (61) in proportion to the concentration of quencher. The nanopore substrate may optionally comprise a blocking film (62). A non-limiting example of a blocking film is a gold film.

In an exemplary embodiment of the above, fluorescein may be loaded at ~10 mMolar concentration on the trans reservoir and iodide ion may be loaded at ~1 Molar concentration on the cis reservoir. Iodide can translocate the nanopore in ~nA levels leading to concentrations of iodide near the nanopore that act as quenchers to the excited fluorescein (excited with 488 nm light). By using epi-illumination with fluorescence capture from the cis reservoir side and masking around the nanopore, fluorescence may be collected from a small volume (<1 µm$^3$) within the trans reservoir. The level of blocking in the nanopore establishes the level of fluorescence quenching and provides the signal for decoding the sequence information.

In another embodiment, translocation blockage level can be measured using chemiluminescence. This method employs two species, A and B, which are capable of combining to form an excited state compound C'. A and B may be loaded into the cis and trans reservoirs respectively, if either species translocates the nanopore, it will react and form C'. When C' returns to the ground state, it emits a photon. The intensity of the photon emission may be used as a measure of the nanopore blockage. Non-limiting examples of chemical species useful for this method include luminal/peroxidase and luciferin/luciferase.

In another embodiment, Fluorescence Resonance Energy Transfer (FRET) detection may be used. An exemplary FRET detection embodiment employs an array of pores (PXp). In this embodiment, the surrogate polymer is assembled using the methods described herein. Surrogate polymer reporters are loaded with FRET donor fluorophores, for 1 to 4 excitation wavelengths. The FRET acceptor fluorophores are tethered to the porous node entrance. As the surrogate polymer is translocated through the porous node its donor fluorophores are excited with a light source, and as the reporters pass proximal to the acceptor fluorophores at the nanopore entrance, the acceptors are excited and emit their signature fluorescence. These emissions are decoded into the associated nucleotide sequence. Emissions can be modulated by wavelength, ratio of wavelength, strength of emission, length of emission or a combination of these.

Figure 13A:
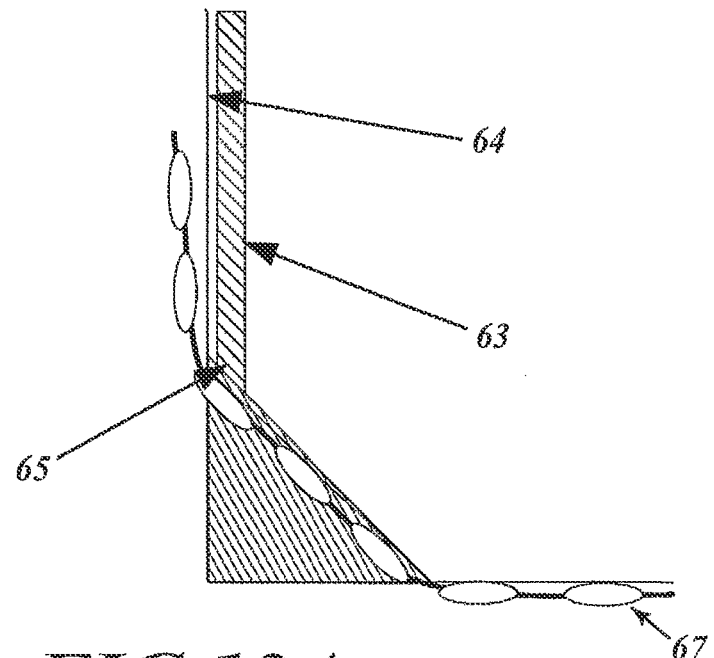
FIGS. 13A and 13B illustrate a nanocomb detection technique.
Figure 13B:
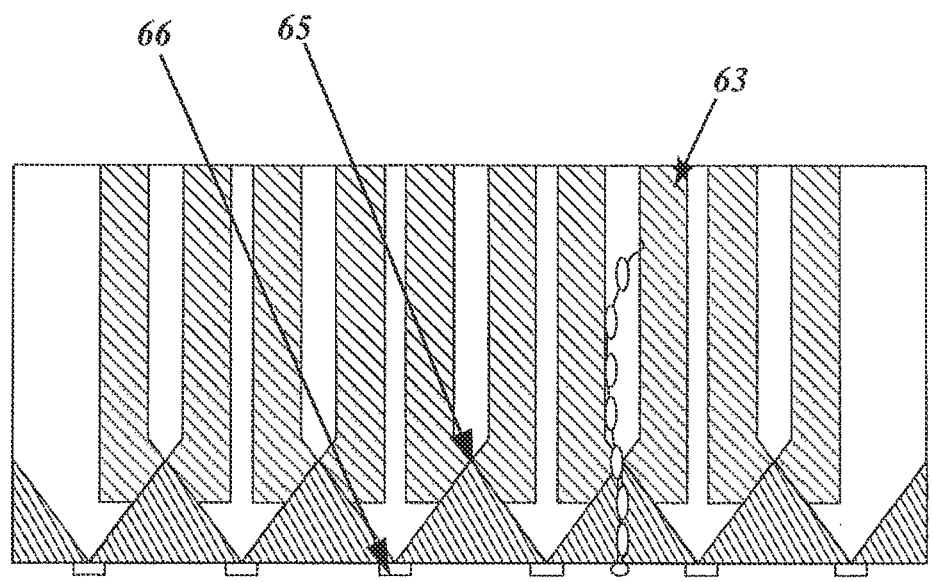

In another embodiment, a nanocomb detector array may be employed. As described in more detail below, a nanocomb performs a presenting function by capturing and guiding tethered surrogate polymer into the bottom of its channels, but it also comprises a means of detecting the surrogate polymer. An exemplary embodiment is depicted in FIGS. 13A and 13B. The nanocomb comprises a pair of lateral electrodes (63), between which the surrogate polymer (67) passes, an insulating layer (64), and a spacer (66). The detector is located in or at the end of the nanocomb slot through which the surrogate polymer is guided (65). The detector "reads" the reporter elements as the surrogate polymer is drawn past. Modes for reading the reporter elements include, but are not limited to: 1) the electrolyte current is blocked by the surrogate polymer reporters (Coulter Mode), or 2) the reporters are conductive, and a current path is formed between the two electrodes. In some embodiments, Reporters with conductive polymers at different densities are employed. The reporters short the two electrodes at the slot intersection of the electrode pair with different impedances which can be decoded into the surrogate polymer's parent DNA sequence.

The scale of the nanocomb detectors and the reporters require that the surrogate polymer position be tightly controlled. Thus, the nanocomb must be manufactured in a manner such that the desired control can be achieved. For example, the channels or troughs of the nanocomb are the intersection of two crystal planes. By using anisotropic silicon etching, the bottom of the nanocomb's troughs can be defined very sharply to <10 nm radius. The nanocomb detector element is preferentially located near the junction of the wafer surface and each trough, thus, it can be formed by use of thin films and conventional wafer processing. One exemplary method of creating the two electrodes uses two overlayed thin films whose intersecting edges define the asymmetric etch mask for the silicon. Shadow coating of a conductive metal (e.g., Au) on these films produces two electrodes that are separated by the shadow and film thickness. In some embodiments, further masking may be required to further define the conductive electrodes.

In some embodiments, a direct means of "reading" surrogate polymers presented in a linearized array uses electron beam microscopy. Electron beam microscopy (e.g. Scanning Electron Microscopy (SEM)) is capable of ~1 nm resolution, and a large number of different techniques have been developed for different applications. In this embodiment, throughput is of high importance whereas resolution can be compromised. For example, because the surrogate polymers are ordered along a single axis in the linearized array, the electron beam does not require resolution normal to the surrogate polymer backbone and can be broadened in this dimension to form a line rather than a spot focus.

With a line focus the electron beam is scanned along the surrogate polymer backbone axis for data capture. The length of the line electron beam is limited by the background noise it produces. This background noise degrades the signal emitted by the surrogate polymer (i.e., reduces signal-to-noise ratio (SNR)). The advantage of the long line electron beam is the reduced requirement for lateral positioning. In some embodiments, materials such as boron or nanogold in the reporters provides large scatter cross-sections to the electron beam for high contrast signals. In some embodiments, the SEM beam angle can be optimized to improve the SNR.

In some embodiments, conventional post processing, for example, by deposition of high contrast coatings, such as gold films, to the linearized array can provide enhanced SEM contrast. Other thin film techniques including shadow deposition, electrodeposition, vacuum deposition and etching can be used to enhance the SNR of the surrogate polymer in the electron beam measurement.

Figures 14A, 14B:
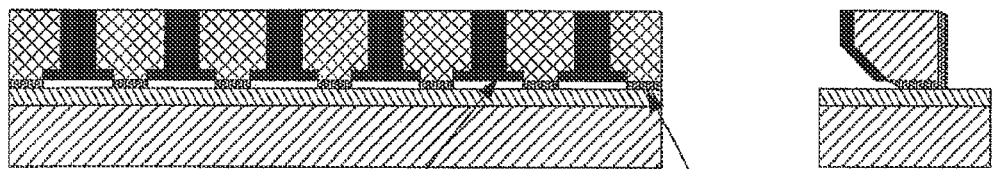
FIGS. 14A, 14B, and 14C show a detection method comprising a knife-edge electrode and conductive polymer.
Figure 14C:
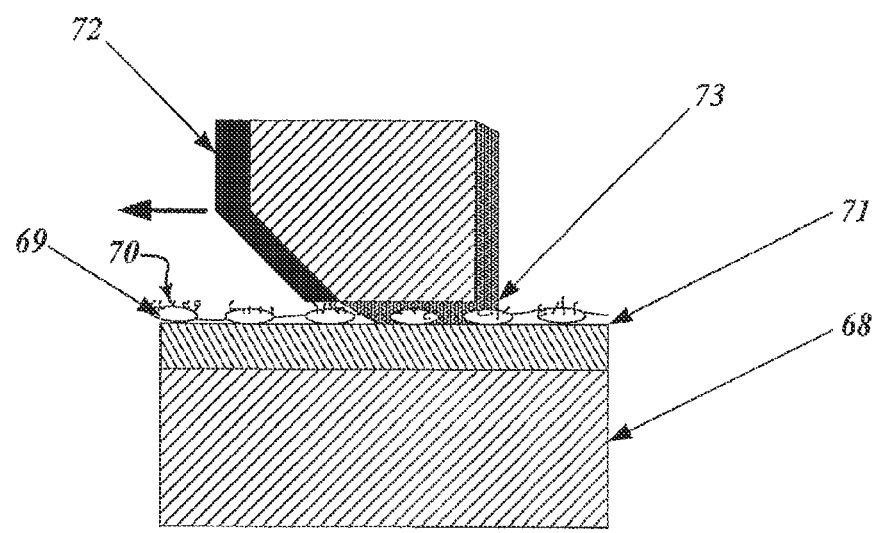

In some embodiments, knife-edge conduction may be used for detection of the surrogate polymers. In these embodiments, the surrogate polymers comprise one or more brush polymer reporters, wherein the brush polymer reporters comprise conductive polymeric bristles. FIGS. 14A-C illustrate an exemplary multichannel knife-edge detector which slides along a linearized array substrate (68). Surrogate polymers (69) comprising brush polymer reporters (70) are presented on the linearized array aligned and spaced apart by the pitch of the detector channels. They are in electrical contact with a conductive ground plane (e.g., gold film (71)) of the linear array substrate. A knife edge electrode (72), normal to the surrogate polymer backbone axis, is positioned above the substrate ground plane by a ~10 nm gap, formed by friction spacers (73) along each side of the gap. An electric potential is applied between the knife-edge electrode and the linearized array ground plane. As the detector slides along the substrate, the surrogate polymer reporters sequentially pass under the knife-edge electrode. The conductive polymer bristles of the reporter act under the influence of the electric field bridge to make contact and complete an electric circuit between the knife-edge and the ground plane. The electric current provides the measured signal. The reporters may be selected to have different impedances or different lengths thus generating distinguishable current signatures for decoding the surrogate polymer information. An exemplary method of distinguishing different impedance levels is to use different conductive bristle densities. Non-limiting examples of conductive polymers include polyacetylene, polyaniline and polypyrrole.

In an alternative embodiment, fluorescence microscopy may be employed for surrogate polymer detection. The surrogate polymer is labeled with fluorophores of one, two or more spectral types. One example is to use two fluorophores with different spectral emissions, red and green for example. Each of the four nucleic base types can be uniquely identified using four emission states: (1) Red only, (2) Red>Green, (3) Green>Red, and (4) Green only.

To maintain high information density but practical fluorescence capture, the surrogate polymer may be presented in a dense parallel aligned packing arrangement with separations of ~1 micron. A sensor with 10 micron pixels and a 40× objective provides 250 nm/pixel resolution (or 4 pixels intersurrogate polymer separation). To resolve reporters their minimal separations are ~200 nm. This can be further reduced by invoking near field, zero mode, STORM or FRET/Quench methods for more localized detection.

In another embodiment, an optical near field method using slits instead of capillaries can be used to localize the excitation energy to <100 nm along the surrogate polymer axis. The near field source that emerges from the slit is used to excite fluorophores of the surrogate polymer reporters and fluorescence is detected in the far field. As the slit array is scanned along the linearized array and along the axis of the surrogate polymer, the measured fluorescence can be deconvolved to produce the surrogate polymer sequence information.

Presentation Methods

The SBX process produces an enriched product of surrogate polymer that is then presented to the detection instrument to "read" the reporter sequence. Exemplary detection methods include those discussed above and other detection methods known in the art. To improve the performance of the detector, the surrogate polymer product can be further processed for presentation to the detector. For example, in some embodiments, the charge characteristics of the surrogate polymer may be engineered to be similar to a native DNA polymer. Exemplary presentation methods include molecular gating, spatial confinement, flow control, channelizing, substrate bonding and thin film processing enhancements. For exemplary purposes, the methods disclosed herein are often illustrated and discussed with reference to surrogate polymers, however, the disclosed presentation methods are equally useful for nucleic acids in general.

An important characteristic for detection and measurement of reporters is to have uniform spatial and temporal spacing of the reporters presented to the detector. For this to happen it is advantageous that the surrogate polymers be extended and positioned appropriately. A hairpin fold places a high burden on the detector to distinguish two portions of a labeled strand simultaneously and leads to lowered detection efficiency. In a related issue the surrogate polymer should have either an inherent stiffness or a tension along its length to prevent adjacent labels from bunching. This characteristic helps to maintain the reporter-to-reporter spacing and maintain reporter resolution. In a final related characteristic, the speed at which the surrogate polymer is presented to the detector should be uniform and smooth. Temporal variation in presenting the reporter reduces the detector efficiency because it must sample for the fastest exposure requirement, whereas the throughput depends only on the average exposure requirement. The embodiments disclosed herein, address these needs and provide further advantages.

Non-limiting examples of methods of presenting the surrogate polymer to the detector include: (1) in-flow, (2) tethered to a solid substrate, and (3) aligned on a substrate surface. FIG. 14 illustrates this concept. FIG. 15A illustrates surrogate polymers presented in-flow in both a random and ordered (e.g. gated) fashion. The arrows indicate the direction of surrogate polymer flow. FIG. 15B illustrates surrogate polymers presented tethered to a solid substrate in both a random and ordered (e.g. arrayed) fashion. Finally, FIG. 15C illustrates surrogate polymers presented aligned on a substrate surface in both a random and ordered (e.g. arrayed) fashion.

An example of the "in flow" presentation is when surrogate polymer flows to and through a nanopore detector. By this detection technique, two to four reporter types can provide a corresponding number of current levels with which to encode base sequence information and can be detected at throughput rates of 10 to 1000 kReporters/s. For sequencing throughput >1 Gbases/hour, parallelization of the nanopores is required.

Figure 16:
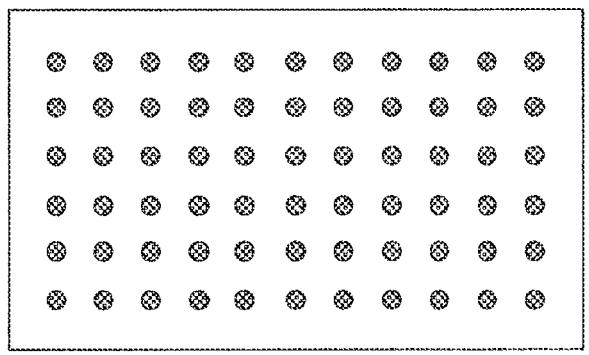
FIG. 16 shows a porous array on a substrate.

FIG. 16 shows a substrate having an array of pores (called a PXp) useful for in-flow presentation methods. The substrate comprises a regular array of nodes each of which has one or more pores. When the array has a single pore at each node, it is a nanopore array (NXp). As discussed above, nanopore channels can be configured to comprise a detector element. Thus, the array depicted in FIG. 16 provides a possible method for parallel detection of surrogate polymers.

In an exemplary embodiment, each nanopore channel of a NXP is configured to allow detection of a surrogate polymer. In this embodiment, the concentration of surrogate polymer must be controlled to maximize the efficiency of the nanopore channel. Surrogate polymers arrive at the detector randomly in time with 0, 1, 2 or more surrogate polymer arrivals occurring over any set time period. According to Poisson statistics, over a given sampling period, a maximum of ~37% of the periods will have a single surrogate polymer arrival. The rest of the periods will have 0, 2 or more arrivals. This percentage of single surrogate polymer per channel is further reduced when overlapping of the adjacent surrogate polymer is accounted for. Modeling of the case where all molecules have equal length and velocity but have random arrival times indicates that only 18% of the read time will produce complete nonoverlapped reads. An ideal scenario is to have single molecules line up head-to-tail so the detector sees no gaps and always sees a portion of a single molecule.

In the above embodiment, some of the surrogate polymers may be in a folded condition which lowers the efficiency even more (assuming the detector can only distinguish unfolded surrogate polymer). Solubility and mobility limits of long surrogate polymers can further limit fill efficiency because even at maximum solubility concentrations, the surrogate polymer may not fill the nanopores fast enough to reach 18% fill. Thus, there remains a need in the art for in-flow presentation methods which optimize the efficiency of nanopore array detectors. Exemplary embodiments disclosed herein overcome the problems associated with nanopore array detection and provide further advantages.

Figure 17A:
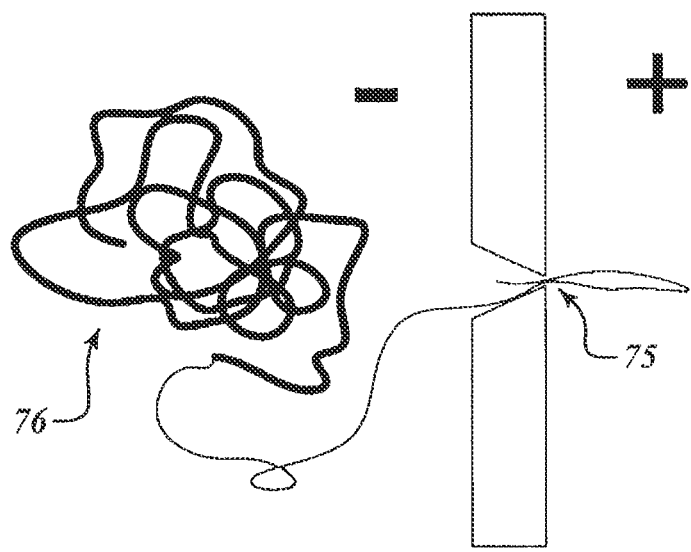
FIGS. 17A and 17B illustrate an exemplary presentation method.
Figure 17B:
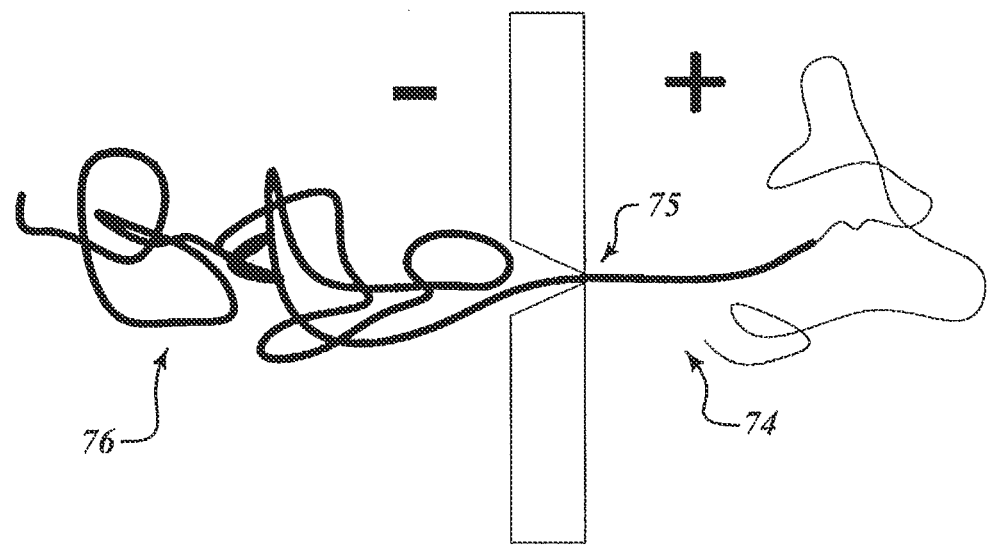

In one embodiment, adding a charged, long linear polymer having a low molecular weight to the end of the surrogate polymer can assist in threading the surrogate polymer because of the polymer's higher mobility and charge density relative to the surrogate polymer itself. For example, a polymer having a linear charge density and/or the same charge state as DNA (i.e. negative) can be attached to the end of the surrogate polymer. As depicted in FIGS. 17A and B, the end of such a polymer (74) would be drawn into a nanopore (75) with much higher efficiency in either a folded or unfolded state, translocating ahead of the surrogate polymer (76) and pulling it into the nanopore. Non-limiting examples of highly negatively charged, low linear density polymers include: polyglutamic acid and polyphosphate. To further increase the probability of threading the nanopore, one embodiment employs multiple polymers attached to one or both ends of the surrogate polymer. The length of the polymer is optimized to maximize the threading probability, but must not significantly interfere with the surrogate polymer measurement. In some embodiments, the polymers can be microns in length.

Increasing the potential across a nanopore can improve performance of fill. Thus, in one embodiment, the nanopore current is actively monitored, and the voltage can is increased (thereby increasing the nanopore fill efficiency) until a threaded surrogate polymer is detected and then decreased to the desired measurement voltage until the surrogate polymer measurement is completed. The voltage is then increased again, until the next surrogate polymer is threaded.

In some embodiments, read efficiency is increased by actively switching the detector (e.g. current measurement electronics in the case of Coulter-like nanopores) to an array of nanopores that is already filled with surrogate polymers in a ready-to-measure state. When measurement is completed the detector is switched to another array of prefilled surrogate polymers. In some embodiments, prefilling may be performed offline with enough nanopore arrays to complete the whole sequencing job. In other embodiments, prefilling can be a real time function whereby prefilling is occurring on one or more arrays while measurements are being made on another array.

Figure 18A:
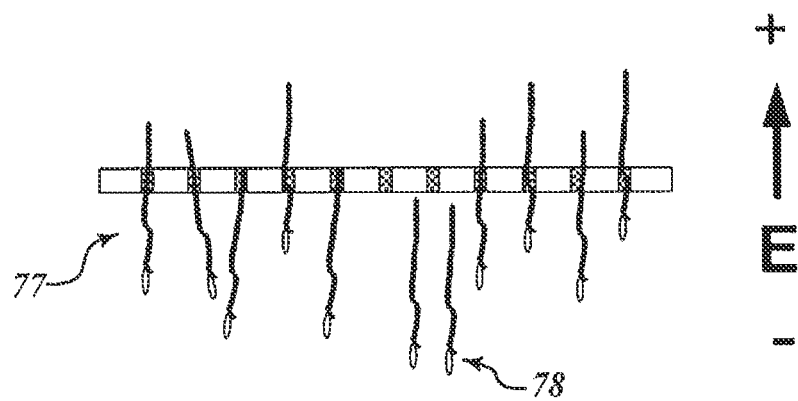
FIGS. 18A, 18B, and 18C depict exemplary presentation methods.
Figure 18B:
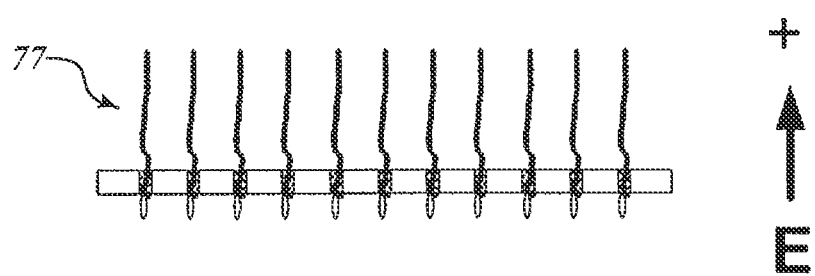
Figure 18C:
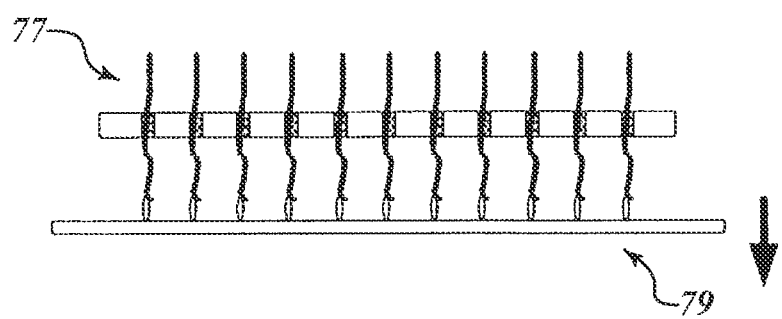

FIGS. 18A through 18C illustrate the prefill concept. In the illustrated embodiment, surrogate polymers (77) are first adapted to have a stop (78) which prevents the surrogate polymer from passing through a nanopore but allows them to be threaded. Non-limiting examples of stops include beads and bulky dendrimers. To adapt to a bead stop, a linker at the end of an surrogate polymer is reacted with appropriate chemistry on the bead surface under low surrogate polymer concentration and high bead concentration. Beads are collected and washed to remove unreacted surrogate polymer. Next, unreacted beads are removed under electrophoretic fields that filter out bead-attached surrogate polymers. The bead-adapted surrogate polymers are now threaded into the nanopore array by applying a voltage across the pores (depicted in FIG. 18A as electric field E). Under dilute conditions the surrogate polymer will thread singularly through the nanopore up to the stop (e.g., bead). The stop is pulled against the nanopore by the translocation force due to the electric field acting on the charged surrogate polymer and seals the nanopore, preventing additional surrogate polymers from threading through the same nanopore. This continues until the nanopores each have a single surrogate polymer (FIG. 18B). The array can now be measured by reversing the voltage, driving the surrogate polymer in the opposite direction and collecting the measurement sequence (e.g., current).

In an alternative embodiment, mechanical force may be used for translocation. This embodiment is illustrated in FIG. 18C where the surrogate polymers are pulled through the nanopores by their ends being attached to a substrate (79) that is lowered.

Figure 19A:
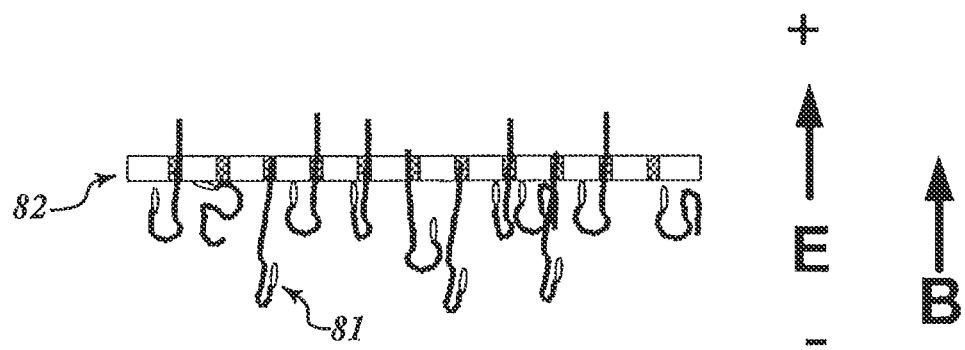
FIGS. 19A, 19B, and 19C depict exemplary presentation methods.
Figure 19B:
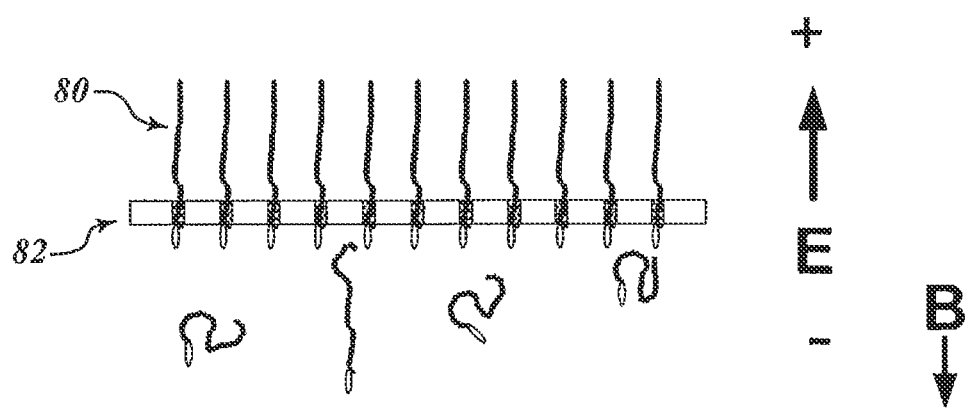
Figure 19C:
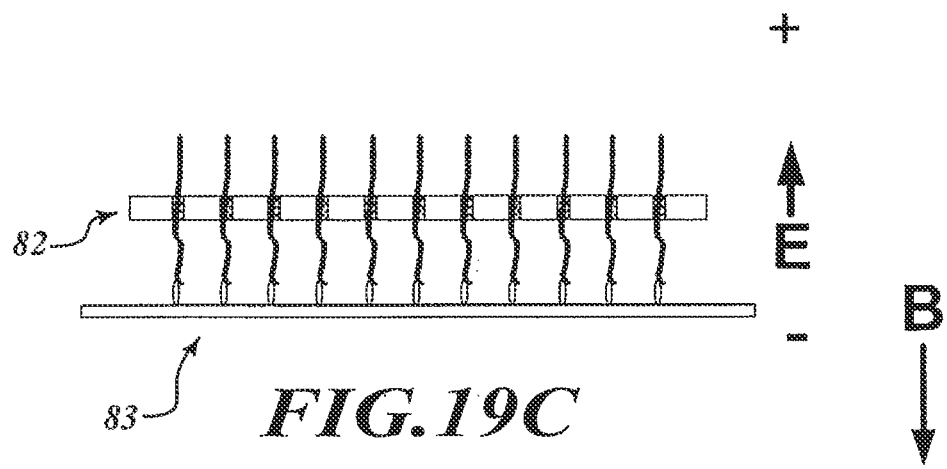

In another embodiment, a magnetic bead stop provides additional functionality. As illustrated in FIG. 19A, the surrogate polymer (80) may comprise a magnetic bead (81) attached to one end. Under a magnetic field, B, the beads are driven to the nanopore array surface which increases the concentration and probability of threading. After the surrogate polymer has threaded through the nanopore and is pinned in the nanopore by the applied electric field, E, the surrogate polymers that are not threaded into nanopores can be drawn away by applying a low magnetic field in the reverse direction as shown in FIG. 19B. By further increasing the magnetic field (and adjusting the applied electric field as required), the surrogate polymer can stretch and it will translocate through the nanopore in either direction depending upon which force dominates. If the magnetic force dominates, the nanopore translocation has velocity irregularity due to Brownian motion. Using a platform (83) that moves slower than the magnetic bead velocity, as shown in FIG. 19C, the translocation velocity can be uniformly controlled across the nanopore array.

In another embodiment, a linear ferrite polymer leader can be adapted to the end of the surrogate polymer instead of a magnetic bead. The linear ferrite polymer leader can be used to move (or stretch) the surrogate polymer much like the magnetic bead but can still translocate the nanopore.

Several different gating techniques are described herein and generally share a common characteristic. In each case, single surrogate polymer molecules are released to flow towards the detector on a regular period. The period is chosen so that as the detector finishes the sequential reading of reporters on one surrogate polymer molecule another one enters the detector and thereby maximizes the duty cycle of the detector.

Figure 20A:
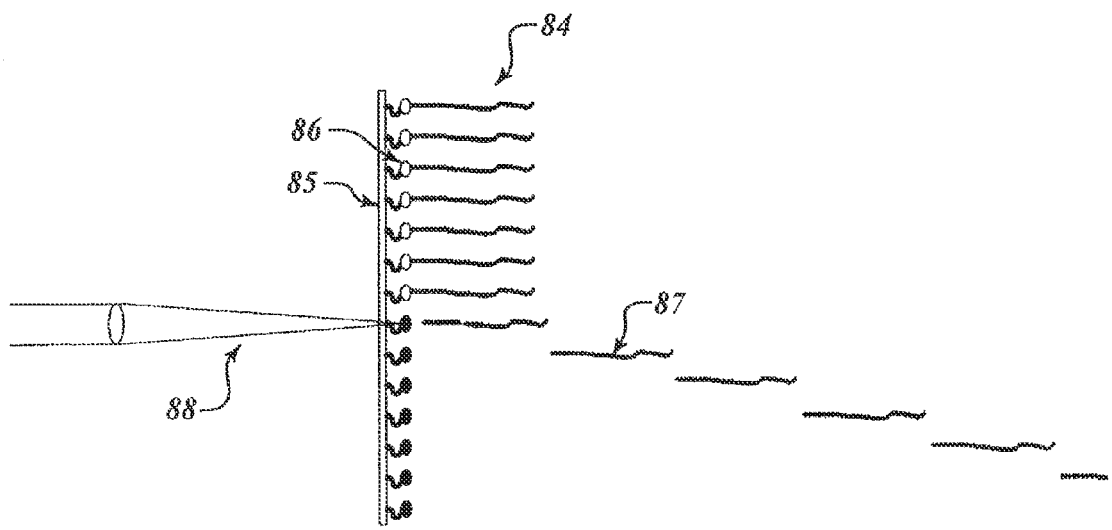
FIGS. 20A through 20D depict exemplary presentation methods.

In one embodiment, gating of the surrogate polymers is accomplished by timed release of the surrogate polymers from a substrate. Referring to FIG. 20A, the surrogate polymers (84) are tethered to a substrate (85) in a manner such that their positions are known or can be determined. For example, filling a regular grid with one tethered molecule per grid space is one embodiment. Another example is to place them randomly but with suitable separation and with a fluorescent label so they can be located. The tether is chosen to have an addressable cleavable coupling (86) so that the surrogate polymer can be released (87) on demand. Exemplary methods of addressable cleaving include: (i) photocleavable links using a directed light source such as a focused laser beam (88), (ii) thermally released links where local heating is achieved by addressable resistors or a laser, and/or (iii) electrochemical links where addressable electrodes can drive redox reactions.

Figure 20B:
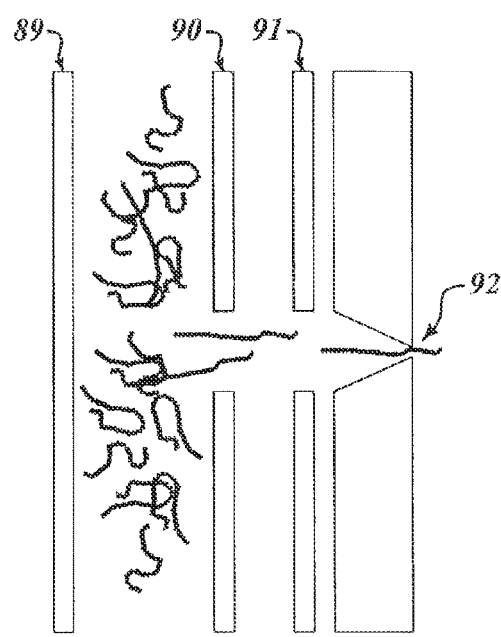

FIG. 20B illustrates another embodiment referred to as electrical trapping or electrode gating. In this embodiment electric fields (i.e. electrodes 89, 90, and 91) are placed in front of the detector (92) to repel the surrogate polymer from the detection area when a molecule is in the detector and is being "read". When the molecule is read (or near completion of the read), the gating field is reversed and the surrogate polymer that is in solution in front of the detector is attracted to the detector. As soon as one enters the detector, the gate electric field is again reversed to repel the other surrogate polymers. It is necessary to maintain gate fields low enough so that the surrogate polymer in the detector does not get drawn back by the repulsive gating force.

Figure 20C:
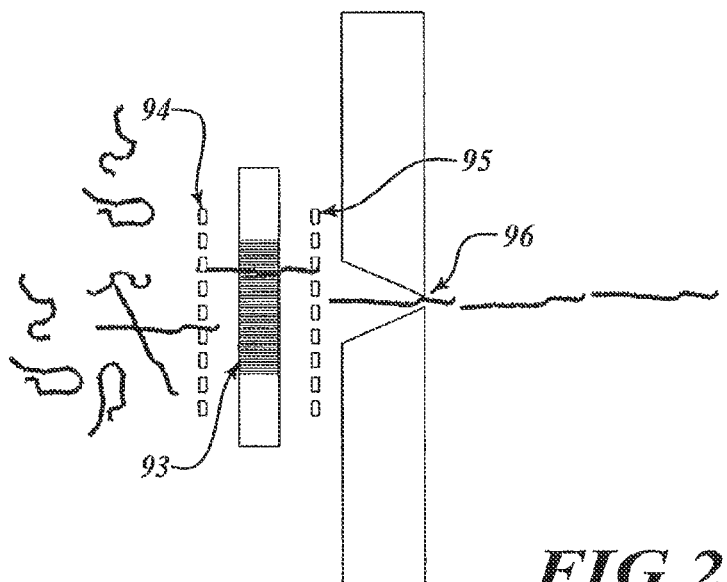

FIG. 20C illustrates another gating embodiment referred to as membrane gating. This embodiment shares features of the previous embodiments but also comprises features that help stretch out the surrogate polymer and to filter those surrogate polymers that are knotted or clumped. This embodiment employs a thin filter membrane (93) that has pores on the order of 20-100 nanometers. Exemplary membranes include an aluminum oxide porous membrane and a polymer track-formed membrane.

Referring again to FIG. 20C, porous electrodes (94, 95) sandwich the membrane. When a field is applied between the electrodes, the surrogate polymer is transported by electrophoresis. As it enters the membrane it preferentially threads from one end due to the pore constriction of the membrane and is pulled through. When it emerges from the membrane, the pore provides a drag force that elongates the surrogate polymer. The flow of surrogate polymers toward the detector (96) is controlled by shutting the field off or applying a high frequency alternating current field, stopping the electrophoretic transport force. In the latter embodiment the alternating current field may assist in elongating the surrogate polymer without transporting it. To utilize the gating function of this embodiment a feedback mechanism similar to those described above is used.

Figure 20D:
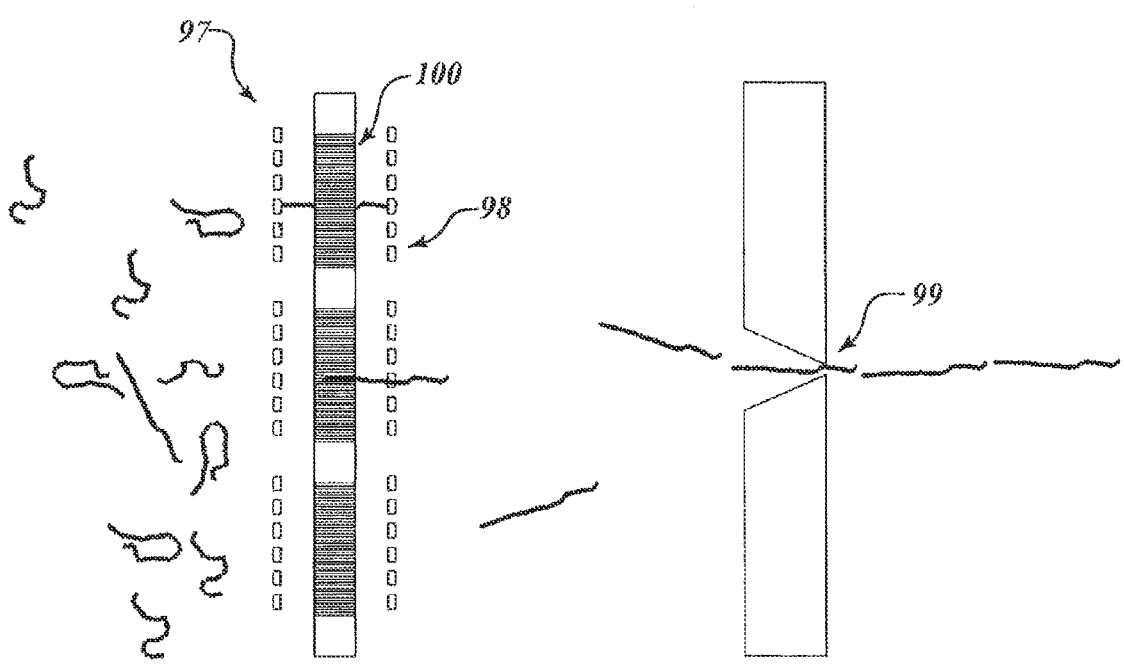

In yet another embodiment illustrated in FIG. 20D, two or more addressable gate electrodes (97, 98) are used to "feed" the detector (99). In this embodiment, each gate electrode is turned on (gate open) until a surrogate polymer is detected and is then is shut off (gate closed). The gates (100) that are "holding" a surrogate polymer molecule are opened on a regular period so that a steady stream of nonoverlapped, head-to-tail, surrogate polymers feed through the detector. Non-limiting examples of gates types include a porous membrane using surrogate polymer-bound fluorescence to detect the surrogate polymer in the gate and a nanohole that uses current to determine the presence of the surrogate polymer.

Figure 21:
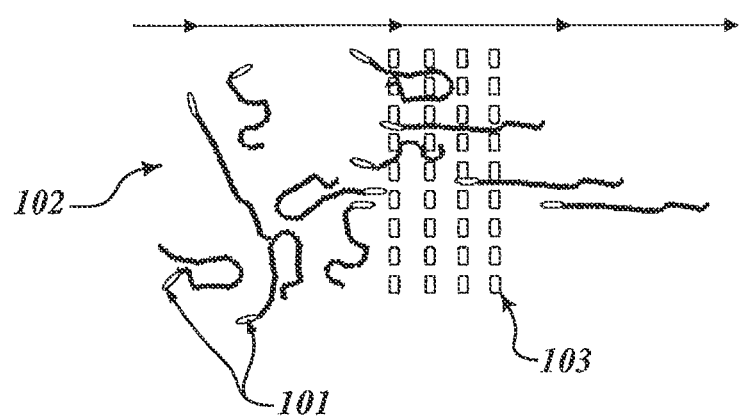
FIG. 21 depicts an affinity stretching presentation method.

Some in flow methods of presenting the surrogate polymer include the use of drag tags, hydrodynamic straightening, electric field gradients and magnetic force. In one embodiment an affinity drag tag is used to straighten and stretch the surrogate polymer as shown in FIG. 21. A weak affinity drag tag (101) is linked to the end of the surrogate polymer. The surrogate polymer (102) is then electrophoretically pulled through an appropriate affinity gel or channel (103). The weak affinity coupling creates friction on the surrogate polymer end that allows the rest of the surrogate polymer to unravel and stretch out in the field.

Some detection methods are best adapted to surrogate polymers that are tethered to a substrate on one end and are "read" by moving the detector array relative to the substrate. Such substrates are known as fixed surrogate polymer arrays (also referred to herein as fixed arrays). FIG. 15B shows that surrogate polymer can be surface tethered in a spatially stochastic manner of attachment or they can be tethered on a regular array with a single surrogate polymer at each array point. With random spatial attachment the efficiency of a detector is guided by two-dimensional Poisson statistics which, for any desired square cell size, optimally gives one molecule/cell in ~14% of the cells. By comparison, a fully loaded regular array of tethered single surrogate polymer sites is 100%. This is a 7-fold increase in detector efficiency at the cost of more preprocessing of the surrogate polymer.

Other packing scenarios having intermediate efficiencies are also possible. For example, a regular fixed array with point attachment positions that may couple multiple tethers is governed by 1-dimensional Poisson statistics. This strategy has an optimum of 37% of the sites having single surrogate polymer occupancy.

One embodiment of the regular fixed array employs a smooth substrate that has small binding sites <1 micron in size placed on a regular grid. Surrogate polymers can be adapted to bind to these sites. If they are attached randomly, 37% of the sites are single surrogate polymers. Exemplary substrate choices include: tape, such as flexible polyethylene terephthalate (PET) film, float glass, silicon wafers and stainless steel sheets. The array grid size is chosen to correspond to the detection method to be used.

An exemplary method of creating a fixed array that has a single surrogate polymer per binding site uses an array of very small spots on the substrate. These spots comprise surface bound reactive linkers. The surrogate polymers are end adapted to a molecular complex which has an overabundance of reactive endgroups, wherein each molecular complex has enough relative mobility such that it reacts with all of a spot's linker groups. Thus, each of the surface array spots only link with a single surrogate polymer. Exemplary molecular complexes include: a bead, a dendrimer and a linear polymer with sidechains.

The end-adapted surrogate polymers are reacted under dilute conditions to limit multiple surrogate polymers from reacting with a single spot. The surface bound linkers can be chosen from many existing well established chemistries, for example, biotin/strepavidin. In one embodiment, biotin can be linked to the substrate using biotinylated PEG modified to link with the substrate (e.g., thiolation for gold film or silanization for Si or $SiO_2$). In a similar manner pegalated strepavidin may be linked to the end adapted molecular complex on the surrogate polymer.

The diameter of the linker spots is minimized to limit the binding area, but the array must be made efficiently since each genome preparation may require $10^7$ to $10^9$ spots covering areas up to 100 $cm^2$ or more. E-beam lithography to expose each spot is time-intensive and expensive. However, use of E-beam lithography to define masks is a reasonable approach for preparation of the array. Molecular Imprints, Inc. has developed imprint technology (using E-beam imprint molds) whereby <20 nm features with high aspect relief can be defined in quartz masks. These may be used to define contact printing stamps for direct stamping of a linker (for example, biotin). Alternatively, a metal mask spot array may be used as a contact mask for UV ablation of a biotin monolayer. When the monolayer is against the metal it is protected from the UV, whereas unmasked areas are stripped.

Lithographic techniques using photoresist liftoff or protected etching may also be used to prepare the array. Defining lines of linkage sites rather than spots is a compromise between 2D random surface linkages and the one-to-one surrogate polymer linkage of spot arrays. In this embodiment, surrogate polymers link randomly along a line, and, provided the line width is much narrower than the average spacing between surrogate polymer along the line, the linked surrogate polymers will lie in a one dimensional Poisson distribution (i.e. a 37% fill factor at optimal Poisson statistics). The advantage of this embodiment is that lithography is a relatively simple technique and the surrogate polymer need only be adapted to have a single reactive site.

The complimentary chemistry on the end of the surrogate polymer is designed to link to the substrate binding site in a manner that prevents or minimizes more than one surrogate polymer per binding site. One embodiment employs a dendrimer attached to the end of the surrogate polymer for linking the surrogate polymer to the substrate. The dendrimer is designed to saturate or block all the coupling capacity on the binding site thereby preventing another dendrimer (on another surrogate polymer) from binding to the same site.

In another embodiment a nanopore array is prefilled and utilized as a fixed array. In this embodiment, the surrogate polymers are adapted to have stops at one end which allow the surrogate polymer to be threaded into the nanopore, but will stop the end of the surrogate polymer from complete translocation. In addition, the stop performs a function of limiting the nanopore filling to one surrogate polymer per nanopore because a second surrogate polymer cannot enter a "stopped" nanopore. After filling the array with surrogate polymers the stops are fixed in place to create a fixed array. Exemplary stops include beads and dendrimers.

In another embodiment, the fixed array may be further processed by aligning the surrogate polymers on the substrate surface to create a linearized array as depicted in FIG. 15C. In this embodiment, the grid length must be long enough to allow the surrogate polymer to lie down stretched and not overlapped by other surrogate polymers. An exemplary grid size is about 10 microns×about 500 microns.

In exemplary fixed array embodiments, the surrogate polymer is fully immobilized on the substrate surface and the detector reads the surrogate polymer reporters sequentially by moving laterally relative to the substrate surface. This method requires additional preprocessing of the surrogate polymer prior to detection, but it provides new opportunities for detection and a more readily accessible media for reread and archive functions.

For surface alignment methods, the surface area should be used efficiently, both for efficient detection but also to limit substrate costs. Thus, the surrogate polymer must be coupled to the substrate in a very controlled manner. One embodiment to realize a high density regular array of aligned surrogate polymers on the surface of the substrate is to first create a regular array of tethered surrogate polymer as described above (i.e. a fixed array). The next step is to lay the surrogate polymer down onto the substrate surface and bond it thereto.

Surrogate polymer densities on the substrate surface will depend upon process limitations and on the detection techniques. In some embodiments, the surrogate polymer density is about 1-10 µm between parallel surrogate polymers and about 10% to about 30% longer than the surrogate polymer separating sequential surrogate polymers. For example, a 150 µm surrogate polymer may be spaced along its length from the next surrogate polymer by 30 µm. To prevent the surrogate polymer from surface bonding prematurely and misaligning, it is advantageous to use a real time bonding activation method that can be applied when it is needed. For example, ultraviolet and chemical activation of the surface are exemplary bonding activation methods. Exemplary methods of laying the surrogate polymer down on the substrate surface are described below.

In one embodiment, the surrogate polymer is stretched under an electric field and the field is smoothly rotated from normal to the substrate 180 degrees through tangent to the substrate (at 90 degrees) and finally to the negative normal position. This must be performed slowly enough for the surrogate polymer to maintain a stretched position in the field. By rotating beyond 90 degrees the surrogate polymer is pinned in an extended stretched position on the substrate. When the surrogate polymer contacts the substrate it is bonded in place. In some embodiments, a rotation smaller than 180 degrees can be used, provided that the surrogate polymer moves freely to a stretched position (in the desired direction) and can subsequently be pinned (e.g. by electric force) to the substrate.

Figure 22A:
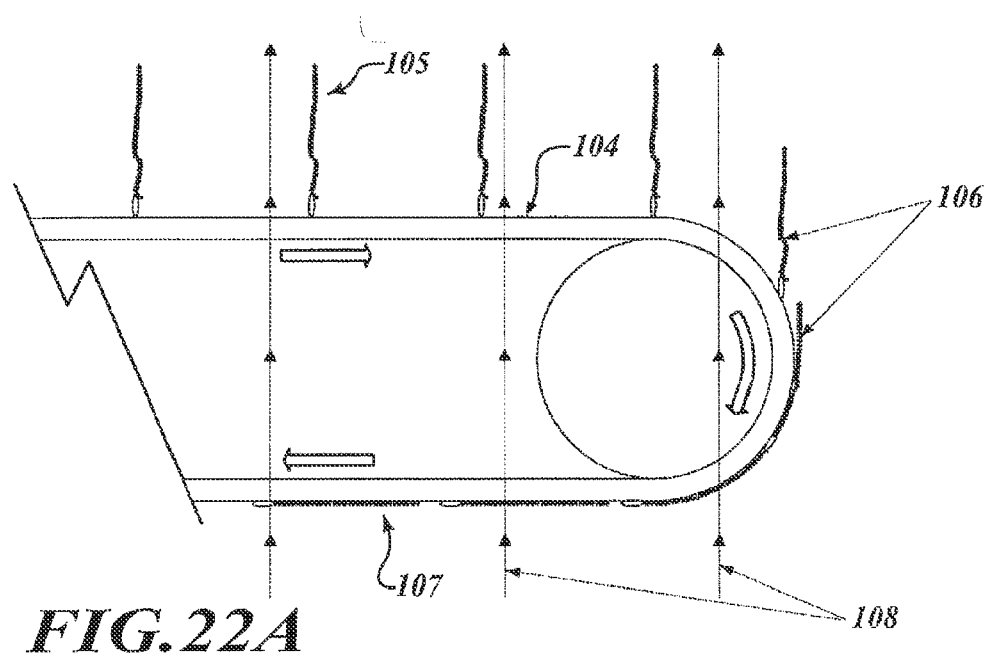
FIGS. 22A through 22D illustrate different methods of aligning nucleic acid polymers on substrate surfaces.

An exemplary embodiment is shown in FIG. 22A. In this embodiment, flexible tape substrate (104), for example a PET film, is processed continuously. As the tape moves and enters the turn of the roller, the surrogate polymers on the tape surface remain oriented normal to the tape (105). Proceeding around the first 90 degrees of the turn they remain aligned and stretched with the field (108) but rotate relative to the tape surface until they lie down on the tape surface (106). As the tape moves around the next 90 degrees of the turn, the field now pins the surrogate polymer onto the tape surface (107). If the surface and/or surrogate polymer are appropriately activated, the surrogate polymer may be bonded to the surface. If not, it may be bonded during a subsequent process or a pinning force may be maintained until the tape is "read" by the detector. Another embodiment comprises rotating a solid substrate is the field.

Figure 22B:
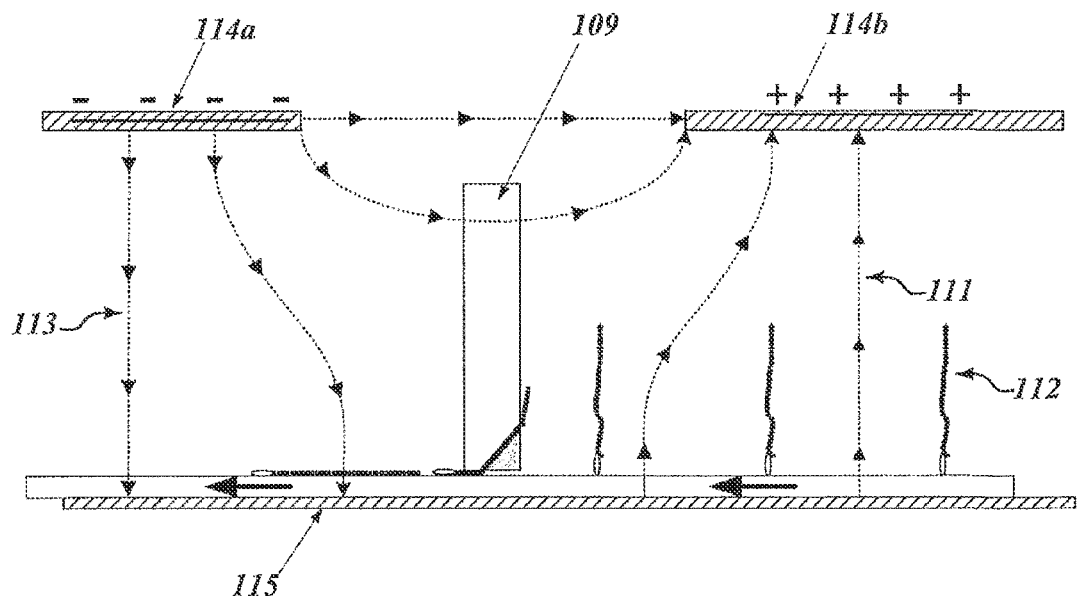

Another exemplary embodiment is illustrated in FIG. 22B. Here, the surrogate polymer (112) is laid down on the substrate using a comb (109) to guide it down to the substrate and also to steer it laterally into a straight channel (110). The comb comprises electrodes (114a, 114b) and a ground plane (115) which produce a stretching field (111) at the input side and a pinning field (113) at its exit. As the substrate is passed under the comb, the tethered surrogate polymer is "caught" and steered into a comb channel near the substrate linkage site. With further movement, the steered surrogate polymer is drawn to the substrate surface. At this point, the field is reversed and it pins the surrogate polymer to the substrate for bonding as required.

A lithographic method of making the comb uses anisotropic etching of Si wafers. Crystalline Si wafers cut and polished on the face will preferentially etch relative to the face with a potassium hydroxide etchant. The wafer is lithographically masked along one side of a regular sawtooth pattern with 57 degree switchbacks oriented parallel to 2 of the intersecting planes. After etching, the wafer is cut and polished normal to the surface and parallel to the edge of the sawtooth to form a regular pattern of notches that form the comb. Each notch has 2 smooth faces that intersect at the trough of the comb channel. The angle the trough makes with the top of the wafer is ~55 degrees and with the polished edge is ~35 degrees. To prevent shearing of the surrogate polymer, small film-based runners can be defined on the substrate or the comb.

Figure 22C:
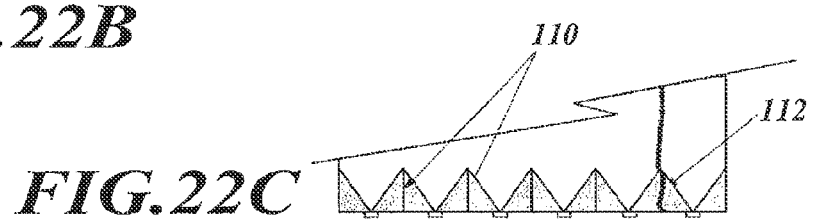
Figure 22D:
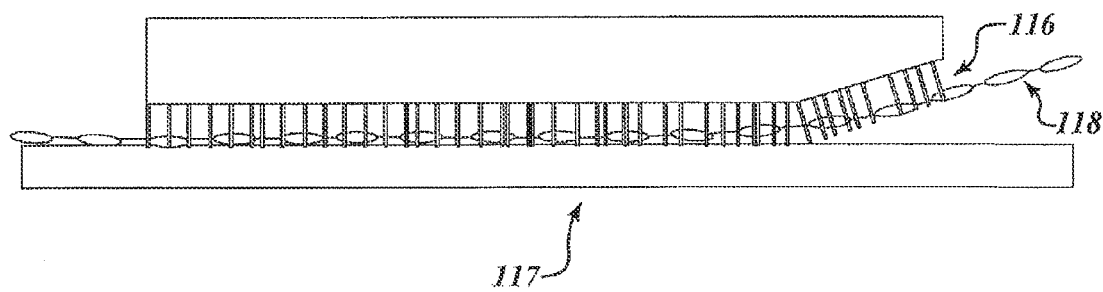

Another embodiment which is similar to the comb described above is the brush illustrated in FIG. 22C. This brush comprises very tiny bristles (116) of ~10 nm in diameter. As with the Si comb described above, the brush is drawn across a fixed array substrate (117). Provided the bristles sweep the surface, starting at the substrate-to-surrogate polymer linkage, the surrogate polymer (118) becomes entrained and stretched along the direction of brush movement. By using a field or other capture means, the surrogate polymer is then pinned to the substrate surface.

An exemplary method of making the brush employs an $Al_2O_3$ porous array as a mold to form a brush of polymer bristles. These may be based upon UV or thermal-cured polymers. An example of this process is described by Lee et al. (H. S. Lee, D. S. Kim, and T. H. Kwon, "UV nano embossing for polymer nano structures with non-transparent mold insert," *Microsystem Technologies*, vol. 13, 2007, pp. 593-599).

After a substrate has been processed by aligning surrogate polymers along its surface, further processing is possible that can serve to get more robust signal or to simplify detection. These methods are often intimately bound with the detection process. Coating linear arrays with gold to improve electron microscopy contrast is a non-limiting example of this. Further, reactive sites on the reporters can be loaded with label chemistries or contrast agents.

A tape or film substrate provides a means for continuous "web" processing of the surrogate polymer through the detection process. In one embodiment, this could be a loop in which the tape is cleaned after detection and loops back to retether new surrogate polymer product for reading. Tapes suitable for this purpose include PET, Commercial PET film has surface roughness of <40 nm which with planarization processing can be reduced to <10 nm.

EXAMPLES

Example 1

Preparation of Surrogate Polymers by Template Directed Ligation

SBX have been demonstrated in different probe types. Each modified probe is synthesized and demonstrated to extend from a primer using template-directed ligation. Ligation of probes that are 2, 3, 4, and 6 nucleotides in length have been investigated at different stages of modification. These include the following types of probes:
 (1) simple oligomer probe;
 (2) probe with two nucleotides modified with aliphatic amino linkers;
 (3) probe with a PEG3500 tether conjugated to the probe's amino linkers; and
 (4) probe with an internucleotide selectively cleavable linker (that is also modified with two aliphatic amino linkers).

Modified probes of types (1), (2), (3), and (4) have been synthesized and have each demonstrated primer-initiated extension using template-directed ligation. Selective cleavage of the selectively cleavable linker has also been demonstrated. The gel data discussed below confirms extension by processive ligation of these modified probes and confirms selective cleavage.

Figure 23:
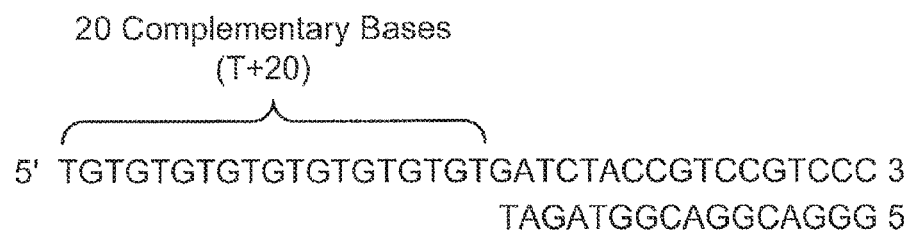
FIG. 23 shows a typical target template (SEQ ID NO: 1) that is duplexed with a 16-mer HEX-modified primer (SEQ ID NO: 2) and designed with a 20 base 5' overhang.

FIG. 23 shows a typical target template that is duplexed with a 16-mer HEX-modified primer and designed with a 20 base 5' overhang. Different length templates are used to measure processive template-directed ligation of modified probes that extend off the primer. Ligation product is sorted by gel electrophoresis into bands, and bands are identified using the HEX fluorescence. Experiments with unmodified probes (probe type (1)) were conducted to demonstrate primer extension with processive ligation. Template dependent ligation was confirmed by negative results when conducting probe ligation on mismatched templates.

FIG. 24A shows ligation products up to ~100 bases in length. These gel results demonstrate multiple, template-directed ligations of a bis(amino-modified) hexanucleotide probe (probe type (2)). For this example, the templates were fixed to magnetic beads and duplexed to a hex-labeled extension primer. Hexanucleotide oligomeric substrates of the sequence 5' (phosphate) C A (amino)C (amino)A C A 3' were hybridized to a range of progressively longer complimentary templates in the presence of T4 DNA ligase, ligating and extending from the duplexed primer. The ligation product was then denatured from its template and separated on a 20% acrylamide gel. Ligation products in lanes 1 to 4 were produced on templates with 18, 36, 68 and 100 bases beyond the primer. The upper rung in the ladder for each of the four lanes corresponds to ligated additions of 3, 6, 12 and 17 hexamers. These upper rungs are relatively strong bands and indicate much longer ligation products are possible.

As a point of reference, the single band indicating extension of 100 bases is estimated to be 0.1 μmoles of ligated product using the measurement sensitivity as a reference. This is equivalent to 6 trillion bases or 60 genomes @20× coverage worth of "read" material. This demonstrates why processing cost is low, scaling is simple, and the advantage of size enrichment to only send the longest and highest value surrogate polymers to the detection step.

The gel results shown in FIG. 24B demonstrate multiple, template-directed ligations of tetranucleotide probes modified with a PEG3500 attached at each end to two modified probe nucleotides (probe-type (3)). The probe precursor was a bis 2,3 (amino) tetranucleotide, 5' (phosphate) C(amino) A (amino)C A 3'. The aliphatic amino modifiers were then converted to 4-formylbenzoate (4FB), and bis (amino) PEG3500 converted to bis (HyNic) PEG3500 (HyNic conjugation kit purchased from Solulink, CA). Under dilute conditions the bifunctional PEG3500 was reacted with the bis 2,3 (4FB) tetranucleotide to form a circularized PEG loop. As in the previous example, a template was fixed to magnetic beads and duplexed to a hex-labeled extension primer. In this example, the template has 20 bases beyond the primer. The PEG-circularized tetranucleotide probes were hybridized to the complimentary template and ligated in the presence of T4 DNA ligase. The ligation product was then separated from its template and separated on a 20% acrylamide gel. The gel results indicate ligation of product polymer containing four PEG-modified probes. This demonstrates that doubly modified probes loaded with high masses of 3500 Daltons can be progressively ligated to a template. (Due to limitations of the gel, it was difficult to resolve incorporations of these ligated mass-loaded probes to longer than four probes.)

FIG. 24C shows gel results of ligated tetranucleotide probes (probe-type (4)) with amino-modifiers that are further modified to have a selectively cleavable bond (cb). This bond is a modification to an internucleotide phosphodiester and will cleave under acidic conditions. The probe was a bis 2,3 (amino) tetranucleotide, 5' (phosphate) A (amino)C(cb)T (amino)C 3'. This template has 36 bases beyond the primer and the gel ladder indicates ligation was complete with a maximum of 9 tetranucleotide additions. The control has the same reagent mix with no ligase.

FIG. 24D shows results for a test of the selective cleavage. A 26-mer was produced with a selectively cleavable bond between the $17^{th}$ and $18^{th}$ nucleotide. Lane 1 shows the 26-mer control. Lane 2 shows the 17-mer cleavage product after subjecting the 26-mer to acid. Results indicate essentially complete cleavage of the 26-mer into shorter segments at very high level of completion.

Example 2

Figure 25:
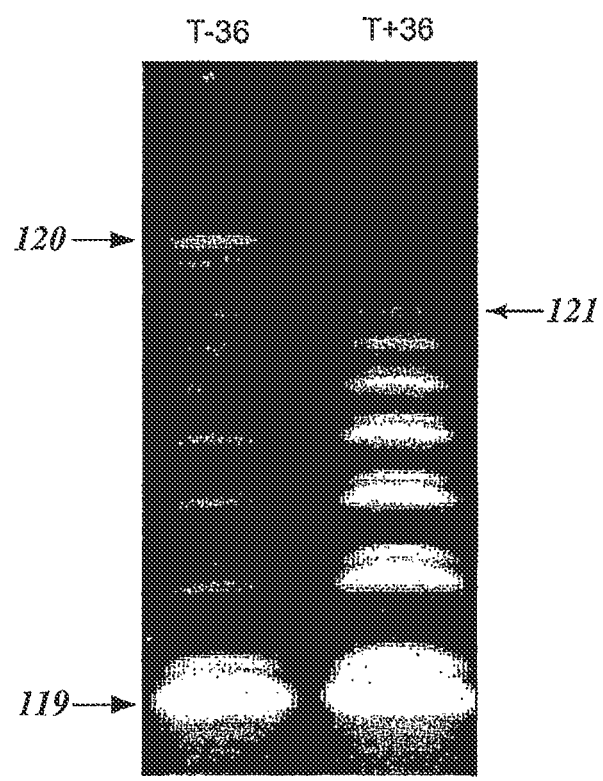
FIG. 25 is a gel of a ligation experiment.

Preparation of a Paired-End Surrogate Polymer by Rolling Circular Polymerization To prepare a paired-end surrogate polymer, ligation was initiated from each end of a primer that was hybridized on a ss-DNA template where 36 bases of the template extended beyond both the 3' OH and the 5' phosphorylated ends of the primer. Ligation products with 4-mer probes extending from either end of the primer were synthesized. FIG. 25 shows the gel results of ligated tetranucleotide probes (probe-type (4)) bis 2,3 (amino) tetranucleotide, 5' (phosphate) A (amino)C (cb)T (amino)C 3' with 2 different templates, T−36 and T+36. Template T+36 has 36 bases beyond the 3' OH end of the primer whereas the T+36 has 36 bases beyond the 5' phosphate end of the primer. In each case, the probes were incorporated and ligated. The gel shows unextended template (119) and a maximum of 9 (120) and 8 (121) tetranucleotide additions in the T −36 and T +36 templates, respectively.

---

---

The invention claimed is:

1. A method of detecting an analyte, comprising:
a) providing at least one analyte;
b) providing at least one indicator moiety, wherein the indicator moiety is not associated with the analyte;
c) providing a detector construct, wherein the detector construct comprises a first and a second reservoir comprising first and second electrodes, respectively, wherein the first and second reservoirs are separated by a nanopore substrate positioned between the first and second reservoirs, and wherein the nanopore substrate has at least one nanopore channel through the substrate;
d) providing an electric potential to the first and second electrodes, wherein the electric potential is sufficient to translocate the at least one analyte and the at least one indicator moiety through the at least one nanopore channel; and
e) detecting a change in an optical signal emitted from the at least one indicator moiety at or near the at least one nanopore channel as the at least one analyte translocates through the at least one nanopore channel and thereby detecting the analyte.

2. The method of claim 1, further comprising providing an excitation wavelength, wherein the excitation wavelength is sufficient to induce a fluorescent signal from the at least one indicator moiety.

3. The method of claim 1, wherein the at least one analyte is a nucleic acid.

4. The method of claim 1, wherein the at least one analyte is a surrogate polymer.

5. The method of claim 1, wherein the at least one indicator moiety is at least one fluorophore, wherein the first reservoir comprises a high concentration of fluorophore relative to the second reservoir, and detecting a change in the optical signal further comprises detecting a change in a fluorescent signal as the at least one fluorophore translocates through the at least one nanopore channel.

6. The method of claim 5, wherein epifluorescence microscopy is used for detecting the change in the fluorescent signal.

7. The method of claim 5, wherein conoscopy is used for detecting the change in the fluorescent signal.

8. The method of claim 5, wherein the nanopore substrate comprises a blocking film.

9. The method of claim 5, wherein the at least one fluorophore is fluorescein.

10. The method of claim 5, wherein the second reservoir comprises a fluorescence quenching agent, and wherein detecting a change in the optical signal further comprises detecting a change in the fluorescent signal as the at least one fluorophore or a quenching agent translocates through the at least one nanopore channel.

11. The method of claim 10, wherein the quenching agent is an acceptor for fluorescence resonance energy transfer or a free radical.

12. The method of claim 1, further comprising providing two indicator moieties, wherein a first indicator moiety is an indicator ion, and a second indicator moiety is a fluorescence indicator, wherein the first reservoir comprises the indicator ion, the second reservoir comprises the fluorescence indicator, and wherein detecting a change in the optical signal further comprises detecting a change in a fluorescence signal emitted as either the first indicator moiety or the second indicator moiety passes through the at least one nanopore channel.

13. The method of claim 12, wherein the second reservoir further comprises a non-fluorescing absorber.

14. The method of claim 12, wherein the at least one nanopore channel is masked to create a circular opening of about 1 µm in diameter, and wherein the opening is concentric with the nanopore channel.

15. The method of claim 12, wherein the indicator ion is a calcium ion, a singlet hydrogen ion, a singlet oxygen ion, a potassium ion, a zinc ion, a magnesium ion, a chlorine ion, or a sodium ion.

16. The method of claim 12, wherein the second indicator moiety is a calcium indicator moiety.

17. The method of claim 12, wherein the second indicator moiety is fluorescence quencher.

18. The method of claim 12, wherein the first reservoir comprises iodide ions and the second reservoir comprises fluorescein.

19. The method of claim 1 further comprising providing two indicator moieties, wherein the first reservoir comprises a first indicator moiety and the second reservoir comprises a second indicator moiety, wherein the first and second indicator moieties are capable of combining to form a third indicator moiety in an excited state, and detecting a change in the optical signal further comprises detecting photons which are emitted when the third indicator moiety relaxes to a ground state.

20. The method of claim 1, wherein the nanopore substrate comprises a nanopore array, and wherein the nanopore array shares the first and second reservoirs.

* * * * *

UNITED STATES PATENT AND TRADEMARK OFFICE
CERTIFICATE OF CORRECTION

| | | |
|---|---|---|
| PATENT NO. | : 9,771,614 B2 | Page 1 of 1 |
| APPLICATION NO. | : 14/590894 | |
| DATED | : September 26, 2017 | |
| INVENTOR(S) | : Mark Stamatios Kokoris et al. | |

It is certified that error appears in the above-identified patent and that said Letters Patent is hereby corrected as shown below:

In the Claims

<u>Column 65, Line 4:</u>
"moiety is fluorescence quencher." should read,
--moiety is a fluorescence quencher.--.

Signed and Sealed this
Third Day of April, 2018

Andrei Iancu
*Director of the United States Patent and Trademark Office*

SEQUENCE LISTING

<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Typical target template

<400> SEQUENCE: 1
tgtgtgtgtg tgtgtgtgtg atctaccgtc cgtccc                36

<210> SEQ ID NO 2
<211> LENGTH: 16
<212> TYPE: DNA
<213> ORGANISM: Artificial Sequence
<220> FEATURE:
<223> OTHER INFORMATION: 16-mer primer sequnence

<400> SEQUENCE: 2
gggacggacg gtagat                16